US008420373B2

(12) United States Patent
Delputte et al.

(10) Patent No.: US 8,420,373 B2
(45) Date of Patent: Apr. 16, 2013

(54) PERMISSIVE CELLS AND USES THEREOF

(75) Inventors: Peter Delputte, Gent Oost-vlaanderen (BE); Hans Nauwynck, Zomergem (BE); Hanne Van Gorp, Merelbeke (BE)

(73) Assignee: Universiteit Gent, Ghent ( * ) Notice: Subject to any disclaimer, the term of this patent is extended or adjusted under 35 U.S.C. 154(b) by 307 days.

(21) Appl. No.: 12/452,675

(22) PCT Filed: Jul. 23, 2008

(86) PCT No.: PCT/EP2008/006045
§ 371 (c)(1),
(2), (4) Date: Jan. 13, 2010

(87) PCT Pub. No.: WO2009/024239
PCT Pub. Date: Feb. 26, 2009

(65) Prior Publication Data
US 2010/0158947 A1 Jun. 24, 2010

(30) Foreign Application Priority Data

Jul. 27, 2007 (EP) .................................. 07014842
Jun. 19, 2008 (GB) .................................. 0811278.1

(51) Int. Cl.
*C12N 7/02* (2006.01)
*C12N 7/04* (2006.01)
*C12Q 1/70* (2006.01)

(52) U.S. Cl.
USPC ........... 435/239; 435/235.1; 435/5; 435/7.21; 435/236

(58) Field of Classification Search ........................ None
See application file for complete search history.

(56) References Cited

U.S. PATENT DOCUMENTS

| | | | |
|---|---|---|---|
| 5,620,691 | A | 4/1997 | Wensvoort et al. |
| 6,197,310 | B1 | 3/2001 | Wensvoort et al. |
| 6,455,245 | B1 | 9/2002 | Wensvoort et al. |
| 6,806,086 | B2 | 10/2004 | Wensvoort et al. |
| 7,335,473 | B2 | 2/2008 | Wensvoort et al. |
| 2005/0271685 | A1 | 12/2005 | Calvert et al. |
| 2011/0177118 | A1* | 7/2011 | Zuckermann ............. 424/204.1 |

FOREIGN PATENT DOCUMENTS

| | | |
|---|---|---|
| WO | WO 91/09955 | 7/1991 |
| WO | WO 92/20808 | 11/1992 |
| WO | WO 94/12650 | 6/1994 |
| WO | WO 2009/024239 A2 | 2/2009 |

OTHER PUBLICATIONS

Bonder et al, Cytokin 17:187-197, 2002.*
Kuhn et al (Cellular and Molecular Life Sciences 61:2738-2743, 2004).*
Martens et al (Journal of Pathology 208:574-589, 2006).*
Calvert et al., CD163 expression confers susceptibility to porcine reproductive and respiratory syndrome viruses, Journal of Virology, May 9, 2007, pp. 7371-7379, vol. 81, No. 14, The American Society for Microbiology, US.
Delputte, et al., Analysis of porcine reproductive and respiratory syndrome virus attachment and internalization: distinctive roles for heparan sulphate and sialoadhesin, Journal of General Virology, May 2005, pp. 1441-1445, vol. 86.
Sanchez-Torres et al., Expression of Porcine CD163 on Monocytes/Macrophages Correlates With Permissiveness to African Swine Fever Infection, Archives of Virology, Jan. 1, 2003, pp. 2307-2323, vol. 148.
PCT International Search Report, PCT/EP2008/006045, dated May 11, 2009.
Calvert et al., CD163 expression confers susceptibility to porcine reproductive and respiratory syndrome viruses, Journal of Virology, May 9, 2007, pp. 7371-7379, vol. 81, No. 14, The American Society for Microbiology, US.
Delputte, et al., Analysis of porcine reproductive and respiratory syndrome virus attachment and internalization: distictive roles for heparan sulphate and sialoadhesin, Journal of General Virology, May 2005, pp. 1441-1445, vol. 86.
Sanchez-Torres et al., Expression of Porcine CD163 on Monocytes/Macrophages Correlates With Permissiveness to African Swine Fever Infection, Archives of Virology, Jan. 1, 2003, pp. 2307-2323, vol. 148.
U.S. Appl. No. 12/227,106, filed Nov. 7, 2008, Nauwynck et al., Sialoadhesin-Related Compositions and Methods.
U.S. Appl. No. 11/781,558, filed Jul. 23, 2007, Pensaert et al., Nucleic Acid Encoding Polypeptide Involved in Cellular Entrance of the PRRS Virus.
Karniychuk et al., Quantitative Changes of Sialoadhesin and CD163 Positive Macrophages in the Implantation Sites and Organs of Porcine Embryos/Fetuses During Gestation, Placenta, 2009, pp. 497-500, vol. 30.

* cited by examiner

*Primary Examiner* — Mary E Mosher
(74) *Attorney, Agent, or Firm* — TraskBritt

(57) ABSTRACT

The invention relates generally to the field of virology. More particularly, the present invention relates to methods for determining the permissiveness of a cell for a virus that is a member of the family Arteriviridae or Coronaviridae or Asfarviridae, in particular for Porcine Reproductive and Respiratory Syndrome Virus (PRRSV). The invention further provides methods and compositions related to the generation of host cells permissive for a virus that is a member of the family Arteriviridae or Coronaviridae or Asfarviridae, in particular for Porcine Reproductive and Respiratory Syndrome Virus (PRRSV). Methods of using said cells thus identified or thus generated, in preparing a culture of a virus that is a member of the family Arteriviridae or Coronaviridae or Asfarviridae, as well as the use of said virus for the purpose of vaccine production or diagnosis, are also provide by the present invention.

14 Claims, 10 Drawing Sheets

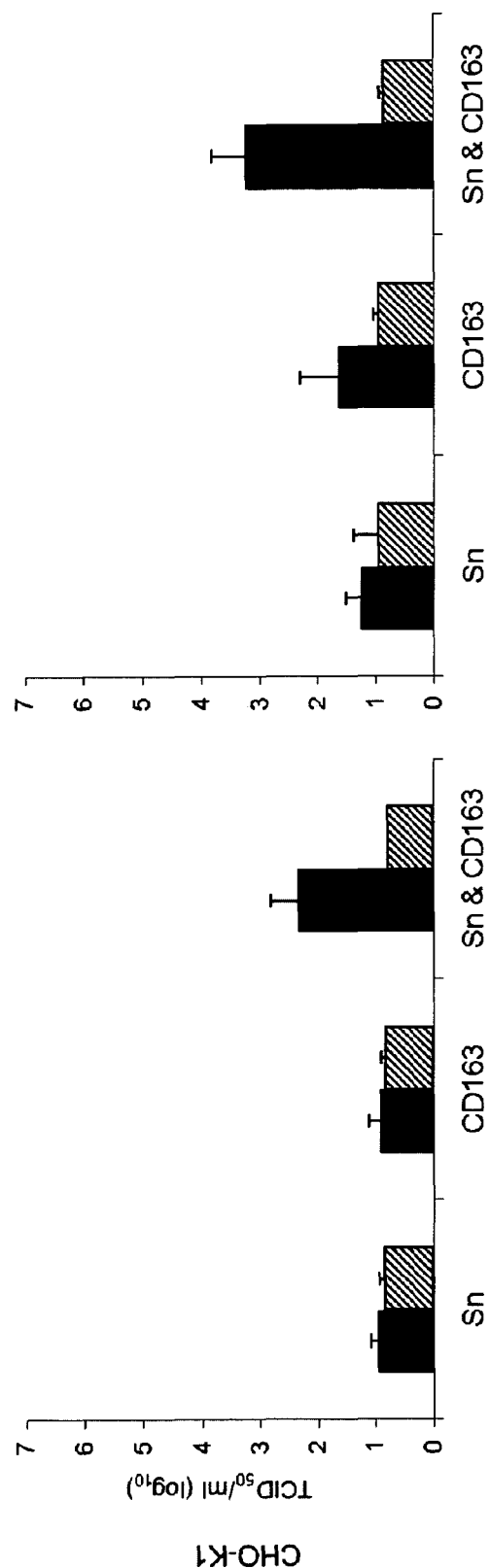
Fig.3 -Continued

Fig. 3 -Continued
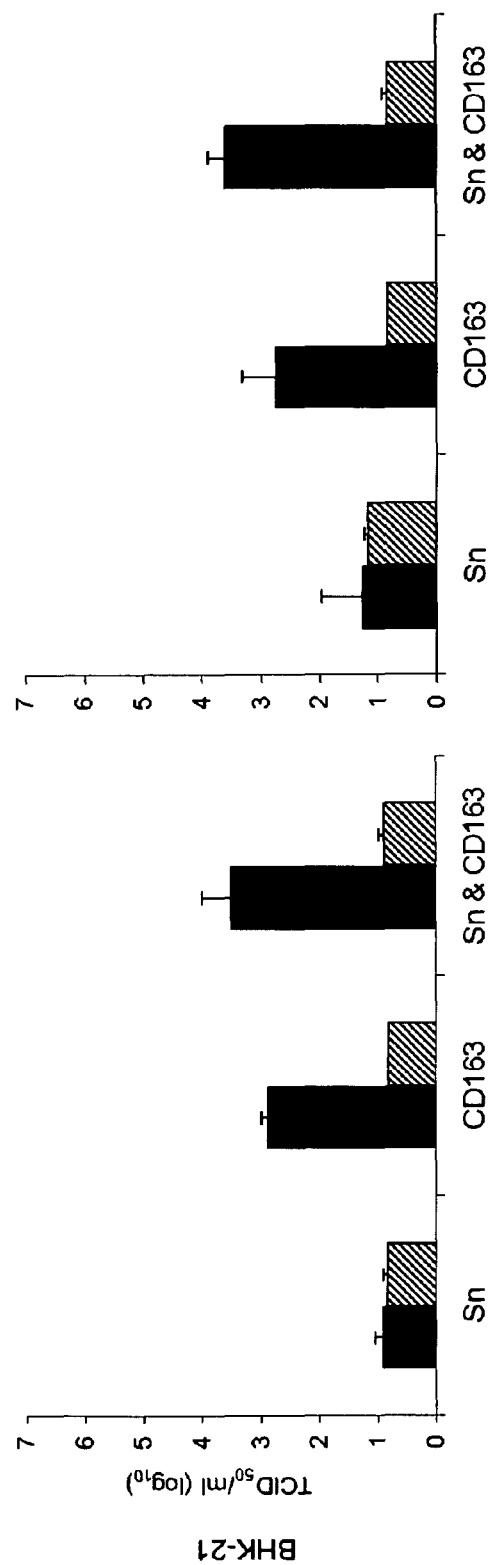

SEQUENCE LISTING

```
<160> NUMBER OF SEQ ID NOS: 16

<210> SEQ ID NO 1
<211> LENGTH: 3400
<212> TYPE: DNA
<213> ORGANISM: Sus scrofa
<300> PUBLICATION INFORMATION:
<308> DATABASE ACCESSION NUMBER: GenBank/AJ311716
<309> DATABASE ENTRY DATE: 2005-04-15
<313> RELEVANT RESIDUES IN SEQ ID NO: (1)..(3400)

<400> SEQUENCE: 1
atggtgctac ttgaagactc tggatctgca gactttagaa gatgttctgc ccatttaagt      60
tccttcactt ttgctgtagt cgctgttctc agtgcctgct tggtcactag ttctcttgga     120
ggaaaagaca aggagctgag gctaacgggt ggtgaaaaca agtgctctgg aagagtggag     180
gtgaaagtgc aggaggagtg gggaactgtg tgtaataatg gctgggacat ggatgtggtc     240
tctgttgttt gtaggcagct gggatgtcca actgctatca aagccactgg atgggctaat     300
tttagtgcag gttctggacg catttggatg gatcatgttt cttgtcgagg gaatgagtca     360
gctctctggg actgcaaaca tgatggatgg ggaaagcata actgtactca ccaacaggat     420
gctggagtaa cctgctcaga tggatctgat ttagagatga ggctggtgaa tggaggaaac     480
cggtgcttag gaagaataga agtcaaattt caagagcggt ggggaacagt gtgtgatgat     540
aacttcaaca taaatcatgc ttctgtggtt tgtaaacaac ttgaatgtgg aagtgctgtc     600
agtttctctg gttcagctaa ttttggagaa ggttctggac caatctggtt tgatgatctt     660
gtatgcaatg gaaatgagtc agctctctgg aactgcaaac atgaaggatg gggaaagcac     720
```

```
aattgcgatc atgctgagga tgctggagtg atttgcttaa atggagcaga cctgaaactg    780
agagtggtag atggactcac tgaatgttca ggaagattgg aagtgaaatt ccaaggagaa    840
tggggaacaa tctgtgatga tggctgggat agtgatgatg ccgctgtggc atgtaagcaa    900
ctgggatgtc caactgctgt cactgccatt ggtcgagtta acgccagtga gggaactgga    960
cacatttggc ttgacagtgt tcttgccat ggacacgagt ctgctctctg gcagtgtaga   1020
caccatgaat ggggaaagca ttattgcaat cataatgaag atgctggtgt gacatgttct   1080
gatggatcag atctggaact gagacttaaa ggtggaggca gccactgtgc tgggacagtg   1140
gaggtggaaa ttcagaaact ggtaggaaaa gtgtgtgata aagctgggg actgaaagaa   1200
gctgatgtgg tttgcaggca gctgggatgt ggatctgcac tcaaaacatc atatcaagtt   1260
tattccaaaa ccaaggcaac aaacacatgg ctgtttgtaa gcagctgtaa tggaaatgaa   1320
acttctcttt gggactgcaa gaattggcag tggggtggac ttagttgtga tcactatgac   1380
gaagccaaaa ttacctgctc agcccacagg aaacccaggc tggttggagg ggacattccc   1440
tgctctggtc gtgttgaagt acaacatgga gacacgtggg gcaccgtctg tgattctgac   1500
ttctctctgg aggcggccag cgtgctgtgc agggaactac agtgcggcac tgtggtttcc   1560
ctcctggggg gagctcactt tggagaagga agtggacaga tctgggctga agaattccag   1620
tgtgaggggc acgagtccca cctttcactc tgcccagtag caccccgccc tgacgggaca   1680
tgtagccaca gcagggacgt cggcgtagtc tgctcaagat acacacaaat ccgcttggtg   1740
aatggcaaga cccatgtga aggaagagtg gagctcaaca ttcttgggtc ctgggggtcc   1800
ctctgcaact ctcactggga catggaagat gcccatgttt tatgccagca gcttaaatgt   1860
ggagttgccc tttctatccc ggaggagca ccttttggga aaggaagtga gcaggtctgg   1920
aggcacatgt ttcactgcac tgggactgag aagcacatgg gagattgttc cgtcactgct   1980
ctgggcgcat cactctgttc ttcagggcaa gtggcctctg taatctgctc agggaaccag   2040
agtcagacac tatcccgtg caattcatca tcctcggacc catcaagctc tattatttca   2100
gaagaaagtg gtgttgcctg catagggagt ggtcaacttc gcctggtcga tggaggtggt   2160
cgttgtgctg ggagagtaga ggtctatcct ggggcatcct ggggcaccat ctgtgatgac   2220
agctgggacc tgaatgatgc ccatgtggtg tgcaaacagc tgagctgtgg atgggccatt   2280
aatgccactg gttctgctca ttttggggaa ggaacagggc ccatttggct ggatgagata   2340
aactgtaatg gaaaagaatc tcatatttgg caatgccact cacatggttg ggggcggcac   2400
aattgcaggc ataaggagga tgcaggagtc atctgctcag agttcatgtc tctgagactg   2460
atcagtgaaa acagcagaga gacctgtgca gggcgcctgg aagttttta caacggagct   2520
tggggcagcg ttggcaggaa tagcatgtct ccagccacag tggggtggt atgcaggcag   2580
ctgggctgtg cagacagagg ggacatcagc cctgcatctt cagacaagac agtgtccagg   2640
cacatgtggg tggacaatgt tcagtgtcct aaaggacctg acacactatg gcagtgcccc   2700
tcatctccat ggaagaagag actggccagc ccctcagagg agacatggat cacatgtgcc   2760
aacaaaataa gacttcaaga aggaaacact aattgttctg gacgtgtgga gatctggtac   2820
ggaggttcct ggggcactgt gtgtgacgac tcctgggacc ttgaagatgc tcaggtggtg   2880
tgccgacagc tgggctgtgg ctcagctttg gaggcaggaa aagagcccgc atttggccag   2940
gggactgggc ccatatggct caatgaagtg aagtgcaagg ggaatgaacc ctccttgtgg   3000
gattgtcctg ccagatcctg gggccacagt gactgtggac acaaggagga tgctgctgtg   3060
acgtgctcag aaattgcaaa gagccgagaa tccctacatg ccacaggtcg ctcatctttt   3120
```

```
gttgcacttg caatctttgg ggtcattctg ttggcctgtc tcatcgcatt cctcatttgg    3180
actcagaagc gaagacagag gcagcggctc tcagttttct caggaggaga gaattctgtc    3240
catcaaattc aataccggga gatgaattct tgcctgaaag cagatgaaac ggatatgcta    3300
aatccctcag gagaccactc tgaagtacaa tgaaaaggaa aatgggaatt ataacctggt    3360
gagttcagcc tttaagatac cttgatgaag acctggacta                         3400
```

<210> SEQ ID NO 2
<211> LENGTH: 1115
<212> TYPE: PRT
<213> ORGANISM: Sus scrofa
<300> PUBLICATION INFORMATION:
<308> DATABASE ACCESSION NUMBER: GenPept/CAC84397
<309> DATABASE ENTRY DATE: 2005-04-15
<313> RELEVANT RESIDUES IN SEQ ID NO: (1)..(1115)

<400> SEQUENCE: 2

```
Met Asp Lys Leu Arg Met Val Leu His Glu Asn Ser Gly Ser Ala Asp
1               5                   10                  15

Phe Arg Arg Cys Ser Ala His Leu Ser Ser Phe Thr Phe Ala Val Val
            20                  25                  30

Ala Val Leu Ser Ala Cys Leu Val Thr Ser Ser Leu Gly Gly Lys Asp
        35                  40                  45

Lys Glu Leu Arg Leu Thr Gly Gly Glu Asn Lys Cys Ser Gly Arg Val
    50                  55                  60

Glu Val Lys Val Gln Glu Glu Trp Gly Thr Val Cys Asn Asn Gly Trp
65                  70                  75                  80

Asp Met Asp Val Val Ser Val Val Cys Arg Gln Leu Gly Cys Pro Thr
                85                  90                  95

Ala Ile Lys Ala Thr Gly Trp Ala Asn Phe Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Asn Cys Thr His Gln Gln
    130                 135                 140

Asp Ala Gly Val Thr Cys Ser Asp Gly Ser Asp Leu Glu Met Gly Leu
145                 150                 155                 160

Val Asn Gly Gly Asn Arg Cys Leu Gly Arg Ile Glu Val Lys Phe Gln
                165                 170                 175

Gly Arg Trp Gly Thr Val Cys Asp Asp Asn Phe Asn Ile Asn His Ala
            180                 185                 190

Ser Val Val Cys Lys Gln Leu Glu Cys Gly Ser Ala Val Ser Phe Ser
        195                 200                 205

Gly Ser Ala Asn Phe Gly Glu Gly Ser Gly Pro Ile Trp Phe Asp Asp
    210                 215                 220

Leu Val Cys Asn Gly Asn Glu Ser Ala Leu Trp Asn Cys Lys His Glu
225                 230                 235                 240

Gly Trp Gly Lys His Asn Cys Asp His Ala Glu Asp Ala Gly Val Ile
                245                 250                 255

Cys Leu Asn Gly Ala Asp Leu Lys Leu Arg Val Val Asp Gly Val Thr
            260                 265                 270

Glu Cys Ser Gly Arg Leu Glu Val Lys Phe Gln Gly Glu Trp Gly Thr
        275                 280                 285

Ile Cys Asp Asp Gly Trp Asp Ser Asp Asp Ala Ala Val Ala Cys Lys
    290                 295                 300
```

```
Gln Leu Gly Cys Pro Thr Ala Val Thr Ala Ile Gly Arg Val Asn Ala
305                 310                 315                 320

Ser Glu Gly Thr Gly His Ile Trp Leu Asp Ser Val Ser Cys His Gly
                325                 330                 335

His Glu Ser Ala Leu Trp Gln Cys Arg His Glu Trp Gly Lys His
            340                 345                 350

Tyr Cys Asn His Asp Glu Asp Ala Gly Val Thr Cys Ser Asp Gly Ser
        355                 360                 365

Asp Leu Glu Leu Arg Leu Lys Gly Gly Ser His Cys Ala Gly Thr
        370                 375                 380

Val Glu Val Glu Ile Gln Lys Leu Val Gly Lys Val Cys Asp Arg Ser
385                 390                 395                 400

Trp Gly Leu Lys Glu Ala Asp Val Val Cys Arg Gln Leu Gly Cys Gly
                405                 410                 415

Ser Ala Leu Lys Thr Ser Tyr Gln Val Tyr Ser Lys Thr Lys Ala Thr
            420                 425                 430

Asn Thr Trp Leu Phe Val Ser Cys Asn Gly Asn Glu Thr Ser Leu
        435                 440                 445

Trp Asp Cys Lys Asn Trp Gln Trp Gly Gly Leu Ser Cys Asp His Tyr
        450                 455                 460

Asp Glu Ala Lys Ile Thr Cys Ser Ala His Arg Lys Pro Arg Leu Val
465                 470                 475                 480

Gly Gly Asp Ile Pro Cys Ser Gly Arg Val Glu Val Gln His Gly Asp
                485                 490                 495

Thr Trp Gly Thr Val Cys Asp Ser Asp Phe Ser Leu Glu Ala Ala Ser
            500                 505                 510

Val Leu Cys Arg Glu Leu Gln Cys Gly Thr Val Val Ser Leu Leu Gly
        515                 520                 525

Gly Ala His Phe Gly Glu Gly Ser Gly Gln Ile Trp Ala Glu Glu Phe
        530                 535                 540

Gln Cys Glu Gly His Glu Ser His Leu Ser Leu Cys Pro Val Ala Pro
545                 550                 555                 560

Arg Pro Asp Gly Thr Cys Ser His Ser Arg Asp Val Gly Val Val Cys
                565                 570                 575

Ser Arg Tyr Thr Gln Ile Arg Leu Val Asn Gly Lys Thr Pro Cys Glu
            580                 585                 590

Gly Arg Val Glu Leu Asn Ile Leu Gly Ser Trp Gly Ser Leu Cys Asn
        595                 600                 605

Ser His Trp Asp Met Glu Asp Ala His Val Leu Cys Gln Gln Leu Lys
        610                 615                 620

Cys Gly Val Ala Leu Ser Ile Pro Gly Gly Ala Pro Phe Gly Lys Gly
625                 630                 635                 640

Ser Glu Gln Val Trp Arg His Met Phe His Cys Thr Gly Thr Glu Lys
                645                 650                 655

His Met Gly Asp Cys Ser Val Thr Ala Leu Gly Ala Ser Leu Cys Ser
            660                 665                 670

Ser Gly Gln Val Ala Ser Val Ile Cys Ser Gly Asn Gln Ser Gln Thr
        675                 680                 685

Leu Ser Pro Cys Asn Ser Ser Ser Asp Pro Ser Ser Ser Ile Ile
        690                 695                 700

Ser Glu Glu Asn Gly Val Ala Cys Ile Gly Ser Gly Gln Leu Arg Leu
705                 710                 715                 720

Val Asp Gly Gly Gly Arg Cys Ala Gly Arg Val Glu Val Tyr His Glu
                725                 730                 735
```

Gly Ser Trp Gly Thr Ile Cys Asp Asp Ser Trp Asp Leu Asn Asp Ala
            740                 745                 750

His Val Val Cys Lys Gln Leu Ser Cys Gly Trp Ala Ile Asn Ala Thr
            755                 760                 765

Gly Ser Ala His Phe Gly Glu Gly Thr Gly Pro Ile Trp Leu Asp Glu
            770                 775                 780

Ile Asn Cys Asn Gly Lys Glu Ser His Ile Trp Gln Cys His Ser His
785                 790                 795                 800

Gly Trp Gly Arg His Asn Cys Arg His Lys Glu Asp Ala Gly Val Ile
                805                 810                 815

Cys Ser Glu Phe Met Ser Leu Arg Leu Ile Ser Glu Asn Ser Arg Glu
                820                 825                 830

Thr Cys Ala Gly Arg Leu Glu Val Phe Tyr Asn Gly Ala Trp Gly Ser
                835                 840                 845

Val Gly Arg Asn Ser Met Ser Pro Ala Thr Val Gly Val Val Cys Arg
            850                 855                 860

Gln Leu Gly Cys Ala Asp Arg Gly Asp Ile Ser Pro Ala Ser Ser Asp
865                 870                 875                 880

Lys Thr Val Ser Arg His Met Trp Val Asp Asn Val Gln Cys Pro Lys
                885                 890                 895

Gly Pro Asp Thr Leu Trp Gln Cys Pro Ser Ser Pro Trp Lys Lys Arg
            900                 905                 910

Leu Ala Ser Pro Ser Glu Glu Thr Trp Ile Thr Cys Ala Asn Lys Ile
            915                 920                 925

Arg Leu Gln Glu Gly Asn Thr Asn Cys Ser Gly Arg Val Glu Ile Trp
            930                 935                 940

Tyr Gly Gly Ser Trp Gly Thr Val Cys Asp Asp Ser Trp Asp Leu Glu
945                 950                 955                 960

Asp Ala Gln Val Val Cys Arg Gln Leu Gly Cys Gly Ser Ala Leu Glu
                965                 970                 975

Ala Gly Lys Glu Ala Ala Phe Gly Gln Gly Thr Gly Pro Ile Trp Leu
            980                 985                 990

Asn Glu Val Lys Cys Lys Gly Asn Glu Thr Ser Leu Trp Asp Cys Pro
            995                 1000                1005

Ala Arg Ser Trp Gly His Ser Asp Cys Gly His Lys Glu Asp Ala
            1010                1015                1020

Ala Val Thr Cys Ser Glu Ile Ala Lys Ser Arg Glu Ser Leu His
            1025                1030                1035

Ala Thr Gly Arg Ser Ser Phe Val Ala Leu Ala Ile Phe Gly Val
            1040                1045                1050

Ile Leu Leu Ala Cys Leu Ile Ala Phe Leu Ile Trp Thr Gln Lys
            1055                1060                1065

Arg Arg Gln Arg Gln Arg Leu Ser Val Phe Ser Gly Gly Glu Asn
            1070                1075                1080

Ser Val His Gln Ile Gln Tyr Arg Glu Met Asn Ser Cys Leu Lys
            1085                1090                1095

Ala Asp Glu Thr Asp Met Leu Asn Pro Ser Gly Asp His Ser Glu
            1100                1105                1110

Val Gln
    1115

<210> SEQ ID NO 3
<211> LENGTH: 4405
<212> TYPE: DNA

```
<213> ORGANISM: mus musculus
<300> PUBLICATION INFORMATION:
<308> DATABASE ACCESSION NUMBER: GenBank/AF274883
<309> DATABASE ENTRY DATE: 2001-05-10
<313> RELEVANT RESIDUES IN SEQ ID NO: (1)..(4405)

<400> SEQUENCE: 3
gtggtcatcc actttctaca gagaacacgt ctatgaaata gtatcaggag acacacggag      60
ccatcaaaat catcaagctt tggaatgggt ggacacagaa tggttcttct tggaggtgct     120
ggatctcctg gttgtaaaag gtttgtccat ctaggtttct ttgttgtggc tgtgagctca     180
cttctcagtg cctctgctgt cactaacgct cctggagaaa tgaagaagga actgagactg     240
gcgggtggtg aaaacaactg tagtgggaga gtggaactta agatccatga caagtggggc     300
acagtgtgca gtaacggctg gagcatgaat gaagtgtccg tggtttgcca gcagctggga     360
tgcccaactt ctattaaagc ccttggatgg gctaactcca gcgccggctc tggatatatc     420
tggatggaca aagtttcttg tacagggaat gagtcagctc tttgggactg caaacatgat     480
gggtggggaa agcataactg tacccatgaa aaagatgctg gagtgacctg ctcagatgga     540
tctaatttgg agatgagact ggtgaacagt gcgggccacc gatgcttagg aagagtagaa     600
ataaagttcc agggaaagtg ggggacggtg tgtgacgaca acttcagcaa agatcacgct     660
tctgtgattt gtaaacagct tggatgtgga agtgccatta gtttctctgg ctcagctaaa     720
ttgggagctg gttctggacc aatctggctc gatgacctgg catgcaatgg aaatgagtca     780
gctctctggg actgcaaaca ccggggatgg ggcaagcata actgtgacca tgctgaggat     840
gtcggtgtga tttgcttaga gggagcagat ctgagcctga actagtggga tggagtgtcc     900
agatgttcag gaagattgga agtgagattc aaggagaat gggggaccgt gtgtgatgat     960
aactgggatc tccgggatgc ttctgtggtg tgcaagcaac tgggatgtcc aactgccatc    1020
agtgccattg gtcgagttaa tgccagtgag ggatctggac agatttggct tgacaacatt    1080
tcatgcgaag gacatgaggc aactctttgg gagtgtaaac accaagagtg gggaaagcat    1140
tactgtcatc atagagaaga cgctggtgtg acatgttctg atggagcaga tctggaactt    1200
agacttgtag gtgaggcag tcgctgtgct ggcattgtgg aggtggagat tcagaagctg    1260
actgggaaga tgtgtagccg aggctggaca ctggcagatg cggatgtggt ttgcagacag    1320
cttggatgtg gatctgcgct tcaaacccag gctaagatct actctaaaac tggggcaaca    1380
aatacgtggc tcttccctgg atcttgtaat ggaaatgaaa ctacttttg gcaatgcaaa    1440 aactggcagt ggggcggcct ttcctgtgat aatttcgaag aagccaaagt tacctgctca    1500
ggccacaggg aacccagact ggttggagga gaaatcccat gctctggtcg tgtggaagtg    1560
aaacacggag acgtgtgggg ctccgtctgt gatttgact tgtctctgga agctgccagt    1620
gtggtgtgca gggaattaca atgtggaaca gtcgtctcta tcctaggggg agcacatttt    1680
ggagaaggaa gtgacagat ctgggtgaa gaattccagt gtagtgggga tgagtcccat    1740
ctttcactat gctcagtggc gccccgcta gacagaactt gtacccacag cagggatgtc    1800
agcgtagtct gctcacgata catagatatt cgtctggcag gcgcgagtc ctcctgtgag    1860 ggaagagtgg agctcaagac actcggagcc tggggtcccc tctgcagttc tcattgggac    1920
atggaagatg ctcatgtctt atgtcagcag ctgaagtgtg gggttgccca atctattcca    1980
gaaggagcac attttgggaa aggagctggt caggtctgga gtcacatgtt ccactgcact    2040
ggaactgagg aacatatagg agattgcctc atgactgctc tgggtgcgcc gacgtgttcc    2100
gaaggacagg tggcctctgt catctgctca ggaaaccaat cccagacact attgccatgt    2160
```

-continued

```
agttcattgt ctccagtcca acaacaagc tctacaattc caaaggagag tgaagttccc    2220
tgcatagcaa gtggccagct tcgcttggta ggtggaggtg gtcgctgcgc tggaagagtg    2280
gaggtctgcc acgagggctc ttggggcacc gtctgtgatg acaattggga tatgactgat    2340
gccaatgtgg tgtgcaagca gctggactgt ggcgtggcaa ttaacgccac tggctctgct    2400
tacttcgggg aaggagcagg agctatctgg ctagacaagg tcatctgcac tgggaaagag    2460
tctcatattt ggcagtgcca ttacatggc tggggacgcc ataactgcag cacaaagaa     2520 gatgcaggtg ttatctgctc cgagttcatg tctctgaggc tgaccaacga agcccacaaa    2580
gaaaactgca caggtcgcct tgaagtgttt tacaatggta catggggcag tattggcagt    2640
agcaatatgt ctccaaccac tgtggggtg gtgtgccgtc agctgggctg gcagacaac     2700 gggactgtga aacccatacc ttcagacaag acaccatcca ggcccatgtg ggtagatcgt    2760
gtgcagtgtc caaaggagt tgacactttg tggcagtgcc cctcgtcacc ttggaaacag    2820
agacaggcca gccctcctc ccaggagtcc tggatcatct gtgacaacaa ataagactc      2880 caggaagggc atacagactg ttctggacgt gtggagatct ggcacaaagg ttcctgggga    2940
acagtgtgtg atgactcctg ggatcttaat gatgctaagg ttgtatgtaa gcagttgggc    3000
tgtggccaag ctgtgaaggc actaaaagaa gcagcatttg gtccaggaac tgggcccata    3060
tggctcaatg aaattaagtg tagagggaat gagtcttccc tgtgggattg tcctgccaaa    3120
ccgtggagtc acagcgactg tgggcacaaa gaagatgctt ccatccagtg cctcccaaaa    3180
atgacttcag aatcacatca tggcacaggt caccccaccc tcacggcact cttggttttgt    3240 ggagccattc tattggtcct cctcattgtc ttcctcctgt ggactctgaa gcgacgacgg    3300
attcagcgac ttacagtttc ctcaagagga gaggtcttga tacatcaagt tcagtaccaa    3360
gagatggatt caaaggcgga tgatctggac ttgctgaaat cctcgggggt cattcagagg    3420
cacactgaga aggaaaatga taattttataa tccactgagg ttggagttta agaagccttg    3480
acaggacagc cagctaaatg gaacaagagc ccaggcaacg cacggatgac cacagctgca    3540
tcttcatgca gtccttttgtt tcctggaact ctgctgaacc tgcaaaaacc atatttgtga    3600
atgtgaccac ttaatagaga tgggagactt ttgagggaat taaacaatat tgctattggt    3660
ttgcttgttc gcaataggg ctcattatgt atagccctgg agatggcgat agagagcagg    3720
caagcctaga attcacagag atctgcttgt ctctgcttcc caaatgctgg gatcaaatat    3780
gtggaccacc acatgtggtt taacaattgt gtcttgattt tataaatttc tggttggttt    3840
ttctgacgtt tttaggggttt cgtgaatata aaataatgtc ttttcggttg gcatgctaat    3900
ttttaaatat tatacacttc cttgtagtga gtttaagaat aatttcttat aaccaagtca    3960
attcattttc actttgaatt atttaataaa ggaatatggt cattgtgacc acacacacag    4020
cagttgtgac cgcctgtatg aggccttcaa aaaatatttt aaaaatagag ggctggagaa    4080
atggctcaga ggtcctgagt tcaattccta gcaaccacat ggtggctcac aaccatctgt    4140
aatgggaatc cgatgccctc ttccagtgta tctgaagata gtgacactgt cctcattaac    4200
ataaatataa taaataaatc tttaaaaaaa gaaaagacaa tagaggaggg gaggggcgtg    4260
agcgtaggag tgaggactga ttgagaagaa ggttggagga agtgggggga ggtgaaaagc    4320
tagttgggaa cttatgtgat cacagtgcat catgtccaaa tatgacatgt ccaaaaatgt    4380
tattaataaa gaaacggaaa tcaaa                                         4405
```

<210> SEQ ID NO 4
<211> LENGTH: 1121
<212> TYPE: PRT

<213> ORGANISM: Mus musculus
<300> PUBLICATION INFORMATION:
<308> DATABASE ACCESSION NUMBER: GenPept/AAK16065
<309> DATABASE ENTRY DATE: 2001-05-10
<313> RELEVANT RESIDUES IN SEQ ID NO: (1)..(1121)

<400> SEQUENCE: 4

```
Met Gly Gly His Arg Met Val Leu Leu Gly Ala Gly Ser Pro Gly
 1               5                  10                  15

Cys Lys Arg Phe Val His Leu Gly Phe Phe Val Val Ala Val Ser Ser
                20                  25                  30

Leu Leu Ser Ala Ser Ala Val Thr Asn Ala Pro Gly Glu Met Lys Lys
                35                  40                      45

Glu Leu Arg Leu Ala Gly Gly Glu Asn Asn Cys Ser Gly Arg Val Glu
 50                  55                  60

Leu Lys Ile His Asp Lys Trp Gly Thr Val Cys Ser Asn Gly Trp Ser
 65                  70                  75                  80

Met Asn Glu Val Ser Val Val Cys Gln Gln Leu Gly Cys Pro Thr Ser
                85                  90                  95

Ile Lys Ala Leu Gly Trp Ala Asn Ser Ser Ala Gly Ser Gly Tyr Ile
                100                 105                 110

Trp Met Asp Lys Val Ser Cys Thr Gly Asn Glu Ser Ala Leu Trp Asp
                115                 120                 125

Cys Lys His Asp Gly Trp Gly Lys His Asn Cys Thr His Glu Lys Asp
                130                 135                 140

Ala Gly Val Thr Cys Ser Asp Gly Ser Asn Leu Glu Met Arg Leu Val
145                 150                 155                 160

Asn Ser Ala Gly His Arg Cys Leu Gly Arg Val Glu Ile Lys Phe Gln
                165                 170                 175

Gly Lys Trp Gly Thr Val Cys Asp Asp Asn Phe Ser Lys Asp His Ala
                180                 185                 190

Ser Val Ile Cys Lys Gln Leu Gly Cys Gly Ser Ala Ile Ser Phe Ser
                195                 200                 205

Gly Ser Ala Lys Leu Gly Ala Gly Ser Gly Pro Ile Trp Leu Asp Asp
                210                 215                 220

Leu Ala Cys Asn Gly Asn Glu Ser Ala Leu Trp Asp Cys Lys His Arg
225                 230                 235                 240

Gly Trp Gly Lys His Asn Cys Asp His Ala Glu Asp Val Gly Val Ile
                245                 250                 255

Cys Leu Glu Gly Ala Asp Leu Ser Leu Arg Leu Val Ser Gly Val Ser
                260                 265                 270

Arg Cys Ser Gly Arg Leu Glu Val Arg Phe Gln Gly Glu Trp Gly Thr
                275                 280                 285

Val Cys Asp Asp Asn Trp Asp Leu Arg Asp Ala Ser Val Val Cys Lys
                290                 295                 300

Gln Leu Gly Cys Pro Thr Ala Ile Ser Ala Ile Gly Arg Val Asn Ala
305                 310                 315                 320

Ser Glu Gly Ser Gly Gln Ile Trp Leu Asp Asn Ile Ser Cys Glu Gly
                325                 330                 335

His Glu Ala Thr Leu Trp Glu Cys Lys His Gln Glu Trp Gly Lys His
                340                 345                 350

Tyr Cys His His Arg Glu Asp Ala Gly Val Thr Cys Ser Asp Gly Ala
                355                 360                 365

Asp Leu Glu Leu Arg Leu Val Gly Gly Ser Arg Cys Ala Gly Ile
                370                 375                 380
```

```
Val Glu Val Glu Ile Gln Lys Leu Thr Gly Lys Met Cys Ser Arg Gly
385                 390                 395                 400

Trp Thr Leu Ala Asp Ala Asp Val Val Cys Arg Gln Leu Gly Cys Gly
                405                 410                 415

Ser Ala Leu Gln Thr Gln Ala Lys Ile Tyr Ser Lys Thr Gly Ala Thr
            420                 425                 430

Asn Thr Trp Leu Phe Pro Gly Ser Cys Asn Gly Asn Glu Thr Thr Phe
        435                 440                 445

Trp Gln Cys Lys Asn Trp Gln Trp Gly Gly Leu Ser Cys Asp Asn Phe
    450                 455                 460

Glu Glu Ala Lys Val Thr Cys Ser Gly His Arg Glu Pro Arg Leu Val
465                 470                 475                 480

Gly Gly Glu Ile Pro Cys Ser Gly Arg Val Glu Val Lys His Gly Asp
                485                 490                 495

Val Trp Gly Ser Val Cys Asp Phe Asp Leu Ser Leu Glu Ala Ala Ser
            500                 505                 510

Val Val Cys Arg Glu Leu Gln Cys Gly Thr Val Val Ser Ile Leu Gly
        515                 520                 525

Gly Ala His Phe Gly Glu Gly Ser Gly Gln Ile Trp Gly Glu Glu Phe
    530                 535                 540

Gln Cys Ser Gly Asp Glu Ser His Leu Ser Leu Cys Ser Val Ala Pro
545                 550                 555                 560

Pro Leu Asp Arg Thr Cys Thr His Ser Arg Asp Val Ser Val Val Cys
                565                 570                 575

Ser Arg Tyr Ile Asp Ile Arg Leu Ala Gly Gly Glu Ser Ser Cys Glu
            580                 585                 590

Gly Arg Val Glu Leu Lys Thr Leu Gly Ala Trp Gly Pro Leu Cys Ser
        595                 600                 605

Ser His Trp Asp Met Glu Asp Ala His Val Leu Cys Gln Gln Leu Lys
    610                 615                 620

Cys Gly Val Ala Gln Ser Ile Pro Glu Gly Ala His Phe Gly Lys Gly
625                 630                 635                 640

Ala Gly Gln Val Trp Ser His Met Phe His Cys Thr Gly Thr Glu Glu
                645                 650                 655

His Ile Gly Asp Cys Leu Met Thr Ala Leu Gly Ala Pro Thr Cys Ser
            660                 665                 670

Glu Gly Gln Val Ala Ser Val Ile Cys Ser Gly Asn Gln Ser Gln Thr
        675                 680                 685

Leu Leu Pro Cys Ser Ser Leu Ser Pro Val Gln Thr Thr Ser Ser Thr
    690                 695                 700

Ile Pro Lys Glu Ser Glu Val Pro Cys Ile Ala Ser Gly Gln Leu Arg
705                 710                 715                 720

Leu Val Gly Gly Gly Gly Arg Cys Ala Gly Arg Val Glu Val Tyr His
                725                 730                 735

Glu Gly Ser Trp Gly Thr Val Cys Asp Asp Asn Trp Asp Met Thr Asp
            740                 745                 750

Ala Asn Val Val Cys Lys Gln Leu Asp Cys Gly Val Ala Ile Asn Ala
        755                 760                 765

Thr Gly Ser Ala Tyr Phe Gly Glu Gly Ala Gly Ala Ile Trp Leu Asp
    770                 775                 780

Glu Val Ile Cys Thr Gly Lys Glu Ser His Ile Trp Gln Cys His Ser
785                 790                 795                 800

His Gly Trp Gly Arg His Asn Cys Arg His Lys Glu Asp Ala Gly Val
                805                 810                 815
```

Ile Cys Ser Glu Phe Met Ser Leu Arg Leu Thr Asn Glu Ala His Lys
         820                 825                 830

Glu Ser Cys Thr Gly Arg Leu Glu Val Phe Tyr Asn Gly Thr Trp Gly
         835                 840                 845

Ser Ile Gly Ser Ser Asn Met Ser Pro Thr Thr Val Gly Val Val Cys
    850                 855                 860

Arg Gln Leu Gly Cys Ala Asp Asn Gly Thr Val Lys Pro Ile Pro Ser
865                 870                 875                 880

Asp Lys Thr Pro Ser Arg Pro Met Trp Val Asp Arg Val Gln Cys Pro
                 885                 890                 895

Lys Gly Val Asp Thr Leu Trp Gln Cys Pro Ser Ser Pro Trp Lys Gln
             900                 905                 910

Arg Gln Ala Ser Pro Ser Ser Gln Glu Ser Trp Ile Ile Cys Asp Asn
         915                 920                 925

Lys Ile Arg Leu Gln Glu Gly His Thr Asp Cys Ser Gly Arg Val Glu
    930                 935                 940

Ile Trp His Lys Gly Phe Trp Gly Thr Val Cys Asp Asp Ser Trp Asp
945                 950                 955                 960

Leu Asn Asp Ala Lys Val Val Cys Lys Gln Leu Gly Cys Gly Gln Ala
                 965                 970                 975

Val Lys Ala Leu Lys Glu Ala Ala Phe Gly Pro Gly Thr Gly Pro Ile
             980                 985                 990

Trp Leu Asn Glu Ile Lys Cys Arg Gly Asn Glu Ser Ser Leu Trp Asp
         995                1000                1005

Cys Pro Ala Lys Pro Trp Ser His Ser Asp Cys Gly His Lys Glu
   1010                1015                1020

Asp Ala Ser Ile Gln Cys Leu Pro Lys Met Thr Ser Glu Ser His
   1025                1030                1035

His Gly Thr Gly His Pro Thr Leu Thr Ala Leu Leu Val Cys Gly
   1040                1045                1050

Ala Ile Leu Leu Val Leu Leu Ile Val Phe Leu Leu Trp Thr Leu
   1055                1060                1065

Lys Arg Arg Gln Ile Gln Arg Leu Thr Val Ser Ser Arg Gly Glu
   1070                1075                1080

Val Leu Ile His Gln Val Gln Tyr Gln Glu Met Asp Ser Lys Ala
   1085                1090                1095

Asp Asp Leu Asp Leu Leu Lys Ser Ser Gly Val Ile Gln Arg His
   1100                1105                1110

Thr Glu Lys Glu Asn Asp Asn Leu
   1115                1120

<210> SEQ ID NO 5
<211> LENGTH: 3780
<212> TYPE: DNA
<213> ORGANISM: homo sapiens
<300> PUBLICATION INFORMATION:
<308> DATABASE ACCESSION NUMBER: GenBank/BC051281
<309> DATABASE ENTRY DATE: 2006-07-15
<313> RELEVANT RESIDUES IN SEQ ID NO: (1)..(3780)

<400> SEQUENCE: 5
aacatttcta gggaataata caagaagatt taggaatcat tgaagttata aatctttgga      60
atgagcaaac tcagaatggt gctacttgaa gactctggat ctgctgactt cagaagacat     120
tttgtcaact tgagtcccct caccattact gtggtcttac ttctcagtgc ctgttttgtc     180
accagttctc ttggaggaac agacaaggag ctgaggctag tggatggtga aaacaagtgt     240

```
agcgggagag tggaagtgaa agtccaggag gagtggggaa cggtgtgtaa taatggctgg    300
agcatggaag cggtctctgt gatttgtaac cagctgggat gtccaactgc tatcaaagcc    360
cctggatggg ctaattccag tgcaggttct ggacgcattt ggatggatca tgtttcttgt    420
cgtgggaatg agtcagctct ttgggattgc aaacatgatg gatgggaaa gcatagtaac     480 tgtactcacc aacaagatgc tggagtgacc tgctcagatg gatccaattt ggaaatgagg    540
ctgacgcgtg gagggaatat gtgttctgga agaatagaga tcaaattcca aggacggtgg    600
ggaacagtgt gtgatgataa cttcaacata gatcatgcat ctgtcatttg tagacaactt    660
gaatgtggaa gtgctgtcag tttctctggt tcatctaatt ttggagaagg ctctggacca    720
atctggtttg atgatcttat atgcaacgga atgagtcag ctctctggaa ctgcaaacat     780
caaggatggg gaaagcataa ctgtgatcat gctgaggatg ctggagtgat ttgctcaaag    840
ggagcagatc tgagcctgag actggtagat ggagtcactg aatgttcagg aagattagaa    900
gtgagattcc aaggagaatg ggggacaata tgtgatgacg gctgggacag ttacgatgct    960
gctgtggcat gcaagcaact gggatgtcca actgccgtca cagccattgg tcgagttaac   1020
gccagtaagg gatttggaca catctggctt gacagcgttt cttgccaggg acatgaacct   1080
gctgtctggc aatgtaaaca ccatgaatgg ggaaagcatt attgcaatca caatgaagat   1140
gctggcgtga catgttctga tggatcagat ctggagctaa gacttagagg tggaggcagc   1200
cgctgtgctg gacagttgaa ggtggagatt cagagactgt tagggaaggt gtgtgacaga   1260
ggctggggac tgaaagaagc tgatgtggtt tgcaggcagc tgggatgtgg atctgcactc   1320
aaaacatctt atcaagtgta ctccaaaatc caggcaacaa acacatggct gtttctaagt   1380
agctgtaacg gaaatgaaac ttctctttgg gactgcaaga actggcaatg gggtggactt   1440
acctgtgatc actatgaaga agccaaaatt acctgctcag cccacaggga acccagactg   1500 gttgagggg acattccctg ttctggacgt gttgaagtga gcatggtga cacgtggggc     1560 tccatctgtg attcggactt ctctctggaa gctgccagcg ttctatgcag ggaattacag   1620
tgtggcacag ttgtctctat cctggggga gctcactttg gagagggaaa tggacagatc    1680
tgggctgaag aattccagtg tgagggacat gagtcccatc tttcactctg cccagtagca   1740
ccccgcccag aaggaacttg tagccacagc agggatgttg gagtagtctg ctcaagatac   1800
acagaaattc gcttggtgaa tggcaagacc ccgtgtgagg gcagagtgga gctcaaaacg   1860
cttggtgcct ggggatccct ctgtaactct cactgggaca tagaagatgc ccatgttctt   1920
tgccagcagc ttaaatgtgg agttgcccct tctaccccag gaggagcacg ttttggaaaa   1980
ggaaatggtc agatctggag gcatatgttt cactgcactg ggactgagca gcacatggga   2040
gattgtcctg taactgctct aggtgcttca ttatgtcctt cagagcaagt ggcctctgta   2100
atctgctcag gaaaccagtc ccaaacactg tcctcgtgca attcatcgtc tttgggccca   2160
acaaggccta ccattccaga agaaagtgct gtggcctgca tagagagtgg tcaacttcgc   2220
ctggtaaatg gaggaggtcg ctgtgctggg agagtagaga tctatcatga gggctcctgg   2280
ggcaccatct gtgatgacag ctgggacctg agtgatgccc acgtggtttg cagacagctg   2340
ggctgtggag aggccattaa tgccactggt tctgctcatt ttgggaagg acagggccc     2400 atctggctga tgagatgaa atgcaatgga aagaatccc gcatttggca gtgccattca     2460
cacggctggg ggcagcaaaa ttgcaggcac aaggaggatg cgggagttat ctgctcagaa   2520
ttcatgtctc tgagactgac cagtgaagcc agcagagagg cctgtgcagg gcgtctggaa   2580
gttttttaca atggagcttg gggcactgtt ggcaagagta gcatgtctga aaccactgtg   2640
```

```
ggtgtggtgt gcaggcagct gggctgtgca gacaaaggga aaatcaaccc tgcatcttta    2700
gacaaggcca tgtccattcc catgtgggtg gacaatgttc agtgtccaaa aggacctgac    2760
acgctgtggc agtgcccatc atctccatgg gagaagagac tggccagccc tcggaggag     2820 acctggatca catgtgacaa caagataaga cttcaggaag acccacttc  ctgttctgga    2880 cgtgtggaga tctggcatgg aggttcctgg gggacagtgt tgatgactc  ttgggacttg    2940 gacgatgctc aggtggtgtg tcaacaactt ggctgtggtc cagctttgaa agcattcaaa    3000
gaagcagagt ttggtcaggg gactggaccg atatggctca atgaagtgaa gtgcaaaggg   3060
aatgagtctt ccttgtggga ttgtcctgcc agacgctggg gccatagtga gtgtgggcac   3120
aaggaagacg ctgcagtgaa ttgcacagat atttcagtgc agaaaacccc acaaaaagcc   3180
acaacaggtc gctcatcccg tcagtcatcc tttattgcag tcgggatcct tggggttgtt   3240
ctgttggcca ttttcgtcgc attattcttc ttgactaaaa agcgaagaca gagacagcgg   3300
cttgcagttt cctcaagagg agagaactta gtccaccaaa ttcaataccg ggagatgaat   3360
tcttgcctga atgcagatga tctggaccta atgaattcct cagaaaattc ccatgagtca   3420
gctgatttca gtgctgctga actaatttct gtgtctaaat tcttcctat  ttctggaatg   3480 gaaaaggagg ccattctgag ccacactgaa aaggaaaatg ggaatttata acccagtgag   3540
ttcagccttt aagataccct tgatgaagacc tggactattg aatggagcag aaattcacct   3600
ctctcactga ctattacagt tgcatttta  tggagttctt  cttctcctag gattcctaag   3660
actgctgctg aatttataaa aattaagttt gtgaatgtga ctacttagtg gtgtatatga   3720
gactttcaag ggaattaaat aaataaataa gaatgttatt gaaaaaaaaa aaaaaaaaa    3780
```

```
<210> SEQ ID NO 6
<211> LENGTH: 1156
<212> TYPE: PRT
<213> ORGANISM: HOMO SAPIENS
<300> PUBLICATION INFORMATION:
<308> DATABASE ACCESSION NUMBER: GenPept/AAH51281
<309> DATABASE ENTRY DATE: 2006-07-15
<313> RELEVANT RESIDUES IN SEQ ID NO: (1)..(1156)

<400> SEQUENCE: 6

Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
                20                  25                  30

Leu Leu Leu Ser Ala Cys Phe Val Thr Ser Ser Leu Gly Thr Asp
            35                  40                  45

Lys Glu Leu Arg Leu Val Asp Gly Glu Asn Lys Cys Ser Gly Arg Val
    50                  55                  60

Glu Val Lys Val Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Pro Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asn Leu Glu Met Arg
145                 150                 155                 160
```

```
Leu Thr Arg Gly Gly Asn Met Cys Ser Gly Arg Ile Glu Ile Lys Phe
            165                 170                 175
Gln Gly Arg Trp Gly Thr Val Cys Asp Asp Asn Phe Asn Ile Asp His
        180                 185                 190
Ala Ser Val Ile Cys Arg Gln Leu Glu Cys Gly Ser Ala Val Ser Phe
    195                 200                 205
Ser Gly Ser Ser Asn Phe Gly Glu Gly Ser Gly Pro Ile Trp Phe Asp
210                 215                 220
Asp Leu Ile Cys Asn Gly Asn Glu Ser Ala Leu Trp Asn Cys Lys His
225                 230                 235                 240
Gln Gly Trp Gly Lys His Asn Cys Asp His Ala Glu Asp Ala Gly Val
                245                 250                 255
Ile Cys Ser Lys Gly Ala Asp Leu Ser Leu Arg Leu Val Asp Gly Val
            260                 265                 270
Thr Glu Cys Ser Gly Arg Leu Glu Val Arg Phe Gln Gly Glu Trp Gly
        275                 280                 285
Thr Ile Cys Asp Asp Gly Trp Asp Ser Tyr Asp Ala Ala Val Ala Cys
    290                 295                 300
Lys Gln Leu Gly Cys Pro Thr Ala Val Thr Ala Ile Gly Arg Val Asn
305                 310                 315                 320
Ala Ser Lys Gly Phe Gly His Ile Trp Leu Asp Ser Val Ser Cys Gln
                325                 330                 335
Gly His Glu Pro Ala Val Trp Gln Cys Lys His His Glu Trp Gly Lys
            340                 345                 350
His Tyr Cys Asn His Asn Glu Asp Ala Gly Val Thr Cys Ser Asp Gly
        355                 360                 365
Ser Asp Leu Glu Leu Arg Leu Arg Gly Gly Ser Arg Cys Ala Gly
    370                 375                 380
Thr Val Glu Val Glu Ile Gln Arg Leu Leu Gly Lys Val Cys Asp Arg
385                 390                 395                 400
Gly Trp Gly Leu Lys Glu Ala Asp Val Val Cys Arg Gln Leu Gly Cys
                405                 410                 415
Gly Ser Ala Leu Lys Thr Ser Tyr Gln Val Tyr Ser Lys Ile Gln Ala
            420                 425                 430
Thr Asn Thr Trp Leu Phe Leu Ser Ser Cys Asn Gly Asn Glu Thr Ser
        435                 440                 445
Leu Trp Asp Cys Lys Asn Trp Gln Trp Gly Gly Leu Thr Cys Asp His
450                 455                 460
Tyr Glu Glu Ala Lys Ile Thr Cys Ser Ala His Arg Glu Pro Arg Leu
465                 470                 475                 480
Val Gly Gly Asp Ile Pro Cys Ser Gly Arg Val Glu Val Lys His Gly
                485                 490                 495
Asp Thr Trp Gly Ser Ile Cys Asp Ser Asp Phe Ser Leu Glu Ala Ala
            500                 505                 510
Ser Val Leu Cys Arg Glu Leu Gln Cys Gly Thr Val Val Ser Ile Leu
        515                 520                 525
Gly Gly Ala His Phe Gly Glu Gly Asn Gly Gln Ile Trp Ala Glu Glu
    530                 535                 540
Phe Gln Cys Glu Gly His Glu Ser His Leu Ser Leu Cys Pro Val Ala
545                 550                 555                 560
Pro Arg Pro Glu Gly Thr Cys Ser His Ser Arg Asp Val Gly Val Val
                565                 570                 575
Cys Ser Arg Tyr Thr Glu Ile Arg Leu Val Asn Gly Lys Thr Pro Cys
```

-continued

```
                580              585                590
Glu Gly Arg Val Glu Leu Lys Thr Leu Gly Ala Trp Gly Ser Leu Cys
            595                  600                 605

Asn Ser His Trp Asp Ile Glu Asp Ala His Val Leu Cys Gln Gln Leu
610                 615                 620

Lys Cys Gly Val Ala Leu Ser Thr Pro Gly Gly Ala Arg Phe Gly Lys
625                 630                 635                 640

Gly Asn Gly Gln Ile Trp Arg His Met Phe His Cys Thr Gly Thr Glu
            645                 650                 655

Gln His Met Gly Asp Cys Pro Val Thr Ala Leu Gly Ala Ser Leu Cys
            660                 665                 670

Pro Ser Glu Gln Val Ala Ser Val Ile Cys Ser Gly Asn Gln Ser Gln
            675                 680                 685

Thr Leu Ser Ser Cys Asn Ser Ser Leu Gly Pro Thr Arg Pro Thr
            690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
            725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
            755                 760                 765

Thr Gly Ser Ala His Phe Gly Glu Gly Thr Gly Pro Ile Trp Leu Asp
            770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
            805                 810                 815

Ile Cys Ser Glu Phe Met Ser Leu Arg Leu Thr Ser Glu Ala Ser Arg
            820                 825                 830

Glu Ala Cys Ala Gly Arg Leu Glu Val Phe Tyr Asn Gly Ala Trp Gly
            835                 840                 845

Thr Val Gly Lys Ser Ser Met Ser Glu Thr Thr Val Gly Val Val Cys
850                 855                 860

Arg Gln Leu Gly Cys Ala Asp Lys Gly Lys Ile Asn Pro Ala Ser Leu
865                 870                 875                 880

Asp Lys Ala Met Ser Ile Pro Met Trp Val Asp Asn Val Gln Cys Pro
            885                 890                 895

Lys Gly Pro Asp Thr Leu Trp Gln Cys Pro Ser Ser Pro Trp Glu Lys
            900                 905                 910

Arg Leu Ala Ser Pro Ser Glu Glu Thr Trp Ile Thr Cys Asp Asn Lys
            915                 920                 925

Ile Arg Leu Gln Glu Gly Pro Thr Ser Cys Ser Gly Arg Val Glu Ile
            930                 935                 940

Trp His Gly Gly Ser Trp Gly Thr Val Cys Asp Asp Ser Trp Asp Leu
945                 950                 955                 960

Asp Asp Ala Gln Val Val Cys Gln Gln Leu Gly Cys Gly Pro Ala Leu
            965                 970                 975

Lys Ala Phe Lys Glu Ala Glu Phe Gly Gln Gly Thr Gly Pro Ile Trp
            980                 985                 990

Leu Asn Glu Val Lys Cys Lys Gly Asn Glu Ser Ser Leu Trp Asp Cys
            995                1000                1005
```

-continued

| Pro | Ala | Arg | Arg | Trp | Gly | His | Ser | Glu | Cys | Gly | His | Lys | Glu | Asp |
|---|---|---|---|---|---|---|---|---|---|---|---|---|---|---|
| | 1010 | | | | 1015 | | | | 1020 | | | | | |

| Ala | Ala | Val | Asn | Cys | Thr | Asp | Ile | Ser | Val | Gln | Lys | Thr | Pro | Gln |
|---|---|---|---|---|---|---|---|---|---|---|---|---|---|---|
| 1025 | | | | | 1030 | | | | | 1035 | | | | |

| Lys | Ala | Thr | Thr | Gly | Arg | Ser | Ser | Arg | Gln | Ser | Ser | Phe | Ile | Ala |
|---|---|---|---|---|---|---|---|---|---|---|---|---|---|---|
| 1040 | | | | | 1045 | | | | | 1050 | | | | |

| Val | Gly | Ile | Leu | Gly | Val | Val | Leu | Leu | Ala | Ile | Phe | Val | Ala | Leu |
|---|---|---|---|---|---|---|---|---|---|---|---|---|---|---|
| 1055 | | | | | 1060 | | | | | 1065 | | | | |

| Phe | Phe | Leu | Thr | Lys | Lys | Arg | Arg | Gln | Arg | Gln | Arg | Leu | Ala | Val |
|---|---|---|---|---|---|---|---|---|---|---|---|---|---|---|
| 1070 | | | | | 1075 | | | | | 1080 | | | | |

| Ser | Ser | Arg | Gly | Glu | Asn | Leu | Val | His | Gln | Ile | Gln | Tyr | Arg | Glu |
|---|---|---|---|---|---|---|---|---|---|---|---|---|---|---|
| 1085 | | | | | 1090 | | | | | 1095 | | | | |

| Met | Asn | Ser | Cys | Leu | Asn | Ala | Asp | Asp | Leu | Asp | Leu | Met | Asn | Ser |
|---|---|---|---|---|---|---|---|---|---|---|---|---|---|---|
| 1100 | | | | | 1105 | | | | | 1110 | | | | |

| Ser | Glu | Asn | Ser | His | Glu | Ser | Ala | Asp | Phe | Ser | Ala | Ala | Glu | Leu |
|---|---|---|---|---|---|---|---|---|---|---|---|---|---|---|
| 1115 | | | | | 1120 | | | | | 1125 | | | | |

| Ile | Ser | Val | Ser | Lys | Phe | Leu | Pro | Ile | Ser | Gly | Met | Glu | Lys | Glu |
|---|---|---|---|---|---|---|---|---|---|---|---|---|---|---|
| 1130 | | | | | 1135 | | | | | 1140 | | | | |

| Ala | Ile | Leu | Ser | His | Thr | Glu | Lys | Glu | Asn | Gly | Asn | Leu |
|---|---|---|---|---|---|---|---|---|---|---|---|---|
| 1145 | | | | | 1150 | | | | | 1155 | | |

<210> SEQ ID NO 7
<211> LENGTH: 4950
<212> TYPE: DNA
<213> ORGANISM: homo sapiens
<300> PUBLICATION INFORMATION:
<308> DATABASE ACCESSION NUMBER: GenBank/Z22970
<309> DATABASE ENTRY DATE: 2005-04-18
<313> RELEVANT RESIDUES IN SEQ ID NO: (1)..(4950)

<400> SEQUENCE: 7

```
gaattcttag ttgttttctt tagaagaaca tttctaggga ataatacaag aagatttagg      60
aatcattgaa gttataaatc tttggaatga gcaaactcag aatggtgcta cttgaagact     120
ctggatctgc tgacttcaga agacattttg tcaacctgag tcccttcacc attactgtgg     180
tcttacttct cagtgcctgt tttgtcacca gttctcttgg aggaacagac aaggagctga     240
ggctagtgga tggtgaaaac aagtgtagcg ggagagtgga agtgaaagtc caggaggagt     300
ggggaacggt gtgtaataat ggctggagca tggaagcggt ctctgtgatt tgtaaccagc     360
tgggatgtcc aactgctatc aaagcccctg gatgggctaa ttccagtgca ggttctggac     420
gcatttggat ggatcatgtt tcttgtcgtg ggaatgagtc agctctttgg gattgcaaac     480
atgatggatg ggaaagcat agtaactgta ctcaccaaca agatgctgga gtgacctgct     540
cagatggatc caatttggaa atgaggctga cgcgtggagg gaatatgtgt tctggaagaa     600
tagagatcaa attccaagga cggtggggaa cagtgtgtga tgataacttc aacatagatc     660
atgcatctgt catttgtaga caacttgaat gtggaagtgc tgtcagtttc tctggttcat     720
ctaattttgg agaaggctct ggaccaatct ggtttgatga tcttatatgc aacggaaatg     780
agtcagctct ctggaactgc aaacatcaag gatggggaaa gcataactgt gatcatgctg     840
aggatgctgg agtgatttgc tcaaagggag cagatctgag cctgagactg gtagatggag     900
tcactgaatt ccaggaaga ttagaagtga gattccaagg agaatggggg acaatatgtg     960
atgacggctg ggacagttac gatgctgctg tggcatgcaa gcaactggga tgtccaactg    1020
ccgtcacagc cattggtcga gttaacgcca gtaagggatt tggacacatc tggcttgaca    1080
gcgtttcttg ccaggacat gaacctgctg tctggcaatg taaacaccat gaatggggaa    1140
```

```
agcattattg caatcacaat gaagatgctg gcgtgacatg ttctgatgga tcagatctgg    1200
agctaagact tagaggtgga ggcagccgct gtgctgggac agttgaggtg gagattcaga    1260
gactgttagg gaaggtgtgt gacagaggct ggggactgaa agaagctgat gtggtttgca    1320
ggcagctggg atgtggatct gcactcaaaa catcttatca agtgtactcc aaaatccagg    1380
caacaaacac atggctgttt ctaagtagct gtaacggaaa tgaaacttct ctttgggact    1440
gcaagaactg gcaatggggt ggacttacct gtgatcacta tgaagaagcc aaaattacct    1500
gctcagccca cagggaaccc agactggttg gaggggacat tccctgttct ggacgtgttg    1560
aagtgaagca tggtgacacg tggggctcca tctgtgattc ggacttctct ctggaagctg    1620
ccagcgttct atgcagggaa ttacagtgtg gcacagttgt ctctatcctg ggggagctc    1680 actttggaga gggaaatgga cagatctggg ctgaagaatt ccagtgtgag ggacatgagt    1740
cccatctttc actctgccca gtagcacccc gcccagaagg aacttgtagc cacagcaggg    1800
atgttggagt agtctgctca agatacacag aaattcgctt ggtgaatggc aagacccgt    1860 gtgagggcag agtggagctc aaaacgcttg gtgcctgggg atccctctgt aactctcact    1920
gggacataga agatgcccat gttctttgcc agcagcttaa atgtggagtt gccctttcta    1980
ccccaggagg agcacgtttt ggaaaaggaa atggtcagat ctggaggcat atgtttcact    2040
gcactgggac tgagcagcac atgggagatt gtcctgtaac tgctctaggt gcttcattat    2100
gtccttcaga gcaagtggcc tctgtaatct gctcaggaaa ccagtcccaa acactgtcct    2160
cgtgcaattc atcgtctttg ggcccaacaa ggcctaccat tccagaagaa agtgctgtgg    2220
cctgcataga gagtggtcaa cttcgcctgg taaatggagg aggtcgctgt gctgggagag    2280
tagagatcta tcatgagggc tcctgggggca ccatctgtga tgacagctgg gacctgagtg    2340
atgcccacgt ggtttgcaga cagctgggct gtggagaggc cattaatgcc actggttctg    2400 ctcatttttgg ggaaggaaca gggcccatct ggctggatga gatgaaatgc aatggaaaag    2460
aatcccgcat ttggcagtgc cattcacacg gctggggca gcaaaattgc aggcacaagg    2520
aggatgcggg agttatctgc tcagaattca tgtctctgag actgaccagt gaagccagca    2580
gagaggcctg tgcagggcgt ctggaagttt tttacaatgg agcttggggc actgttggca    2640
agagtagcat gtctgaaacc actgtgggtg tggtgtgcag gcagctgggc tgtgcagaca    2700
aagggaaaat caaccctgca tctttagaca aggccatgtc cattcccatg tgggtggaca    2760
atgttcagtg tccaaaagga cctgacacgc tgtggcagtg cccatcatct ccatgggaga    2820
agagactggc cagcccctcg gaggagacct ggatcacatg tgacaacaag ataagacttc    2880
aggaaggacc cacttcctgt tctggacgtg tggagatctg gcatggaggt tcctggggga    2940
cagtgtgtga tgactcttgg gacttggacg atgctcaggt ggtgtgtcaa caacttggct    3000
gtggtccagc tttgaaagca ttcaaagaag cagagtttgg tcaggggact ggaccgatat    3060
ggctcaatga agtgaagtgc aaagggaatg agtcttcctt gtgggattgt cctgccagac    3120
gctggggcca tagtgagtgt gggcacaagg aagacgctgc agtgaattgc acagatattt    3180
cagtgcagaa aacccacaa aaagccacaa caggtcgctc atcccgtcag tcatcccttta    3240 ttgcagtcgg gatccttggg gttgttctgt tggccatttt cgtcgcatta ttcttcttga    3300
ctaaaaagcg aagacagaga cagcggcttg cagtttcctc aagaggagag aacttagtcc    3360
accaaattca ataccgggag atgaattctt gcctgaatgc agatgatctg gacctaatga    3420
attcctcagg tctgtgggtt cttggagggt ctattgccca gggggtcaga tcagtggctg    3480
cagttgaggc acagacattc tactttgata aacagttaaa aaagtctaaa aatgtaatag    3540
```

```
gaagcttaga tgcatataat ggacaagaat gactgaaaat tattcttgga gaatatcaaa    3600
attgcaatca tagggaggcc tttagctaaa gaggcctgtg attattcctg atagaggtat    3660
ggaaagaacc atgcagagga atattatgac ttggacctca ttttattaaa acagaaatta    3720
atcttacaaa agattgtcat aagtgacagt ttaactttt tctttaaatt ttgttgtgta    3780
tatttaaggt atacaacatg atttatggg atgtatatag atagtaaaaa gcttactaaa    3840
gcaaagcaaa tgaacacacc catcatctga catagttacc cttttttgtg ttgttcttgt    3900
ggcaagagca gctaaaacct actcacttag catgaatcct acatacagca caatgttatt    3960
acctataatc ctcatgttgt acattagacc tctagactgg ttcattctac gtatctgcta    4020
ctttgtatcc tctgacctac atacgtcttt cacagtttct tccattccca tttcctgtca    4080
tttttttct ctagcttgat atttattata ttttcccta aaagtctaaa acctaaaact    4140
ttcaatatct ttattgcatg agaagccata caaatccaca gaactagcct tatttctcat    4200
cacatcatgc tgttttatcc ttgaacttct atttagcacc agtgcactaa ttctgcatct    4260
gggcaggatg actttactgg gttggaagaa atatcccaaa acccattgtc tttactccat    4320
gaagggtccc tgaccttctg agaggggcct gcctcacttc ttccatccaa agaattatgc    4380
atctgctact gtgtcaggga acatatttaa ggaacatgta ctgttactgt gtcaggaaac    4440
atatttaaga aataggaaag actttctctg ccccttaaat cacacatgct tttcttccta    4500
gttatgggtg gtgttttag ttgctcaaag agcctcacag ttacgtgaga agaggtctgg    4560
tttatttccc agtaattatt ttcttccttt cagaaaattc ccatgagtca gctgatttca    4620
gtgctgctga actaatttct gtgtctaaat ttcttcctat ttctggaatg gaaaaggagg    4680
ccattctgag ccacactgaa aaggaaaatg ggaatttata acccagtgag ttcagccttt    4740
aagatacctt gatgaagacc tggactattg aatggagcag aaattcacct ctctcactga    4800
ctattacagt tgcattttta tggagttctt cttctcctag gattcctaag actgctgctg    4860
aatttataaa aattaagttt gtgaatgtga ctacttagtg gtgtatatga gactttcaag    4920
ggaattaaat aaataaataa gaatgttaaa                                      4950
```

<210> SEQ ID NO 8
<211> LENGTH: 1156
<212> TYPE: PRT
<213> ORGANISM: HOMO SAPIENS
<300> PUBLICATION INFORMATION:
<308> DATABASE ACCESSION NUMBER: GenPept/CAA80543
<309> DATABASE ENTRY DATE: 2005-04-18
<313> RELEVANT RESIDUES IN SEQ ID NO: (1)..(1156)

<400> SEQUENCE: 8

```
Met Val Leu Leu Glu Asp Ser Gly Ser Ala Asp Phe Arg Arg His Phe
1               5                   10                  15

Val Asn Leu Ser Pro Phe Thr Ile Thr Val Leu Leu Leu Ser Ala
            20                  25                  30

Cys Phe Val Thr Ser Ser Leu Gly Gly Thr Asp Lys Glu Leu Arg Leu
        35                  40                  45

Val Asp Gly Glu Asn Lys Cys Ser Gly Arg Val Glu Val Lys Val Gln
    50                  55                  60

Glu Glu Trp Gly Thr Val Cys Asn Asn Gly Trp Ser Met Glu Ala Val
65                  70                  75                  80

Ser Val Ile Cys Asn Gln Leu Gly Cys Pro Thr Ala Ile Lys Ala Pro
                85                  90                  95

Gly Trp Ala Asn Ser Ser Ala Gly Ser Gly Arg Ile Trp Met Asp His
            100                 105                 110
```

Val Ser Cys Arg Gly Asn Glu Ser Ala Leu Trp Asp Cys Lys His Asp
            115                 120                 125

Gly Trp Gly Lys His Ser Asn Cys Thr His Gln Gln Asp Ala Gly Val
    130                 135                 140

Thr Cys Ser Asp Gly Ser Asn Leu Glu Met Arg Leu Thr Arg Gly Gly
145                 150                 155                 160

Asn Met Cys Ser Gly Arg Ile Glu Ile Lys Phe Gln Gly Arg Trp Gly
                165                 170                 175

Thr Val Cys Asp Asp Asn Phe Asn Ile Asp His Ala Ser Val Ile Cys
            180                 185                 190

Arg Gln Leu Glu Cys Gly Ser Ala Val Ser Phe Ser Gly Ser Ser Asn
        195                 200                 205

Phe Gly Glu Gly Ser Gly Pro Ile Trp Phe Asp Leu Ile Cys Asn
    210                 215                 220

Gly Asn Glu Ser Ala Leu Trp Asn Cys Lys His Gln Gly Trp Gly Lys
225                 230                 235                 240

His Asn Cys Asp His Ala Glu Asp Ala Gly Val Ile Cys Ser Lys Gly
                245                 250                 255

Ala Asp Leu Ser Leu Arg Leu Val Asp Gly Val Thr Glu Cys Ser Gly
            260                 265                 270

Arg Leu Glu Val Arg Phe Gln Gly Glu Trp Gly Thr Ile Cys Asp Asp
        275                 280                 285

Gly Trp Asp Ser Tyr Asp Ala Ala Val Ala Cys Lys Gln Leu Gly Cys
    290                 295                 300

Pro Thr Ala Val Thr Ala Ile Gly Arg Val Asn Ala Ser Lys Gly Phe
305                 310                 315                 320

Gly His Ile Trp Leu Asp Ser Val Ser Cys Gln Gly His Glu Pro Ala
                325                 330                 335

Val Trp Gln Cys Lys His His Glu Trp Gly Lys His Tyr Cys Asn His
            340                 345                 350

Asn Glu Asp Ala Gly Val Thr Cys Ser Asp Gly Ser Asp Leu Glu Leu
        355                 360                 365

Arg Leu Arg Gly Gly Ser Arg Cys Ala Gly Thr Val Glu Val Glu
    370                 375                 380

Ile Gln Arg Leu Leu Gly Lys Val Cys Asp Arg Gly Trp Gly Leu Lys
385                 390                 395                 400

Glu Ala Asp Val Val Cys Arg Gln Leu Gly Cys Gly Ser Ala Leu Lys
                405                 410                 415

Thr Ser Tyr Gln Val Tyr Ser Lys Ile Gln Ala Thr Asn Thr Trp Leu
            420                 425                 430

Phe Leu Ser Ser Cys Asn Gly Asn Glu Thr Ser Leu Trp Asp Cys Lys
        435                 440                 445

Asn Trp Gln Trp Gly Gly Leu Thr Cys Asp His Tyr Glu Glu Ala Lys
    450                 455                 460

Ile Thr Cys Ser Ala His Arg Glu Pro Arg Leu Val Gly Gly Asp Ile
465                 470                 475                 480

Pro Cys Ser Gly Arg Val Glu Val Lys His Gly Asp Thr Trp Gly Ser
                485                 490                 495

Ile Cys Asp Ser Asp Phe Ser Leu Glu Ala Ala Ser Val Leu Cys Arg
            500                 505                 510

Glu Leu Gln Cys Gly Thr Val Val Ser Ile Leu Gly Gly Ala His Phe
        515                 520                 525

Gly Glu Gly Asn Gly Gln Ile Trp Ala Glu Glu Phe Gln Cys Glu Gly

```
                530                535                540
His Glu Ser His Leu Ser Leu Cys Pro Val Ala Pro Arg Pro Glu Gly
545                550                555                560

Thr Cys Ser His Ser Arg Asp Val Gly Val Cys Ser Arg Tyr Thr
            565                570                575

Glu Ile Arg Leu Val Asn Gly Lys Thr Pro Cys Glu Gly Arg Val Glu
            580                585                590

Leu Lys Thr Leu Gly Ala Trp Gly Ser Leu Cys Asn Ser His Trp Asp
            595                600                605

Ile Glu Asp Ala His Val Leu Cys Gln Gln Leu Lys Cys Gly Val Ala
            610                615                620

Leu Ser Thr Pro Gly Gly Ala Arg Phe Gly Lys Gly Asn Gly Gln Ile
625                630                635                640

Trp Arg His Met Phe His Cys Thr Gly Thr Glu Gln His Met Gly Asp
            645                650                655

Cys Pro Val Thr Ala Leu Gly Ala Ser Leu Cys Pro Ser Glu Gln Val
            660                665                670

Ala Ser Val Ile Cys Ser Gly Asn Gln Ser Gln Thr Leu Ser Ser Cys
            675                680                685

Asn Ser Ser Leu Gly Pro Thr Arg Pro Thr Ile Pro Glu Glu Ser
690                695                700

Ala Val Ala Cys Ile Glu Ser Gly Gln Leu Arg Leu Val Asn Gly Gly
705                710                715                720

Gly Arg Cys Ala Gly Arg Val Glu Ile Tyr His Glu Gly Ser Trp Gly
            725                730                735

Thr Ile Cys Asp Asp Ser Trp Asp Leu Ser Asp Ala His Val Val Cys
            740                745                750

Arg Gln Leu Gly Cys Gly Glu Ala Ile Asn Ala Thr Gly Ser Ala His
            755                760                765

Phe Gly Glu Gly Thr Gly Pro Ile Trp Leu Asp Glu Met Lys Cys Asn
770                775                780

Gly Lys Glu Ser Arg Ile Trp Gln Cys His Ser His Gly Trp Gly Gln
785                790                795                800

Gln Asn Cys Arg His Lys Glu Asp Ala Gly Val Ile Cys Ser Glu Phe
            805                810                815

Met Ser Leu Arg Leu Thr Ser Glu Ala Ser Arg Glu Ala Cys Ala Gly
            820                825                830

Arg Leu Glu Val Phe Tyr Asn Gly Ala Trp Gly Thr Val Gly Lys Ser
            835                840                845

Ser Met Ser Glu Thr Thr Val Gly Val Val Cys Arg Gln Leu Gly Cys
850                855                860

Ala Asp Lys Gly Lys Ile Asn Pro Ala Ser Leu Asp Lys Ala Met Ser
865                870                875                880

Ile Pro Met Trp Val Asp Asn Val Gln Cys Pro Lys Gly Pro Asp Thr
            885                890                895

Leu Trp Gln Cys Pro Ser Ser Pro Trp Glu Lys Arg Leu Ala Ser Pro
            900                905                910

Ser Glu Glu Thr Trp Ile Thr Cys Asp Asn Lys Ile Arg Leu Gln Glu
            915                920                925

Gly Pro Thr Ser Cys Ser Gly Arg Val Glu Ile Trp His Gly Gly Ser
930                935                940

Trp Gly Thr Val Cys Asp Asp Ser Trp Asp Leu Asp Asp Ala Gln Val
945                950                955                960
```

```
Val Cys Gln Gln Leu Gly Cys Gly Pro Ala Leu Lys Ala Phe Lys Glu
            965                 970                 975

Ala Glu Phe Gly Gln Gly Thr Gly Pro Ile Trp Leu Asn Glu Val Lys
            980                 985                 990

Cys Lys Gly Asn Glu Ser Ser Leu  Trp Asp Cys Pro Ala  Arg Arg Trp
            995                1000                1005

Gly His  Ser Glu Cys Gly  His  Lys Glu Asp Ala Ala  Val Asn Cys
            1010                1015                1020

Thr Asp  Ile Ser Val Gln Lys  Thr Pro Gln Lys Ala   Thr Thr Gly
            1025                1030                1035

Arg Ser  Ser Arg Gln Ser  Ser  Phe Ile Ala Val Gly  Ile Leu Gly
            1040                1045                1050

Val Val  Leu Leu Ala Ile Phe  Val Ala Leu Phe  Phe  Leu Thr Lys
            1055                1060                1065

Lys Arg  Arg Gln Arg Gln Arg  Leu Ala Val Ser Ser   Arg Gly Glu
            1070                1075                1080

Asn Leu  Val His Gln Ile Gln  Tyr Arg Glu Met Asn   Ser Cys Leu
            1085                1090                1095

Asn Ala  Asp Asp Leu Asp Leu  Met Asn Ser Ser Gly   Leu Trp Val
            1100                1105                1110

Leu Gly  Gly Ser Ile Ala Gln  Gly Phe Arg Ser Val  Ala Ala Val
            1115                1120                1125

Glu Ala  Gln Thr Phe Tyr Phe  Asp Lys Gln Leu Lys   Lys Ser Lys
            1130                1135                1140

Asn Val  Ile Gly Ser Leu Asp  Ala Tyr Asn Gly Gln   Glu
            1145                1150                1155

<210> SEQ ID NO 9
<211> LENGTH: 5193
<212> TYPE: DNA
<213> ORGANISM: sus scrofa
<300> PUBLICATION INFORMATION:
<308> DATABASE ACCESSION NUMBER: GenBank/NM_214346
<309> DATABASE ENTRY DATE: 2004-08-05
<313> RELEVANT RESIDUES IN SEQ ID NO: (1)..(5193)

<400> SEQUENCE: 9
atggacttcc tgctcctgct cctcctcctg gcttcatctg ctctagcagg cctggcctcg      60
tggacggttt ccagccccga gaccgtgcag ggcatcaagg gctcctgcct catcatcccc     120
tgcaccttcg gcttcccggc caacgtggag gtgccccatg gcatcacagc catctggtac     180
tatgactact caggcaagcg cctggtagtg agccactcca ggaacccaaa ggtggtggag     240
aaccacttcc aaggccgggc cctgctgttg gggcaggttg aacagaggac gtgcagcctg     300
ctgctgaagg acctgcagcc ccaggactcg ggctcctata acttccgctt tgagatcagc     360
gagggcaacc gctggtcaga tgtcaaaggc acagttgtca ccgtgacaga ggtgcccagc     420
gtgcccacca ttgccttgcc agccaagctg catgagggca tggaggtgga cttcaactgc     480
tccactccct atgtgtgccc gacggagccg tcaacctac agtggcaagg ccaggatccc     540
acccgctccg tcacctccca cctccagaag cttgagccct cggcaccag ccacatggag     600 accctgcaca tggccctgtc ctggcaggac catggccgga tcctgagctg ccaggtctca     660
gcagccgaac gcaggatgca gaaggagatt cacctccaag tgcagtatgc ccccaagggt     720
gtggagatcc ttttcagcca ctccggacgg aacgtccttc caggtgatct ggtcaccctc     780
agctgccagg tgaatagcag caaccctcag gtcagttccg tgcagtgggt caaggatggg     840
acgaagctca aagaccagaa acgtgtactg cagttgcgcc gggcagcctg gctgatgct     900
```

```
ggcgtctaca cctgccaagc cgggaatgcc gtgggctctt cagtctcacc cccggtcagc    960
ctccacgtct tcatggctga ggtccaggta agccctgtgg gctccatcct ggagaaccag   1020
acggtgacgc tggcctgcaa tacacctaag gaagcgccca gcgagctgcg ctacagctgg   1080
tacaagaacc acgccctgct ggagggctct cacagccgca ccctccggct gcactcagtt   1140
accagggcgg attcgggctt ctacttctgc gaggtgcaga acgcccgggg cagagagcgc   1200
tctcccctg tcagcgtggt ggtcagccac ccaccctca ccccggacct aactgccttc   1260
ctggagacac aggcggggct ggtgggcatc ctccaatgct ctgtggtcag cgagcccca   1320
gctactctgg tgttgtcaca cggggggcctc atcttggcct ctacctccgg ggagggtgac   1380
cacagcccac gcttcagtgt cgcctctgcc cccaactccc tgcgcctgga gattcaagac   1440
ctggggccaa cagacagtgg ggaatacatg tgctcagcca gcagttctct tgggaatgcg   1500
tcctccaccc tggacttcca tgccaatgca gcccgcctcc tcatcagccc agcagcagag   1560
gtggtggaag gcaggcggt gacactgagc tgcaggagca gcctgagcct gatgcctgac   1620
acccgttttt cctggtacct gaacggggcc ctgattctcg aggggccag cagcagcctc   1680
ctgctcccag cagcctccag cacagatgcc ggctcatacc actgccgggc ccagaacagc   1740
cacagcacca gcgggccctc ctcacctgct gttctcaccg tgctctacgc cccacgccag   1800
cccgtgttca ctgcccagct ggaccctgat actgcaggag ctggggccgg acgccaaggc   1860
ctcctcttgt gccgtgtgga cagcgacccc ccagcccagc tgcagctgct ccacaggggc   1920
cgtgttgtgg cctcttctct gtcatggggg ggcggctgct gcacctgcgg aggctgtttc   1980
caccgcatga aggtcaccaa agcacccaac ctactgcgtg tagagatccg agacccggtg   2040
ctggaggatg agggtgtgta cctgtgcgag gccagcagcg ccctgggcaa cgcctccgcc   2100
tctgcaacct tggatgccca ggccactgtc ctggtcatca caccgtcaca cacgctgcag   2160
gaaggcattg aagccaacct gacttgcaac gtgagccgtg aagccagcgg ccctgccaac   2220
ttctcctggt ccgagatggg ggcgctatgg gccagggcc tctggacac cgtgacgctg   2280
ctacctgtgg ccagaactga tgctgccctc tatgcttgcc gcatcgtcac cgaggctggt   2340
gctggcctct ccacccctgt ggccctgaat gtgctctatc ccccgatcc tccaaagttg   2400
tcagccctcc tggacgtgga ccagggccac acggctgtgt tcgtctgtac tgtgacagt   2460
cgccctcttg cccagttggc cctgttccgt ggggaacacc tcctggccgc cagctcggca   2520
ctccggctcc cccctcgtgg ccgctccag gccaaagcct cggccaactc cttgcagcta   2580
gaggtccgag acttgagcct tggggactct ggcagctacc actgtgaggc caccaacatc   2640
cttggatcag ccaacacttc tcttaccttc caggtccgag gagcctgggt ccgggtgtca   2700
ccgtcgcctg agctccagga gggccaggct gtggtcctga gctgccaggt acccataggg   2760
gtcctggagg ggacctcata tcgttggtat cgggatggcc agcccctcca ggagtccact   2820
tcggccacgc tccgttttgc agccataact ctgagccagg ctggagccta ccattgccaa   2880
gcccaagctc caggctcagc caccacggac ctggctgccc ctgtcagcct ccacgtgacc   2940
tacgcacctc gccaggccac actcaccacc ctgatggact caggcctcgg gcgactgggc   3000
ctccttctgt gccgtgtgaa cagtgaccct cctgcccagc tccgactgct ccatgggagc   3060
cgcctcgtgg cctctactct acaaggtgtg gaggagcttg caggcagctc tccccgccta   3120
caggtggcca cagcccccaa cacgctgcgc ctggagatca caacgcagt gctggaggat   3180
gaaggcgtct acacctgcga ggccaccaac acctgggtc agaccttggc ctccgccgcc   3240
ttcgatgccc aggctatgag agtgcaggtg tggcccaatg ccaccgtgca agaggggcag   3300
```

```
ctggtgaacc tgacctgcct tgtatggacc acgcacctgg cccagctcac ctacacgtgg    3360
taccgagacc agcagcagct cccaggtgct gcccactcca tcctcctgcc caatgtcact    3420
gtcacagatg ccgcctccta ccgctgtggc atattgatcc ctggccaggc actccgcctc    3480
tccagacctg tcgccctgga tgtcctctac gcaccccgca gactgcgcct gacccatctc    3540
ttggagagcc gtggtgggca gctggccgtg tgtctgtgca ctgtggacag tcgcccagct    3600
gcccagctga ccctcagcca tgctggccgc ctcctggcct cctcaaccgc agcctctgtc    3660
cccaacaccc tgcgcctgga gctgtgggag ccccggccca gtgatgaggg tctctacagc    3720
tgctcggccc gcagtcctct gggccaggcc aacacatccc tggagctgcg gctagagggc    3780
gtgcaggtgg cactggctcc atcggccact gtgccggagg gggcccctgt cacagtgacc    3840
tgtgaagacc ctgctgcccg cccacccact ctctatgtct ggtaccacaa cagccgttgg    3900
ctgcaggagg ggtcggctgc ctccctctcg tttccagcgg ctacacgggc tcacgcgggc    3960
gcctatacct gccaggtcca ggatgcccag ggcacacgca tctcccagcc cgcagcactg    4020
cacatcctct atgcccctcg ggatgctgtc ctttcctcct tctgggactc aagggccagc    4080
cctatggccg tggtacagtg cactgtggac agcgagccac tgccgagat gaccctgtcc    4140 catgatggca aggtgctggc caccagccat ggggtccacg gcttagcagt ggggacaggc    4200
catgtccagg tggcccgcaa cgccctgcag ctgcgggtgc agaatgtgcc ctcacgtgac    4260
aaggacacct acgtctgcat ggaccgcaac tccttgggct cagtcagcac catggggcag    4320
ctgcagccag aaggtgtgca cgtggtagct gagccagggc tggatgtgcc tgaaggcaca    4380
gcgctgaacc tgagctgtcg cctccctagt ggccctgggc acataggcaa ctccaccttt    4440
gcttggttcc ggaacggtcg gcagctacac acagagtctg tgcccaccct taccttcacc    4500
catgtggccc gcgcccaagc tggcttgtac cactgccagg ctgagctccc cgccggggct    4560
gccacctctg ctccagtctt gctccgggtg ctctaccctc ccaagacgcc caccatgact    4620
gtttttgtgg agcccgaggg tggcatccag ggcattctgg actgccgagt ggacagtgag    4680
cccctagcca gcctgaccct ccacctgggc agtcggctgg tggcctccag ccagcctcag    4740
gctgcccctg ccaagccgca catccgcgtc tcagccagtc ccaatgcctt gcgagtggac    4800
atggaggagc tgaagcccag tgaccagggg gagtatgtgt gctcggcctc caatgccctg    4860
ggctctgcct ctgctgccac ctacttcgga accagagccc tgcatcgcct gcatctgttc    4920
cagcaccttc tctggttcct ggggctgctg gcgagcctcc tcttcctact gttgggcctg    4980
ggggtctggt acgcctggag acggggaaat ttttacaagc tgagaatggg cgaatattca    5040
gtagagatgg tatctcggaa ggaaaccacg cagatgtcca ctgaccagga agaagttact    5100
ggaatcggtg atgatgcggg ctctgtgaac caggcggcat ttgatcctgc ccacctctgt    5160
gaaaacacac agtctgtgaa aagcacagtc tga                                 5193
```

<210> SEQ ID NO 10
<211> LENGTH: 1730
<212> TYPE: PRT
<213> ORGANISM: sus scrofa
<300> PUBLICATION INFORMATION:
<308> DATABASE ACCESSION NUMBER: GenPept/NP_999511
<309> DATABASE ENTRY DATE: 2004-08-05
<313> RELEVANT RESIDUES IN SEQ ID NO: (1)..(1730)

<400> SEQUENCE: 10

Met Asp Phe Leu Leu Leu Leu Leu Leu Leu Ala Ser Ser Ala Leu Ala
1               5                   10                  15

-continued

```
Gly Leu Ala Ser Trp Thr Val Ser Ser Pro Glu Thr Val Gln Gly Ile
             20                  25                  30
Lys Gly Ser Cys Leu Ile Ile Pro Cys Thr Phe Gly Phe Pro Ala Asn
         35                  40                  45
Val Glu Val Pro His Gly Ile Thr Ala Ile Trp Tyr Tyr Asp Tyr Ser
     50                  55                  60
Gly Lys Arg Leu Val Val Ser His Ser Arg Asn Pro Lys Val Val Glu
 65                  70                  75                  80
Asn His Phe Gln Gly Arg Ala Leu Leu Leu Gly Gln Val Glu Gln Arg
                 85                  90                  95
Thr Cys Ser Leu Leu Leu Lys Asp Leu Gln Pro Gln Asp Ser Gly Ser
            100                 105                 110
Tyr Asn Phe Arg Phe Glu Ile Ser Glu Gly Asn Arg Trp Ser Asp Val
        115                 120                 125
Lys Gly Thr Val Val Thr Val Thr Glu Val Pro Ser Val Pro Thr Ile
130                 135                 140
Ala Leu Pro Ala Lys Leu His Glu Gly Met Glu Val Asp Phe Asn Cys
145                 150                 155                 160
Ser Thr Pro Tyr Val Cys Pro Thr Glu Pro Val Asn Leu Gln Trp Gln
                165                 170                 175
Gly Gln Asp Pro Thr Arg Ser Val Thr Ser His Leu Gln Lys Leu Glu
            180                 185                 190
Pro Ser Gly Thr Ser His Met Glu Thr Leu His Met Ala Leu Ser Trp
        195                 200                 205
Gln Asp His Gly Arg Ile Leu Ser Cys Gln Val Ser Ala Ala Glu Arg
    210                 215                 220
Arg Met Gln Lys Glu Ile His Leu Gln Val Gln Tyr Ala Pro Lys Gly
225                 230                 235                 240
Val Glu Ile Leu Phe Ser His Ser Gly Arg Asn Val Leu Pro Gly Asp
                245                 250                 255
Leu Val Thr Leu Ser Cys Gln Val Asn Ser Ser Asn Pro Gln Val Ser
            260                 265                 270
Ser Val Gln Trp Val Lys Asp Gly Thr Lys Leu Lys Asp Gln Lys Arg
        275                 280                 285
Val Leu Gln Leu Arg Arg Ala Ala Trp Ala Asp Ala Gly Val Tyr Thr
    290                 295                 300
Cys Gln Ala Gly Asn Ala Val Gly Ser Ser Val Ser Pro Pro Val Ser
305                 310                 315                 320
Leu His Val Phe Met Ala Glu Val Gln Val Ser Pro Val Gly Ser Ile
                325                 330                 335
Leu Glu Asn Gln Thr Val Thr Leu Ala Cys Asn Thr Pro Lys Glu Ala
            340                 345                 350
Pro Ser Glu Leu Arg Tyr Ser Trp Tyr Lys Asn His Ala Leu Leu Glu
        355                 360                 365
Gly Ser His Ser Arg Thr Leu Arg Leu His Ser Val Thr Arg Ala Asp
    370                 375                 380
Ser Gly Phe Tyr Phe Cys Glu Val Gln Asn Ala Arg Gly Arg Glu Arg
385                 390                 395                 400
Ser Pro Pro Val Ser Val Val Ser His Pro Pro Leu Thr Pro Asp
                405                 410                 415
Leu Thr Ala Phe Leu Glu Thr Gln Ala Gly Leu Val Gly Ile Leu Gln
            420                 425                 430
Cys Ser Val Val Ser Glu Pro Pro Ala Thr Leu Val Leu Ser His Gly
        435                 440                 445
```

```
Gly Leu Ile Leu Ala Ser Thr Ser Gly Glu Gly Asp His Ser Pro Arg
    450                 455                 460

Phe Ser Val Ala Ser Ala Pro Asn Ser Leu Arg Leu Glu Ile Gln Asp
465                 470                 475                 480

Leu Gly Pro Thr Asp Ser Gly Glu Tyr Met Cys Ser Ala Ser Ser Ser
                485                 490                 495

Leu Gly Asn Ala Ser Ser Thr Leu Asp Phe His Ala Asn Ala Ala Arg
            500                 505                 510

Leu Leu Ile Ser Pro Ala Ala Glu Val Val Glu Gly Gln Ala Val Thr
        515                 520                 525

Leu Ser Cys Arg Ser Ser Leu Ser Leu Met Pro Asp Thr Arg Phe Ser
    530                 535                 540

Trp Tyr Leu Asn Gly Ala Leu Ile Leu Glu Gly Pro Ser Ser Ser Leu
545                 550                 555                 560

Leu Leu Pro Ala Ala Ser Ser Thr Asp Ala Gly Ser Tyr His Cys Arg
                565                 570                 575

Ala Gln Asn Ser His Ser Thr Ser Gly Pro Ser Ser Pro Ala Val Leu
            580                 585                 590

Thr Val Leu Tyr Ala Pro Arg Gln Pro Val Phe Thr Ala Gln Leu Asp
        595                 600                 605

Pro Asp Thr Ala Gly Ala Gly Ala Gly Arg Gln Gly Leu Leu Leu Cys
    610                 615                 620

Arg Val Asp Ser Asp Pro Pro Ala Gln Leu Gln Leu Leu His Arg Gly
625                 630                 635                 640

Arg Val Val Ala Ser Ser Leu Ser Trp Gly Gly Gly Cys Cys Thr Cys
                645                 650                 655

Gly Gly Cys Phe His Arg Met Lys Val Thr Lys Ala Pro Asn Leu Leu
            660                 665                 670

Arg Val Glu Ile Arg Asp Pro Val Leu Glu Asp Glu Gly Val Tyr Leu
        675                 680                 685

Cys Glu Ala Ser Ser Ala Leu Gly Asn Ala Ser Ala Ser Ala Thr Leu
    690                 695                 700

Asp Ala Gln Ala Thr Val Leu Val Ile Thr Pro Ser His Thr Leu Gln
705                 710                 715                 720

Glu Gly Ile Glu Ala Asn Leu Thr Cys Asn Val Ser Arg Glu Ala Ser
                725                 730                 735

Gly Pro Ala Asn Phe Ser Trp Phe Arg Asp Gly Ala Leu Trp Ala Gln
            740                 745                 750

Gly Pro Leu Asp Thr Val Thr Leu Leu Pro Val Ala Arg Thr Asp Ala
        755                 760                 765

Ala Leu Tyr Ala Cys Arg Ile Val Thr Glu Ala Gly Ala Gly Leu Ser
    770                 775                 780

Thr Pro Val Ala Leu Asn Val Leu Tyr Pro Pro Asp Pro Pro Lys Leu
785                 790                 795                 800

Ser Ala Leu Leu Asp Val Asp Gln Gly His Thr Ala Val Phe Val Cys
                805                 810                 815

Thr Val Asp Ser Arg Pro Leu Ala Gln Leu Ala Leu Phe Arg Gly Glu
            820                 825                 830

His Leu Leu Ala Ala Ser Ala Leu Arg Leu Pro Pro Arg Gly Arg
        835                 840                 845

Leu Gln Ala Lys Ala Ser Ala Asn Ser Leu Gln Leu Glu Val Arg Asp
    850                 855                 860

Leu Ser Leu Gly Asp Ser Gly Ser Tyr His Cys Glu Ala Thr Asn Ile
```

```
              865                 870                 875                 880
Leu Gly Ser Ala Asn Thr Ser Leu Thr Phe Gln Val Arg Gly Ala Trp
                    885                 890                 895
Val Arg Val Ser Pro Ser Pro Glu Leu Gln Glu Gly Gln Ala Val Val
                900                 905                 910
Leu Ser Cys Gln Val Pro Ile Gly Val Leu Glu Gly Thr Ser Tyr Arg
                915                 920                 925
Trp Tyr Arg Asp Gly Gln Pro Leu Gln Glu Ser Thr Ala Thr Leu
        930                 935                 940
Arg Phe Ala Ala Ile Thr Leu Ser Gln Ala Gly Ala Tyr His Cys Gln
945                 950                 955                 960
Ala Gln Ala Pro Gly Ser Ala Thr Thr Asp Leu Ala Ala Pro Val Ser
                965                 970                 975
Leu His Val Thr Tyr Ala Pro Arg Gln Ala Thr Leu Thr Thr Leu Met
                980                 985                 990
Asp Ser Gly Leu Gly Arg Leu Gly  Leu Leu Leu Cys Arg  Val Asn Ser
            995                 1000               1005
Asp Pro  Pro Ala Gln Leu Arg  Leu Leu His Gly Ser  Arg Leu Val
    1010                1015               1020
Ala Ser  Thr Leu Gln Gly Val  Glu Glu Leu Ala Gly  Ser Ser Pro
    1025                1030               1035
Arg Leu  Gln Val Ala Thr Ala  Pro Asn Thr Leu Arg  Leu Glu Ile
    1040                1045               1050
His Asn  Ala Val Leu Glu Asp  Glu Gly Val Tyr Thr  Cys Glu Ala
    1055                1060               1065
Thr Asn  Thr Leu Gly Gln Thr  Leu Ala Ser Ala Ala  Phe Asp Ala
    1070                1075               1080
Gln Ala  Met Arg Val Gln Val  Trp Pro Asn Ala Thr  Val Gln Glu
    1085                1090               1095
Gly Gln  Leu Val Asn Leu Thr  Cys Leu Val Trp Thr  Thr His Leu
    1100                1105               1110
Ala Gln  Leu Thr Tyr Thr Trp  Tyr Arg Asp Gln Gln  Gln Leu Pro
    1115                1120               1125
Gly Ala  Ala His Ser Ile Leu  Leu Pro Asn Val Thr  Val Thr Asp
    1130                1135               1140
Ala Ala  Ser Tyr Arg Cys Gly  Ile Leu Ile Pro Gly  Gln Ala Leu
    1145                1150               1155
Arg Leu  Ser Arg Pro Val Ala  Leu Asp Val Leu Tyr  Ala Pro Arg
    1160                1165               1170
Arg Leu  Arg Leu Thr His Leu  Leu Glu Ser Arg Gly  Gly Gln Leu
    1175                1180               1185
Ala Val  Val Leu Cys Thr Val  Asp Ser Arg Pro Ala  Ala Gln Leu
    1190                1195               1200
Thr Leu  Ser His Ala Gly Arg  Leu Leu Ala Ser Ser  Thr Ala Ala
    1205                1210               1215
Ser Val  Pro Asn Thr Leu Arg  Leu Glu Leu Trp Glu  Pro Arg Pro
    1220                1225               1230
Ser Asp  Glu Gly Leu Tyr Ser  Cys Ser Ala Arg Ser  Pro Leu Gly
    1235                1240               1245
Gln Ala  Asn Thr Ser Leu Glu  Leu Arg Leu Glu Gly  Val Gln Val
    1250                1255               1260
Ala Leu  Ala Pro Ser Ala Thr  Val Pro Glu Gly Ala  Pro Val Thr
    1265                1270               1275
```

-continued

Val Thr Cys Glu Asp Pro Ala Ala Arg Pro Pro Thr Leu Tyr Val
1280            1285            1290

Trp Tyr His Asn Ser Arg Trp Leu Gln Glu Gly Ser Ala Ala Ser
1295            1300            1305

Leu Ser Phe Pro Ala Ala Thr Arg Ala His Ala Gly Ala Tyr Thr
1310            1315            1320

Cys Gln Val Gln Asp Ala Gln Gly Thr Arg Ile Ser Gln Pro Ala
1325            1330            1335

Ala Leu His Ile Leu Tyr Ala Pro Arg Asp Ala Val Leu Ser Ser
1340            1345            1350

Phe Trp Asp Ser Arg Ala Ser Pro Met Ala Val Val Gln Cys Thr
1355            1360            1365

Val Asp Ser Glu Pro Pro Ala Glu Met Thr Leu Ser His Asp Gly
1370            1375            1380

Lys Val Leu Ala Thr Ser His Gly Val His Gly Leu Ala Val Gly
1385            1390            1395

Thr Gly His Val Gln Val Ala Arg Asn Ala Leu Gln Leu Arg Val
1400            1405            1410

Gln Asn Val Pro Ser Arg Asp Lys Asp Thr Tyr Val Cys Met Asp
1415            1420            1425

Arg Asn Ser Leu Gly Ser Val Ser Thr Met Gly Gln Leu Gln Pro
1430            1435            1440

Glu Gly Val His Val Val Ala Glu Pro Gly Leu Asp Val Pro Glu
1445            1450            1455

Gly Thr Ala Leu Asn Leu Ser Cys Arg Leu Pro Ser Gly Pro Gly
1460            1465            1470

His Ile Gly Asn Ser Thr Phe Ala Trp Phe Arg Asn Gly Arg Gln
1475            1480            1485

Leu His Thr Glu Ser Val Pro Thr Leu Thr Phe Thr His Val Ala
1490            1495            1500

Arg Ala Gln Ala Gly Leu Tyr His Cys Gln Ala Glu Leu Pro Ala
1505            1510            1515

Gly Ala Ala Thr Ser Ala Pro Val Leu Leu Arg Val Leu Tyr Pro
1520            1525            1530

Pro Lys Thr Pro Thr Met Thr Val Phe Val Glu Pro Glu Gly Gly
1535            1540            1545

Ile Gln Gly Ile Leu Asp Cys Arg Val Asp Ser Glu Pro Leu Ala
1550            1555            1560

Ser Leu Thr Leu His Leu Gly Ser Arg Leu Val Ala Ser Ser Gln
1565            1570            1575

Pro Gln Ala Ala Pro Ala Lys Pro His Ile Arg Val Ser Ala Ser
1580            1585            1590

Pro Asn Ala Leu Arg Val Asp Met Glu Glu Leu Lys Pro Ser Asp
1595            1600            1605

Gln Gly Glu Tyr Val Cys Ser Ala Ser Asn Ala Leu Gly Ser Ala
1610            1615            1620

Ser Ala Ala Thr Tyr Phe Gly Thr Arg Ala Leu His Arg Leu His
1625            1630            1635

Leu Phe Gln His Leu Leu Trp Phe Leu Gly Leu Leu Ala Ser Leu
1640            1645            1650

Leu Phe Leu Leu Leu Gly Leu Gly Val Trp Tyr Ala Trp Arg Arg
1655            1660            1665

Gly Asn Phe Tyr Lys Leu Arg Met Gly Glu Tyr Ser Val Glu Met
1670            1675            1680

```
Val Ser Arg Lys Glu Thr Thr Gln Met Ser Thr Asp Gln Glu Glu
    1685                1690                1695

Val Thr Gly Ile Gly Asp Asp Ala Gly Ser Val Asn Gln Ala Ala
    1700                1705                1710

Phe Asp Pro Ala His Leu Cys Glu Asn Thr Gln Ser Val Lys Ser
    1715                1720                1725

Thr Val
    1730

<210> SEQ ID NO 11
<211> LENGTH: 6387
<212> TYPE: DNA
<213> ORGANISM: mus musculus
<300> PUBLICATION INFORMATION:
<308> DATABASE ACCESSION NUMBER: GenBank/NM_011426
<309> DATABASE ENTRY DATE: 2000-01-25
<313> RELEVANT RESIDUES IN SEQ ID NO: (1)..(6387)

<400> SEQUENCE: 11
agacaagatt aggcctagag taagtctatg aaacacagag aaaggggaca gcatagggt      60 taagaaatga ggtctttcaa aatctcaggg ggcaatgagg agtttttttga gagaggaagg   120 actcttttaaa ggaagttgaa ggaggattct gtgaacttga gaccaccctg agctgccaag   180
ttgagaactt tgtctacaaa caagccaggc agcctcagcg tgtgctcagt ccgacttgta    240
gctggagagg caggagacca atttccggtg cttacggtgc ttgctggatg ccctggagta    300
agtgacaggg tctcactgga ctccaggttc tgttggtttg agtaatagga ggcggcaggg    360
gagaagtgaa gagagacatg cactgctgat ctgccttgag gctgtgtcct taaggggtgg    420
agccaagggg cacagaagac tctctgggac atgccaccaa gtgagagcat ttccaatcac    480
tccctgagcc aggaacaggg gcttctggtt ccctgctggt ggctgccaca gcagtccttc    540 ctgtttgggtt gaccaacaca gcaggtgaga taaaccctat agacttgggc cctggagtgc    600
tccaggcagt ctctgtgtgc ctacccaccc ggcttcccta ggcacctgaa tgcacctggg   660
cactgggatg tgtgtcctgt tctccctgct cctgctggcc tctgtcttct cactaggcca    720
gaccacatgg ggtgtctcca gtcccaagaa tgtgcagggc ttgtcgggat cctgcctgct    780
cattccctgc atcttcagct accctgccga tgtcccagtg tccaatggca tcacagccat    840
ctggtactat gactactcgg gcaagcggca ggtggtaatc cactcagggg accccaagct    900
ggtggacaag cgtttcaggg gtcgagctga actgatgggg aacatggacc acaaggtgtg    960
caacctgttg ctcaaagact tgaagcctga agactctggc acctacaact tccgctttga   1020
gatcagtgat agcaaccgct ggttagatgt caaaggcacc acggtcactg tgacaacgga   1080
tcccagcccc cccactatta ccattcctga ggagctgcgt gaaggcatgg agaggaactt   1140
caactgttcc acaccctacc tgtgcctgca ggagaagcaa gtcagcctgc agtggcgagg   1200
ccaggacccc acccactctg tcacctccag cttccagagc ctcgagccca ctggcgtcta   1260
tcaccagacg accctacata tggccctatc ctggcaggac cacggtcgga ccctgctctg   1320
ccagttctca ttgggcgcac acagtagtcg gaaagaggtt tacctgcaag tgccacatgc   1380
ccccaaaggt gtggagatcc tcctcagctc ctcaggagg aacatccttc ccggggatcc    1440
agtcacactc acctgcagag tgaacagcag ctatcctgct gtcagtgccg tgcagtgggc   1500
cagggacgga gtgaacctcg gagtcacggg acatgtgctt cggctgttct cagcagcctg   1560
gaatgattct ggggcctaca cctgccaagc aacaaatgat atgggctctc tggtgtcatc   1620
cccgctcagc ctccatgttt ttatggctga agtcaaaatg aaccccgcag ggccccgtctt   1680
```

```
ggaaaatgag acagtgactc tgctctgtag cacgccgaag gaggctcccc aggagctccg   1740
ctatagctgg tacaagaacc acattctcct ggaagatgcc catgcctcaa ccttgcacct   1800
gcctgcagtc accagggctg atactggctt ctacttctgt gaagtgcaga atgcccaggg   1860
cagtgagcgc tccagtccat tgagtgtggt ggtcagatat ccaccccttn ctccagacct   1920
gaccaccttc ctggagacac aggccggact tgtgggcatc ttgcattgct ccgtggtcag   1980
tgagcccctg gctactgtgg tgctgtcaca cggaggcctc acgttggcct ccaactctgg   2040
agaaaatgac ttcaaccccc gattcaggat ctcctctgcc cccaactccc tgcgcctaga   2100
aatccgagac ttgcagccag cagacagcgg agagtacaca tgcttagctg tcaactccct   2160
tggaaactca acgtccagcc tagacttcta tgctaatgtg gcccgactcc tcatcaaccc   2220
ttcagcagag gttgtggaag ggcaggcggt gaccctgagc tgcaggagtg gcctgagccc   2280
agctcctgac actcgcttct cctggtacct gaacggagct ctacttctgg aaggatccag   2340
cagcagcctc ctgcttcctg cggcttccag cactgatgcg ggctcatact actgtaggac   2400
gcaggctggc cccaacacca gcggcccctc cctgcctact gtcctcactg tgttctatcc   2460
cccaagaaag cccacattca ctgccaggct ggatttggat acctctggag tcggggatgg   2520
acgacggggc atcctcttgt gccacgtaga cagcgatccc ccagcccagc tacggcttct   2580
ccacaaaggc catgttgtgg ccacttctct gccatcaagg tgtgggagct gttcccagcg   2640
cacaaaagtc agcagaacct ccaactcact gcacgtggag atccagaagc ctgtattaga   2700
ggatgagggc gtgtacctgt gtgaggctag caacacattg gcaactcct cagccgcagc   2760 ctctttcaat gctaaggcca ctgtactggt catcacaccg tcaaatacac tgcgtgaagg   2820
cacagaggcc aacctaactt gcaacgtgaa ccaggaggtt gctgtcagcc ctgccaactt   2880
ctcctggttc cggaatggag tgctgtggac ccagggatca ctggagactg tgaggctgca   2940
gcctgtggcc agaactgatg ctgctgtcta tgcctgccgc ctcctcaccg aggatggggc   3000
tcagctctcg gctcctgtgg tcctaagtgt gctgtatgcc ccagaccctc aaagctgtc   3060 agccctccta gatgtgggtc agggccacat ggccgtgttc atctgcactg tggacagcta   3120
tcccctggct cacctgtctc tgttccgtgg ggaccatctc ctggccacca acttggaacc   3180
ccagcgtccc tccatggca ggatccaggc caaggccaca gccaactccc tgcagctaga   3240
ggtccgagaa ctaggtcttg tggactctgg aaactaccac tgtgaagcca ccaatattct   3300
tgggtcagcc aacagttcac tcttcttcca ggtcagagga gcctgggtcc aggtttcacc   3360
atcacctgag ctccgggagg ccaggctgt ggtcctgagc tgccaggtgc cacaggagt   3420 ctctgagggg acctcataca gctggtatca ggatggccgc cccctccagg agtcaacctc   3480
atctacactc cgcattgcag ccataagtct gaggcaagct ggtgcctacc attgccaagc   3540
tcaggcccca gacacagcta ttgccagcct ggctgcccct gtcagcctcc atgtgtccta   3600
taccccacgt catgttacac tcagtgccct gctgagcacg gaccctgagc gactaggcca   3660
cctggtgtgc agtgtacaaa gtgaccctcc agcgcagctg caactgtttc accggaatcg   3720
cctcgtggcc tctaccctac aaggcgcgga cgaattggca ggcagtaatc cccggctgca   3780
tgtgactgtg ctccccaatg agctgcgcct gcagatccac tttcagagc tggaggatga   3840 cgggaccat acatgcgaag ccagcaacac actgggccag gcctcggctg cagctgactt   3900
cgatgcccag gctgtgcgag tgactgtgtg gcccaatgcc actgtgcaag aggggcagca   3960
ggtgaacctg acctgcttgg tgtggagcac caccggac tcactcagct acacatggta   4020
caagggcggg caacaactcc ttggtgccag atccatcacc ctgcccagtg ttaaggtttt   4080
```

```
ggatgctacc tcctaccgct gtggtgtggg gctcccggc cacgcacccc atctctccag   4140
acccgtgacc ctggatgtcc tccatgctcc ccgaaacctg cggctgacct acctcctaga   4200
gacccagggc aggcagctgg ccctggtact gtgtacggtg gatagtcgtc cacctgccca   4260
gctaactctc agccatggtg accagcttgt agcctcctca actgaagcct ctgtcccaa    4320 caccctgcgc ctagagcttc aggatccaag gcctagtaat gagggctct atagctgctc    4380 tgcccacagc ccattgggca aggccaacac gtccctggaa cttctgctgg aaggtgtccg   4440
agtgaaaatg aatccctctg gtagtgtacc cgagggagag cctgtcacag tgacctgcga   4500
ggaccctgct gccctctcat ccgccctcta tgcctggttt cacaatggcc attggcttca   4560
ggagggaccg gcttcctcac tccagttcct ggtgactaca cgggctcacg ctggtgctta   4620
cttttgccag gtgcatgata cacaaggcac acgagctcc agacctgcca gcctgcaaat    4680
tctctatgcc cccgggatg ctgtcctgtc ttcctttcga gactcaagga ccaggctcat    4740
ggtcgtgatt cagtgcaccg tggacagtga gccacctgct gagatggtcc tatcccacaa   4800
tggcaaggtg ctagctgcca gccacgagcg tcacagctca gcatcaggga taggccacat   4860
ccaggtagcc cgaaatgctc ttcgactaca agtgcaagat gtgactctgg gtgatggcaa   4920
cacctatgtt tgcacagccc agaatacact gggctccatc agtaccaccc agaggcttct   4980 gacgagact gatatacgtg tgacagctga gccaggcttg gatgtgccag agggcacagc    5040
tctgaactta agctgcctcc tccctggtgg ctctgggccc acgggcaact cttccttcac   5100
gtggttctgg aatcgccacc gactacattc agctcctgtg cccacactct ccttcacccc   5160
tgtggtccgg gctcaggctg ggctgtacca ctgcagggct gatctcccca ccggggccac   5220
tacctctgct ccagttatgc tccgtgtcct ctatcccccc aagacgccca ctctcatagt   5280
gtttgtggag cctcagggtg gccaccaggg catcctcgac tgtcgagtgg acagtgagcc   5340
cctggccatc ctcactcttc accggggcag tcaactagta gcctccaacc aacttcacga   5400
tgctcccacc aagccccaca tccgagtcac tgctcctccc aatgccttga gagtggacat   5460
agaggagctc ggccctagca atcaagggga gtatgtgtgc actgcctcca acactctggg   5520
ctctgcctca gcctctgcct actttgggac cagagctctg caccaactgc agctgttcca   5580
gaggctgctc tgggtcctgg gatttctggc aggcttcctg tgcctgctgc tgggtctggt   5640
ggcctatcac acctggagaa agaagagttc taccaagctg aatgaggatg agaattcagc   5700
agagatggcc actaagaaaa atactatcca ggaggaagtg gttgctgctc tctgacaact   5760
caggtgctgt gaacaagatc ctgcctacct ctgtataagc agtacagaga catctggctt   5820
tcctgacctg cccgacttgc cttccaagcc tcttgatcct aagaaaaatg gacgaaggga   5880 ggtttgggt tggaggtcaa cctgccgcct ccagggctct gagacggact cagccatgtt   5940
gcccacgtct ctctgtgtgg ttttcctctg tatcccttg cctttctctt caaagctcac    6000
cttggacttt cttggtgggt tagagcaaca tccagtttct cacagacttt ctaagacggt    6060
ctgtaccagc caggatatca gtcaggttgc tctaacagag actcaataca gtgaccacag    6120
catgacaggg tcttagtttt ccctcctggc ctggttatgt tgttgtggta tcagaatcct    6180
tcttgcttga ttttctccat tccccaagtg ttgcctttga ttatgaagct caggtaactg    6240 cagtgccat ggaccctaca gggagaagga agagtgaagg gaagacatac ccatcccat     6300 ggtccatgga ctgtgtgtgc aattgcaccc cacccaactt ctcatccgct agaaactggt    6360
cacataaaca taccatgctg aaaggga                                        6387
```

-continued

```
<210> SEQ ID NO 12
<211> LENGTH: 1695
<212> TYPE: PRT
<213> ORGANISM: mus musculus
<300> PUBLICATION INFORMATION:
<308> DATABASE ACCESSION NUMBER: GenPept
<309> DATABASE ENTRY DATE: 2000-01-25
<313> RELEVANT RESIDUES IN SEQ ID NO: (1)..(1695)

<400> SEQUENCE: 12

Met Cys Val Leu Phe Ser Leu Leu Leu Ala Ser Val Phe Ser Leu
1               5                   10                  15

Gly Gln Thr Thr Trp Gly Val Ser Ser Pro Lys Asn Val Gln Gly Leu
            20                  25                  30

Ser Gly Ser Cys Leu Leu Ile Pro Cys Ile Phe Ser Tyr Pro Ala Asp
        35                  40                  45

Val Pro Val Ser Asn Gly Ile Thr Ala Ile Trp Tyr Tyr Asp Tyr Ser
    50                  55                  60

Gly Lys Arg Gln Val Val Ile His Ser Gly Asp Pro Lys Leu Val Asp
65                  70                  75                  80

Lys Arg Phe Arg Gly Arg Ala Glu Leu Met Gly Asn Met Asp His Lys
                85                  90                  95

Val Cys Asn Leu Leu Leu Lys Asp Leu Lys Pro Glu Asp Ser Gly Thr
            100                 105                 110

Tyr Asn Phe Arg Phe Glu Ile Ser Asp Ser Asn Arg Trp Leu Asp Val
        115                 120                 125

Lys Gly Thr Thr Val Thr Val Thr Thr Asp Pro Ser Pro Thr Ile
130                 135                 140

Thr Ile Pro Glu Glu Leu Arg Glu Gly Met Glu Arg Asn Phe Asn Cys
145                 150                 155                 160

Ser Thr Pro Tyr Leu Cys Leu Gln Glu Lys Gln Val Ser Leu Gln Trp
                165                 170                 175

Arg Gly Gln Asp Pro Thr His Ser Val Thr Ser Ser Phe Gln Ser Leu
            180                 185                 190

Glu Pro Thr Gly Val Tyr His Gln Thr Thr Leu His Met Ala Leu Ser
        195                 200                 205

Trp Gln Asp His Gly Arg Thr Leu Leu Cys Gln Phe Ser Leu Gly Ala
    210                 215                 220

His Ser Ser Arg Lys Glu Val Tyr Leu Gln Val Pro His Ala Pro Lys
225                 230                 235                 240

Gly Val Glu Ile Leu Leu Ser Ser Gly Arg Asn Ile Leu Pro Gly
                245                 250                 255

Asp Pro Val Thr Leu Thr Cys Arg Val Asn Ser Ser Tyr Pro Ala Val
            260                 265                 270

Ser Ala Val Gln Trp Ala Arg Asp Gly Val Asn Leu Gly Val Thr Gly
        275                 280                 285

His Val Leu Arg Leu Phe Ser Ala Ala Trp Asn Asp Ser Gly Ala Tyr
    290                 295                 300

Thr Cys Gln Ala Thr Asn Asp Met Gly Ser Leu Val Ser Ser Pro Leu
305                 310                 315                 320

Ser Leu His Val Phe Met Ala Glu Val Lys Met Asn Pro Ala Gly Pro
                325                 330                 335

Val Leu Glu Asn Glu Thr Val Thr Leu Leu Cys Ser Thr Pro Lys Glu
            340                 345                 350

Ala Pro Gln Glu Leu Arg Tyr Ser Trp Tyr Lys Asn His Ile Leu Leu
        355                 360                 365
```

-continued

Glu Asp Ala His Ala Ser Thr Leu His Leu Pro Ala Val Thr Arg Ala
370                 375                 380

Asp Thr Gly Phe Tyr Phe Cys Glu Val Gln Asn Ala Gln Gly Ser Glu
385                 390                 395                 400

Arg Ser Ser Pro Leu Ser Val Val Arg Tyr Pro Pro Leu Thr Pro
    405                 410                 415

Asp Leu Thr Thr Phe Leu Glu Thr Gln Ala Gly Leu Val Gly Ile Leu
        420                 425                 430

His Cys Ser Val Val Ser Glu Pro Leu Ala Thr Val Leu Ser His
    435                 440                 445

Gly Gly Leu Thr Leu Ala Ser Asn Ser Gly Glu Asn Asp Phe Asn Pro
450                 455                 460

Arg Phe Arg Ile Ser Ser Ala Pro Asn Ser Leu Arg Leu Glu Ile Arg
465                 470                 475                 480

Asp Leu Gln Pro Ala Asp Ser Gly Glu Tyr Thr Cys Leu Ala Val Asn
                485                 490                 495

Ser Leu Gly Asn Ser Thr Ser Ser Leu Asp Phe Tyr Ala Asn Val Ala
            500                 505                 510

Arg Leu Leu Ile Asn Pro Ser Ala Glu Val Val Glu Gly Gln Ala Val
        515                 520                 525

Thr Leu Ser Cys Arg Ser Gly Leu Ser Pro Ala Pro Asp Thr Arg Phe
530                 535                 540

Ser Trp Tyr Leu Asn Gly Ala Leu Leu Leu Glu Gly Ser Ser Ser Ser
545                 550                 555                 560

Leu Leu Leu Pro Ala Ala Ser Ser Thr Asp Ala Gly Ser Tyr Tyr Cys
                565                 570                 575

Arg Thr Gln Ala Gly Pro Asn Thr Ser Gly Pro Ser Leu Pro Thr Val
            580                 585                 590

Leu Thr Val Phe Tyr Pro Pro Arg Lys Pro Thr Phe Thr Ala Arg Leu
        595                 600                 605

Asp Leu Asp Thr Ser Gly Val Gly Asp Gly Arg Arg Gly Ile Leu Leu
    610                 615                 620

Cys His Val Asp Ser Asp Pro Pro Ala Gln Leu Arg Leu Leu His Lys
625                 630                 635                 640

Gly His Val Val Ala Thr Ser Leu Pro Ser Arg Cys Gly Ser Cys Ser
                645                 650                 655

Gln Arg Thr Lys Val Ser Arg Thr Ser Asn Ser Leu His Val Glu Ile
            660                 665                 670

Gln Lys Pro Val Leu Glu Asp Glu Gly Val Tyr Leu Cys Glu Ala Ser
        675                 680                 685

Asn Thr Leu Gly Asn Ser Ala Ala Ala Ser Phe Asn Ala Lys Ala
    690                 695                 700

Thr Val Leu Val Ile Thr Pro Ser Asn Thr Leu Arg Glu Gly Thr Glu
705                 710                 715                 720

Ala Asn Leu Thr Cys Asn Val Asn Gln Glu Val Ala Val Ser Pro Ala
                725                 730                 735

Asn Phe Ser Trp Phe Arg Asn Gly Val Leu Trp Thr Gln Gly Ser Leu
            740                 745                 750

Glu Thr Val Arg Leu Gln Pro Val Ala Arg Thr Asp Ala Ala Val Tyr
        755                 760                 765

Ala Cys Arg Leu Leu Thr Glu Asp Gly Ala Gln Leu Ser Ala Pro Val
    770                 775                 780

Val Leu Ser Val Leu Tyr Ala Pro Asp Pro Pro Lys Leu Ser Ala Leu
785                 790                 795                 800

```
Leu Asp Val Gly Gln Gly His Met Ala Val Phe Ile Cys Thr Val Asp
                805                 810                 815

Ser Tyr Pro Leu Ala His Leu Ser Leu Phe Arg Gly Asp His Leu Leu
                820                 825                 830

Ala Thr Asn Leu Glu Pro Gln Arg Pro Ser His Gly Arg Ile Gln Ala
                835                 840                 845

Lys Ala Thr Ala Asn Ser Leu Gln Leu Glu Val Arg Glu Leu Gly Leu
                850                 855                 860

Val Asp Ser Gly Asn Tyr His Cys Glu Ala Thr Asn Ile Leu Gly Ser
865                 870                 875                 880

Ala Asn Ser Ser Leu Phe Phe Gln Val Arg Gly Ala Trp Val Gln Val
                885                 890                 895

Ser Pro Ser Pro Glu Leu Arg Glu Gly Gln Ala Val Val Leu Ser Cys
                900                 905                 910

Gln Val Pro Thr Gly Val Ser Glu Gly Thr Ser Tyr Ser Trp Tyr Gln
                915                 920                 925

Asp Gly Arg Pro Leu Gln Glu Ser Thr Ser Ser Thr Leu Arg Ile Ala
                930                 935                 940

Ala Ile Ser Leu Arg Gln Ala Gly Ala Tyr His Cys Gln Ala Gln Ala
945                 950                 955                 960

Pro Asp Thr Ala Ile Ala Ser Leu Ala Ala Pro Val Ser Leu His Val
                965                 970                 975

Ser Tyr Thr Pro Arg His Val Thr Leu Ser Ala Leu Leu Ser Thr Asp
                980                 985                 990

Pro Glu Arg Leu Gly His Leu Val Cys Ser Val Gln Ser Asp Pro Pro
                995                 1000                1005

Ala Gln Leu Gln Leu Phe His Arg Asn Arg Leu Val Ala Ser Thr
                1010                1015                1020

Leu Gln Gly Ala Asp Glu Leu Ala Gly Ser Asn Pro Arg Leu His
                1025                1030                1035

Val Thr Val Leu Pro Asn Glu Leu Arg Leu Gln Ile His Phe Pro
                1040                1045                1050

Glu Leu Glu Asp Asp Gly Thr Tyr Thr Cys Glu Ala Ser Asn Thr
                1055                1060                1065

Leu Gly Gln Ala Ser Ala Ala Ala Asp Phe Asp Ala Gln Ala Val
                1070                1075                1080

Arg Val Thr Val Trp Pro Asn Ala Thr Val Gln Glu Gly Gln Gln
                1085                1090                1095

Val Asn Leu Thr Cys Leu Val Trp Ser Thr His Gln Asp Ser Leu
                1100                1105                1110

Ser Tyr Thr Trp Tyr Lys Gly Gly Gln Gln Leu Leu Gly Ala Arg
                1115                1120                1125

Ser Ile Thr Leu Pro Ser Val Lys Val Leu Asp Ala Thr Ser Tyr
                1130                1135                1140

Arg Cys Gly Val Gly Leu Pro Gly His Ala Pro His Leu Ser Arg
                1145                1150                1155

Pro Val Thr Leu Asp Val Leu His Ala Pro Arg Asn Leu Arg Leu
                1160                1165                1170

Thr Tyr Leu Leu Glu Thr Gln Gly Arg Gln Leu Ala Leu Val Leu
                1175                1180                1185

Cys Thr Val Asp Ser Arg Pro Pro Ala Gln Leu Thr Leu Ser His
                1190                1195                1200

Gly Asp Gln Leu Val Ala Ser Ser Thr Glu Ala Ser Val Pro Asn
```

```
                    1205                1210                1215
Thr Leu Arg Leu Glu Leu Gln Asp Pro Arg Pro Ser Asn Glu Gly
    1220                1225                1230
Leu Tyr Ser Cys Ser Ala His Ser Pro Leu Gly Lys Ala Asn Thr
    1235                1240                1245
Ser Leu Glu Leu Leu Leu Glu Gly Val Arg Val Lys Met Asn Pro
    1250                1255                1260
Ser Gly Ser Val Pro Glu Gly Glu Pro Val Thr Val Thr Cys Glu
    1265                1270                1275
Asp Pro Ala Ala Leu Ser Ser Ala Leu Tyr Ala Trp Phe His Asn
    1280                1285                1290
Gly His Trp Leu Gln Glu Gly Pro Ala Ser Ser Leu Gln Phe Leu
    1295                1300                1305
Val Thr Thr Arg Ala His Ala Gly Ala Tyr Phe Cys Gln Val His
    1310                1315                1320
Asp Thr Gln Gly Thr Arg Ser Ser Arg Pro Ala Ser Leu Gln Ile
    1325                1330                1335
Leu Tyr Ala Pro Arg Asp Ala Val Leu Ser Ser Phe Arg Asp Ser
    1340                1345                1350
Arg Thr Arg Leu Met Val Val Ile Gln Cys Thr Val Asp Ser Glu
    1355                1360                1365
Pro Pro Ala Glu Met Val Leu Ser His Asn Gly Lys Val Leu Ala
    1370                1375                1380
Ala Ser His Glu Arg His Ser Ser Ala Ser Gly Ile Gly His Ile
    1385                1390                1395
Gln Val Ala Arg Asn Ala Leu Arg Leu Gln Val Gln Asp Val Thr
    1400                1405                1410
Leu Gly Asp Gly Asn Thr Tyr Val Cys Thr Ala Gln Asn Thr Leu
    1415                1420                1425
Gly Ser Ile Ser Thr Thr Gln Arg Leu Leu Thr Glu Thr Asp Ile
    1430                1435                1440
Arg Val Thr Ala Glu Pro Gly Leu Asp Val Pro Glu Gly Thr Ala
    1445                1450                1455
Leu Asn Leu Ser Cys Leu Leu Pro Gly Gly Ser Gly Pro Thr Gly
    1460                1465                1470
Asn Ser Ser Phe Thr Trp Phe Trp Asn Arg His Arg Leu His Ser
    1475                1480                1485
Ala Pro Val Pro Thr Leu Ser Phe Thr Pro Val Val Arg Ala Gln
    1490                1495                1500
Ala Gly Leu Tyr His Cys Arg Ala Asp Leu Pro Thr Gly Ala Thr
    1505                1510                1515
Thr Ser Ala Pro Val Met Leu Arg Val Leu Tyr Pro Pro Lys Thr
    1520                1525                1530
Pro Thr Leu Ile Val Phe Val Glu Pro Gln Gly Gly His Gln Gly
    1535                1540                1545
Ile Leu Asp Cys Arg Val Asp Ser Glu Pro Leu Ala Ile Leu Thr
    1550                1555                1560
Leu His Arg Gly Ser Gln Leu Val Ala Ser Asn Gln Leu His Asp
    1565                1570                1575
Ala Pro Thr Lys Pro His Ile Arg Val Thr Ala Pro Pro Asn Ala
    1580                1585                1590
Leu Arg Val Asp Ile Glu Glu Leu Gly Pro Ser Asn Gln Gly Glu
    1595                1600                1605
```

```
Tyr Val Cys Thr Ala Ser Asn Thr Leu Gly Ser Ala Ser Ala Ser
1610                1615                1620

Ala Tyr Phe Gly Thr Arg Ala Leu His Gln Leu Gln Leu Phe Gln
1625                1630                1635

Arg Leu Leu Trp Val Leu Gly Phe Leu Ala Gly Phe Leu Cys Leu
1640                1645                1650

Leu Leu Gly Leu Val Ala Tyr His Thr Trp Arg Lys Lys Ser Ser
1655                1660                1665

Thr Lys Leu Asn Glu Asp Glu Asn Ser Ala Glu Met Ala Thr Lys
1670                1675                1680

Lys Asn Thr Ile Gln Glu Glu Val Val Ala Ala Leu
1685                1690                1695

<210> SEQ ID NO 13
<211> LENGTH: 6736
<212> TYPE: DNA
<213> ORGANISM: homo sapiens
<300> PUBLICATION INFORMATION:
<308> DATABASE ACCESSION NUMBER: GenBank/NM_023068
<309> DATABASE ENTRY DATE: 2001-02-13
<313> RELEVANT RESIDUES IN SEQ ID NO: (1)..(6736)

<400> SEQUENCE: 13
atgggcttct tgcccaagct ctcctcctg gcctcattct tcccagcagg ccaggcctca      60
tggggcgtct ccagtcccca ggacgtgcag ggtgtgaagg ggtcttgcct gcttatcccc    120
tgcatcttca gcttccctgc cgacgtggag gtgcccgacg gcatcacggc catctggtac    180
tacgactact cgggccagcg gcaggtggtg agccactcgg cggaccccaa gctggtggag    240
gcccgcttcc gcggccgcac cgagttcatg gggaaccccg agcacagggt gtgcaacctg    300
ctgctgaagg acctgcagcc cgaggactct ggttcctaca acttccgctt cgagatcagt    360
gaggtcaacc gctggtcaga tgtgaaaggc accttggtca cagtaacaga ggagcccagg    420
gtgcccacca ttgcctcccc ggtggagctt ctcgagggca cagaggtgga cttcaactgc    480
tccactccct acgtatgcct gcaggagcag tcagactgc agtggcaagg ccaggaccct    540
gctcgctctg tcaccttcaa cagccagaag tttgagccca ccggcgtcgg ccacctggag    600
accctccaca tggccatgtc ctggcaggac acggccgga tcctgcgctg ccagctctcc    660
gtggccaatc acagggctca gagcgagatt cacctccaag tgaagtatgc ccccaagggt    720
gtgaagatcc tcctcagccc ctcggggagg aacatccttc caggtgagct ggtcacactc    780
acctgccagg tgaacagcag ctaccctgca gtcagttcca ttaagtggct caaggatggg    840
gtacgcctcc aaaccaagac tggtgtgctg caccttgcccc aggcagcctg gagcgatgct    900
ggcgtctaca cctgccaagc tgagaacggc gtgggctctt tggtctcacc ccccatcagc    960
ctccacatct tcatggctga ggtccaggtg agcccagcag gtcccatcct ggagaaccag   1020
acagtgacac tagtctgcaa cacacccaat gaggcaccca gtgatctccg ctacagctgg   1080
tacaagaacc atgtcctgct ggaggatgcc cactcccata ccctccggct gcacttggcc   1140
actaggctgg atactggctt ctacttctgt gaggtgcaga acgtccatgg cagcgagcgc   1200
tcgggccctg tcagcgtggt agtcaaccac ccgcctctca ctccagtcct gacagccttc   1260
ctggagaccc aggcgggact tgtgggcatc cttcactgct ctgtggtcag tgagcccctg   1320
gccacactgg tgctgtcaca tgggggtcat atcctggcct ccacctccgg ggacagtgat   1380
cacagcccac gcttcagtgg tacctctggt cccaactccc tgcgcctgga gatccgagac   1440
ctggaggaaa ctgacagtgg ggagtacaag tgctcagcca ccaactccct tggaaatgca   1500
```

```
acctccaccc tggacttcca tgccaatgcc gcccgtctcc tcatcagccc ggcagccgag   1560
gtggtggaag acaggcagt gacactgagc tgcagaagcg gcctaagccc cacacctgat    1620
gcccgcttct cctggtacct gaatggagcc ctgcttcacg agggtcccgg cagcagcctc   1680
ctgctccccg cggcctccag cactgacgcc ggctcatacc actgccgggc ccgggacggc   1740
cacagtgcca gtggcccctc ttcgccagct gttctcactg tgctctaccc ccctcgacaa   1800
ccaacattca ccaccaggct ggaccttgat gccgctgggg ccggggctgg acggcgaggc   1860
ctccttttgt gccgtgtgga cagcgacccc ccgccaggc tgcagctgct ccacaaggac    1920
cgtgttgtgg ccacttccct gccatcaggg ggtggctgca gcacctgtgg gggctgttcc   1980
ccacgcatga aggtcaccaa agcccccaac ttgctgcgtg tggagattca aaccctttg    2040
ctggaagagg agggcttgta cctctgtgag gccagcaatg ccctgggcaa cgcctccacc   2100
tcagccacct tcaatggcca ggccactgtc ctggccattg caccatcaca cacacttcag   2160
gagggcacag aagccaactt gacttgcaac gtgagccggg aagctgctgg cagccctgct   2220
aacttctcct ggttccgaaa tggggtgctg tgggcccagg gtccctggA gaccgtgaca    2280
ctgctgcccg tggccagaac tgatgctgcc ctttacgcct gccgcatcct gactgaggct   2340
ggtgcccagc tctccactcc cgtgctcctg agtgtactct atccccggA ccgtccaaag    2400
ctgtcagccc cctagacat gggccagggc cacatggctc tgttcatctg cactgtggac    2460
agccgccccc tggccttgct ggccttgttc catggggagc acctcctggc caccagcctg   2520
ggtccccagg tccatccca tggtcggttc caggctaaag ctgaggccaa ctccctgaag    2580
ttagaggtcc gagaactggg ccttggggac tctggcagct accgctgtga ggccacaaat   2640
gttcttggat catccaacac ctcactcttc ttccaggtcc gaggagcctg gtccaggtg    2700
tcaccatcac ctgagctcca agagggccag gctgtggtcc tgagctgcca ggtacacaca   2760
ggagtcccag aggggacctc atatcgttgg tatcgggatg ccagcccct ccaggagtcg    2820
acctcggcca cgctccgctt tgcagccata actttgacac aagctggggc ctatcattgc   2880
caagcccagg ccccaggctc agccaccacg agcctagctg cacccatcag cctccacgtg   2940
tcctatgccc cacgccacgt cacactcact accctgatgg acacaggccc tggacgactg   3000
ggcctcctcc tgtgccgtgt ggacagtgac cctccggccc agctgcggct gctccacggg   3060
gatcgccttg tggcctccac cctacaaggt gtgggggggac ccgaaggcag ctctcccagg    3120
ctgcatgtgg ctgtggcccc caacacactg cgtctggaga tccacggggc tatgctggag   3180
gatgagggtg tctatatctg tgaggcctcc aacaccctgg ccaggcctc ggcctcagct    3240
gacttcgacg ctcaagctgt gaatgtgcag gtgtggcccg gggctaccgt gcgggagggg   3300
cagctggtga acctgacctg ccttgtgtgg accactcacc cggcccagct cacctacaca   3360
tggtaccagg atgggcagca gcgcctggat gcccactcca tcccctgcc caacgtcaca    3420
gtcagggatg ccacctccta ccgctgcggt gtgggccccc ctggtcgggc accccgcctc   3480
tccagaccta tcaccttgga cgtcctctac gcgccccgca acctgcgcct gacctacctc   3540
ctggagagcc atggcgggca gctggccctg gtactgtgca ctgtgacag ccgcccgccc    3600
gcccagctgg ccctcagcca cgccggtcgc ctcttggcct cctcgacagc agcctctgtc   3660
cccaacaccc tgcgcctgga gctgcgaggg ccacagccca gggatgaggg tttctacagc   3720
tgctctgccc gcagccctct gggccaggcc aacacgtccc tggagctgcg gctggagggt   3780
gtgcgggtga tcctggctcc ggaggctgcc gtgcctgaag tgcccccat cacagtgacc   3840
tgtgcggacc ctgctgccca cgcacccaca ctctatactt ggtaccacaa cggtcgttgg   3900
```

```
ctgcaggagg gtccagctgc ctcactctca ttcctggtgg ccacgcgggc tcatgcaggc    3960
gcctactctt gccaggccca ggatgcccag ggcacccgca gctcccgtcc tgctgccctg    4020
caagtcctct atgcccctca ggacgctgtc ctgtcctcct tccgggactc cagggccaga    4080
tccatggctg tgatacagtg cactgtggac agtgagccac ctgctgagct ggccctatct    4140
catgatggca aggtgctggc cacgagcagc ggggtccaca gcttggcatc agggacaggc    4200
catgtccagg tggcccgaaa cgccctacgg ctgcaggtgc aagatgtgcc tgcaggtgat    4260
gacacctatg tttgcacagc ccaaaacttg ctgggctcaa tcagcaccat cgggcggttg    4320
caggtagaag gtgcacgcgt ggtggcagag cctggcctgg acgtgcctga gggcgctgcc    4380
ctgaacctca gctgccgcct cctgggtggc cctgggcctg tgggcaactc cacctttgca    4440
tggttctgga atgaccggcg gctgcacgcg gagcctgtgc ccactctcgc cttcacccac    4500
gtggctcgtg ctcaagctgg gatgtaccac tgcctggctg agctccccac tggggctgct    4560
gcctctgctc cagtcatgct ccgtgtgctc taccctccca agacgcccac catgatggtc    4620
ttcgtggagc ctgagggtgg cctccggggc atcctggatt gccgagtgga cagcgagccg    4680
ctcgccagcc tgactctcca ccttggcagt cgactggtgg cctccagtca gccccagggt    4740
gctcctgcag agccacacat ccatgtcctg gcttccccca atgccctgag ggtggacatc    4800
gaggcgctga ggcccagcga ccaaggggaa tacatctgtt ctgcctcaaa tgtcctgggc    4860
tctgcctcta cctccaccta ctttggggtc agagccctgc accgcctgca tcagttccag    4920
cagctgctct gggtcctggg actgctggtg gcctcctgc tcctgctgtt gggcctgggg    4980
gcctgctaca cctggagaag gaggcgtgtt tgtaagcaga gcatgggcga gaattcggtg    5040
gagatggctt ttcagaaaga gaccacgcag ctcattgatc ctgatgcagc cacatgtgag    5100
acctcaacct gtgccccacc cctgggctga ccagtggtgt tgcctgccct ccggaggaga    5160
aagtggccag aatctgtgat gactccagcc tatgaatgtg aatgaggcag tgttgagtcc    5220
tgcccgcctc tacgaaaaca gctctgtgac atctgacttt ttatgacctg gccccaagcc    5280
tcttgccccc ccaaaaatgg gtggtgagag gtctgcccag gagggtgttg accctggagg    5340
acactgaaga gcactgagct gatctcgctc tctcttctct ggatctcctc ccttctctcc    5400
atttctccct caaaggaagc cctgcccttt cacatccttc tcctcgaaag tcaccctgga    5460 cttggttgg attgcagcat cctgcatcct cagaggctca ccaaggcatt ctgtattcaa    5520
cagagtatca gtcagcctgc tctaacaaga gaccaaatac agtgacttca acatgataga    5580
attttatttt tctctcccac gctagtctgg ctgttacgat ggtttatgat gttgggctc    5640 aggatccttc tatcttcctt ttctctatcc ctaaaatgat gcctttgatt gtgaggctca    5700
ccatggcccc gctttgtcca catgccctcc agccagaaga aggaagagtg gaggtagaag    5760
cacacccatg cccatggtgg acgcaactca gaagctgcac aggacttttc cactcacttc    5820
ccattggctg gagtattgtc acatggctac tgcaagctac aagggagact gggaaatgta    5880
gttttatttt tgagtccaga ggacatttgg aattggactt ccaaaggact cccaactgtg    5940
agctcatccc tgagactttt gacattgttg gaatgccac cagcaggcca tgttttgtct    6000
cagtgcccat ctactgaggg ccagggtgtg cccctggcca ttctggttgt gggcttcctg    6060
gaagaggtga tcactctcac actaagactg aggaaataaa aaaggtttgg tgttttccta    6120
gggagagagc atgccaggca gtggagttgc ctaagcagac atccttgtgc cagatttggc    6180
ccctgaaaga agagatgccc tcattcccac caccaccccc cctaccccca gggactgggt    6240
actaccttac tggcccttac aagagtggag ggcagacaca gatgttgtca gcatccttat    6300
```

```
tcctgctcca gatgcatctc tgttcatgac tgtgtgagct cctgtcctt tcctggagac    6360 cctgtgtcgg gctgttaaag agaatgagtt accaagaagg aatgacgtgc ccctgcgaat    6420
cagggaccaa caggagagag ctcttgagtg ggctagtgac tcccctgca gctggtgga     6480 gatggtgtga ggagcgaaga gccctctgct ctaggatttg ggttgaaaaa cagagagaga    6540
agtggggagt tgccacagga gctaacacgc tgggaggcag ttgggggcgg gtgaactttg    6600
tgtagccgag gccgcaccct ccctcattcc aggctcattc attttcatgc tccattgcca    6660
gactcttgct gggagcccgt ccagaatgtc ctcccaataa aactccatcc tatgacgcaa    6720
aaaaaaaaaa aaaaa                                                      6736

<210> SEQ ID NO 14
<211> LENGTH: 1709
<212> TYPE: PRT
<213> ORGANISM: homo sapiens
<300> PUBLICATION INFORMATION:
<308> DATABASE ACCESSION NUMBER: GenPept/NP_075556
<309> DATABASE ENTRY DATE: 2001-02-13
<313> RELEVANT RESIDUES IN SEQ ID NO: (1)..(1709)

<400> SEQUENCE: 14

Met Gly Phe Leu Pro Lys Leu Leu Leu Ala Ser Phe Phe Pro Ala
1               5                  10                  15

Gly Gln Ala Ser Trp Gly Val Ser Ser Pro Gln Asp Val Gln Gly Val
            20                  25                  30

Lys Gly Ser Cys Leu Leu Ile Pro Cys Ile Phe Ser Phe Pro Ala Asp
        35                  40                  45

Val Glu Val Pro Asp Gly Ile Thr Ala Ile Trp Tyr Tyr Asp Tyr Ser
    50                  55                  60

Gly Gln Arg Gln Val Val Ser His Ser Ala Asp Pro Lys Leu Val Glu
65                  70                  75                  80

Ala Arg Phe Arg Gly Arg Thr Glu Phe Met Gly Asn Pro Glu His Arg
                85                  90                  95

Val Cys Asn Leu Leu Leu Lys Asp Leu Gln Pro Glu Asp Ser Gly Ser
            100                 105                 110

Tyr Asn Phe Arg Phe Glu Ile Ser Glu Val Asn Arg Trp Ser Asp Val
        115                 120                 125

Lys Gly Thr Leu Val Thr Val Thr Glu Glu Pro Arg Val Pro Thr Ile
    130                 135                 140

Ala Ser Pro Val Glu Leu Leu Glu Gly Thr Glu Val Asp Phe Asn Cys
145                 150                 155                 160

Ser Thr Pro Tyr Val Cys Leu Gln Glu Gln Val Arg Leu Gln Trp Gln
                165                 170                 175

Gly Gln Asp Pro Ala Arg Ser Val Thr Phe Asn Ser Gln Lys Phe Glu
            180                 185                 190

Pro Thr Gly Val Gly His Leu Glu Thr Leu His Met Ala Met Ser Trp
        195                 200                 205

Gln Asp His Gly Arg Ile Leu Arg Cys Gln Leu Ser Val Ala Asn His
    210                 215                 220

Arg Ala Gln Ser Glu Ile His Leu Gln Val Lys Tyr Ala Pro Lys Gly
225                 230                 235                 240

Val Lys Ile Leu Leu Ser Pro Ser Gly Arg Asn Ile Leu Pro Gly Glu
                245                 250                 255

Leu Val Thr Leu Thr Cys Gln Val Asn Ser Ser Tyr Pro Ala Val Ser
            260                 265                 270

Ser Ile Lys Trp Leu Lys Asp Gly Val Arg Leu Gln Thr Lys Thr Gly
```

-continued

```
                275                 280                 285
Val Leu His Leu Pro Gln Ala Ala Trp Ser Asp Ala Gly Val Tyr Thr
290                 295                 300
Cys Gln Ala Glu Asn Gly Val Gly Ser Leu Val Ser Pro Pro Ile Ser
305                 310                 315                 320
Leu His Ile Phe Met Ala Glu Val Gln Val Ser Pro Ala Gly Pro Ile
                325                 330                 335
Leu Glu Asn Gln Thr Val Thr Leu Val Cys Asn Thr Pro Asn Glu Ala
                340                 345                 350
Pro Ser Asp Leu Arg Tyr Ser Trp Tyr Lys Asn His Val Leu Leu Glu
                355                 360                 365
Asp Ala His Ser His Thr Leu Arg Leu His Leu Ala Thr Arg Ala Asp
370                 375                 380
Thr Gly Phe Tyr Phe Cys Glu Val Gln Asn Val His Gly Ser Glu Arg
385                 390                 395                 400
Ser Gly Pro Val Ser Val Val Asn His Pro Pro Leu Thr Pro Val
                405                 410                 415
Leu Thr Ala Phe Leu Glu Thr Gln Ala Gly Leu Val Gly Ile Leu His
                420                 425                 430
Cys Ser Val Val Ser Glu Pro Leu Ala Thr Leu Val Leu Ser His Gly
                435                 440                 445
Gly His Ile Leu Ala Ser Thr Ser Gly Asp Ser Asp His Ser Pro Arg
450                 455                 460
Phe Ser Gly Thr Ser Gly Pro Asn Ser Leu Arg Leu Glu Ile Arg Asp
465                 470                 475                 480
Leu Glu Glu Thr Asp Ser Gly Glu Tyr Lys Cys Ser Ala Thr Asn Ser
                485                 490                 495
Leu Gly Asn Ala Thr Ser Thr Leu Asp Phe His Ala Asn Ala Ala Arg
                500                 505                 510
Leu Leu Ile Ser Pro Ala Ala Glu Val Val Glu Gly Gln Ala Val Thr
                515                 520                 525
Leu Ser Cys Arg Ser Gly Leu Ser Pro Thr Pro Asp Ala Arg Phe Ser
                530                 535                 540
Trp Tyr Leu Asn Gly Ala Leu Leu His Glu Gly Pro Gly Ser Ser Leu
545                 550                 555                 560
Leu Leu Pro Ala Ala Ser Ser Thr Asp Ala Gly Ser Tyr His Cys Arg
                565                 570                 575
Ala Arg Asp Gly His Ser Ala Ser Gly Pro Ser Ser Pro Ala Val Leu
                580                 585                 590
Thr Val Leu Tyr Pro Pro Arg Gln Pro Thr Phe Thr Thr Arg Leu Asp
                595                 600                 605
Leu Asp Ala Ala Gly Ala Gly Ala Gly Arg Gly Leu Leu Leu Cys
                610                 615                 620
Arg Val Asp Ser Asp Pro Pro Ala Arg Leu Gln Leu Leu His Lys Asp
625                 630                 635                 640
Arg Val Val Ala Thr Ser Leu Pro Ser Gly Gly Gly Cys Ser Thr Cys
                645                 650                 655
Gly Gly Cys Ser Pro Arg Met Lys Val Thr Lys Ala Pro Asn Leu Leu
                660                 665                 670
Arg Val Glu Ile His Asn Pro Leu Leu Glu Glu Gly Leu Tyr Leu
                675                 680                 685
Cys Glu Ala Ser Asn Ala Leu Gly Asn Ala Ser Thr Ser Ala Thr Phe
                690                 695                 700
```

-continued

Asn Gly Gln Ala Thr Val Leu Ala Ile Ala Pro Ser His Thr Leu Gln
705                 710                 715                 720

Glu Gly Thr Glu Ala Asn Leu Thr Cys Asn Val Ser Arg Glu Ala Ala
            725                 730                 735

Gly Ser Pro Ala Asn Phe Ser Trp Phe Arg Asn Gly Val Leu Trp Ala
        740                 745                 750

Gln Gly Pro Leu Glu Thr Val Thr Leu Leu Pro Val Ala Arg Thr Asp
    755                 760                 765

Ala Ala Leu Tyr Ala Cys Arg Ile Leu Thr Glu Ala Gly Ala Gln Leu
770                 775                 780

Ser Thr Pro Val Leu Leu Ser Val Leu Tyr Pro Pro Asp Arg Pro Lys
785                 790                 795                 800

Leu Ser Ala Leu Leu Asp Met Gly Gln Gly His Met Ala Leu Phe Ile
                805                 810                 815

Cys Thr Val Asp Ser Arg Pro Leu Ala Leu Leu Ala Leu Phe His Gly
            820                 825                 830

Glu His Leu Leu Ala Thr Ser Leu Gly Pro Gln Val Pro Ser His Gly
        835                 840                 845

Arg Phe Gln Ala Lys Ala Glu Ala Asn Ser Leu Lys Leu Glu Val Arg
850                 855                 860

Glu Leu Gly Leu Gly Asp Ser Gly Ser Tyr Arg Cys Glu Ala Thr Asn
865                 870                 875                 880

Val Leu Gly Ser Ser Asn Thr Ser Leu Phe Phe Gln Val Arg Gly Ala
                885                 890                 895

Trp Val Gln Val Ser Pro Ser Pro Glu Leu Gln Glu Gly Gln Ala Val
            900                 905                 910

Val Leu Ser Cys Gln Val His Thr Gly Val Pro Glu Gly Thr Ser Tyr
        915                 920                 925

Arg Trp Tyr Arg Asp Gly Gln Pro Leu Gln Glu Ser Thr Ser Ala Thr
    930                 935                 940

Leu Arg Phe Ala Ala Ile Thr Leu Thr Gln Ala Gly Ala Tyr His Cys
945                 950                 955                 960

Gln Ala Gln Ala Pro Gly Ser Ala Thr Thr Ser Leu Ala Ala Pro Ile
                965                 970                 975

Ser Leu His Val Ser Tyr Ala Pro Arg His Val Thr Leu Thr Thr Leu
            980                 985                 990

Met Asp Thr Gly Pro Gly Arg Leu Gly Leu Leu Leu Cys Arg Val Asp
        995                 1000                1005

Ser Asp Pro Pro Ala Gln Leu Arg Leu Leu His Gly Asp Arg Leu
    1010                1015                1020

Val Ala Ser Thr Leu Gln Gly Val Gly Gly Pro Glu Gly Ser Ser
    1025                1030                1035

Pro Arg Leu His Val Ala Val Ala Pro Asn Thr Leu Arg Leu Glu
    1040                1045                1050

Ile His Gly Ala Met Leu Glu Asp Glu Gly Val Tyr Ile Cys Glu
    1055                1060                1065

Ala Ser Asn Thr Leu Gly Gln Ala Ser Ala Ser Ala Asp Phe Asp
    1070                1075                1080

Ala Gln Ala Val Asn Val Gln Val Trp Pro Gly Ala Thr Val Arg
    1085                1090                1095

Glu Gly Gln Leu Val Asn Leu Thr Cys Leu Val Trp Thr Thr His
    1100                1105                1110

Pro Ala Gln Leu Thr Tyr Thr Trp Tyr Gln Asp Gly Gln Gln Arg
    1115                1120                1125

```
Leu Asp Ala His Ser Ile Pro Leu Pro Asn Val Thr Val Arg Asp
    1130            1135                1140

Ala Thr Ser Tyr Arg Cys Gly Val Gly Pro Gly Arg Ala Pro
    1145            1150                1155

Arg Leu Ser Arg Pro Ile Thr Leu Asp Val Leu Tyr Ala Pro Arg
    1160            1165                1170

Asn Leu Arg Leu Thr Tyr Leu Leu Glu Ser His Gly Gly Gln Leu
    1175            1180                1185

Ala Leu Val Leu Cys Thr Val Asp Ser Arg Pro Ala Gln Leu
    1190            1195                1200

Ala Leu Ser His Ala Gly Arg Leu Leu Ala Ser Ser Thr Ala Ala
    1205            1210                1215

Ser Val Pro Asn Thr Leu Arg Leu Glu Leu Arg Gly Pro Gln Pro
    1220            1225                1230

Arg Asp Glu Gly Phe Tyr Ser Cys Ser Ala Arg Ser Pro Leu Gly
    1235            1240                1245

Gln Ala Asn Thr Ser Leu Glu Leu Arg Leu Glu Gly Val Arg Val
    1250            1255                1260

Ile Leu Ala Pro Glu Ala Ala Val Pro Glu Gly Ala Pro Ile Thr
    1265            1270                1275

Val Thr Cys Ala Asp Pro Ala Ala His Ala Pro Thr Leu Tyr Thr
    1280            1285                1290

Trp Tyr His Asn Gly Arg Trp Leu Gln Glu Gly Pro Ala Ala Ser
    1295            1300                1305

Leu Ser Phe Leu Val Ala Thr Arg Ala His Ala Gly Ala Tyr Ser
    1310            1315                1320

Cys Gln Ala Gln Asp Ala Gln Gly Thr Arg Ser Ser Arg Pro Ala
    1325            1330                1335

Ala Leu Gln Val Leu Tyr Ala Pro Gln Asp Ala Val Leu Ser Ser
    1340            1345                1350

Phe Arg Asp Ser Arg Ala Arg Ser Met Ala Val Ile Gln Cys Thr
    1355            1360                1365

Val Asp Ser Glu Pro Pro Ala Glu Leu Ala Leu Ser His Asp Gly
    1370            1375                1380

Lys Val Leu Ala Thr Ser Ser Gly Val His Ser Leu Ala Ser Gly
    1385            1390                1395

Thr Gly His Val Gln Val Ala Arg Asn Ala Leu Arg Leu Gln Val
    1400            1405                1410

Gln Asp Val Pro Ala Gly Asp Asp Thr Tyr Val Cys Thr Ala Gln
    1415            1420                1425

Asn Leu Leu Gly Ser Ile Ser Thr Ile Gly Arg Leu Gln Val Glu
    1430            1435                1440

Gly Ala Arg Val Val Ala Glu Pro Gly Leu Asp Val Pro Glu Gly
    1445            1450                1455

Ala Ala Leu Asn Leu Ser Cys Arg Leu Leu Gly Gly Pro Gly Pro
    1460            1465                1470

Val Gly Asn Ser Thr Phe Ala Trp Phe Trp Asn Asp Arg Arg Leu
    1475            1480                1485

His Ala Glu Pro Val Pro Thr Leu Ala Phe Thr His Val Ala Arg
    1490            1495                1500

Ala Gln Ala Gly Met Tyr His Cys Leu Ala Glu Leu Pro Thr Gly
    1505            1510                1515

Ala Ala Ala Ser Ala Pro Val Met Leu Arg Val Leu Tyr Pro Pro
```

-continued

```
       1520                1525                1530

Lys Thr Pro Thr Met Met Val Phe Val Glu Pro Glu Gly Gly Leu
    1535                1540                1545

Arg Gly Ile Leu Asp Cys Arg Val Asp Ser Glu Pro Leu Ala Ser
    1550                1555                1560

Leu Thr Leu His Leu Gly Ser Arg Leu Val Ala Ser Ser Gln Pro
    1565                1570                1575

Gln Gly Ala Pro Ala Glu Pro His Ile His Val Leu Ala Ser Pro
    1580                1585                1590

Asn Ala Leu Arg Val Asp Ile Glu Ala Leu Arg Pro Ser Asp Gln
    1595                1600                1605

Gly Glu Tyr Ile Cys Ser Ala Ser Asn Val Leu Gly Ser Ala Ser
    1610                1615                1620

Thr Ser Thr Tyr Phe Gly Val Arg Ala Leu His Arg Leu His Gln
    1625                1630                1635

Phe Gln Gln Leu Leu Trp Val Leu Gly Leu Leu Val Gly Leu Leu
    1640                1645                1650

Leu Leu Leu Leu Gly Leu Gly Ala Cys Tyr Thr Trp Arg Arg Arg
    1655                1660                1665

Arg Val Cys Lys Gln Ser Met Gly Glu Asn Ser Val Glu Met Ala
    1670                1675                1680

Phe Gln Lys Glu Thr Thr Gln Leu Ile Asp Pro Asp Ala Ala Thr
    1685                1690                1695

Cys Glu Thr Ser Thr Cys Ala Pro Pro Leu Gly
    1700                1705

<210> SEQ ID NO 15
<211> LENGTH: 40
<212> TYPE: DNA
<213> ORGANISM: Artificial Sequence
<220> FEATURE:
<223> OTHER INFORMATION: PCR forward primer CD163

<400> SEQUENCE: 15 cac cat gga caa act cag aat ggt gct aca tga aaa ctc t            40

<210> SEQ ID NO 16
<211> LENGTH: 33
<212> TYPE: DNA
<213> ORGANISM: Artificial Sequence
<220> FEATURE:
<223> OTHER INFORMATION: PCR reverse primer CD163

<400> SEQUENCE: 16 tca ttg tac ttc aga gtg gtc tcc tga ggg att                      33
```

PERMISSIVE CELLS AND USES THEREOF

FIELD OF THE INVENTION

The invention relates generally to the field of virology. More particularly, the present invention relates to methods for determining the permissiveness of a cell for a virus that is a member of the family Arteriviridae or Coronaviridae or Asfarviridae, in particular for Porcine Reproductive and Respiratory Syndrome Virus (PRRSV).

The invention further provides methods and compositions related to the generation of host cells permissive for a virus that is a member of the family Arteriviridae or Coronaviridae or Asfarviridae, in particular for Porcine Reproductive and Respiratory Syndrome Virus (PRRSV).

Methods of using said cells thus identified or thus generated, in preparing a culture of a virus that is a member of the family Arteriviridae or Coronaviridae or Asfarviridae, as well as the use of said virus for the purpose of vaccine production or diagnosis, are also provided by the present invention.

BACKGROUND TO THE INVENTION

A "mystery swine disease" appeared in the 1980's, and is present ever since in pig industry causing important economical damage worldwide (Neumann et al., 2005). The causative agent, designated porcine reproductive and respiratory syndrome virus (PRRSV), was first isolated in the Netherlands in 1991 and shortly after in the USA. It is a small enveloped positive-stranded RNA virus that is classified in the order Nidovirales, family Arteriviridae, genus Arterivirus together with equine arteritis virus, lactate dehydrogenase-elavating virus and simian hemorrhagic fever virus based on similar morphology, genomic organization, replication strategy and protein composition. In addition, they share a very narrow host tropism and a marked tropism for cells of the monocyte-macrophage lineage (Plagemann & Moennig, 1992). More specifically, in vivo PRRSV infects subpopulations of well-differentiated macrophages, with alveolar macrophages being the primary target cells, although in infected boars also testicular germ cells have been shown to allow PRRSV replication (Sur et al., 1997). In vitro, PRRSV replicates in primary cultures of alveolar macrophages and peripheral blood monocytes (PBMC), although PBMCs need treatments to improve infection (Delputte et al., 2007). Furthermore, African green monkey kidney cells and derivates thereof (Marc-145 and CL2621) have been shown to sustain PRRSV infection, although they are not from porcine origin and do not belong to the monocyte-macrophage lineage (Kim et al., 1993; Mengeling et al., 1995). Notwithstanding this very restricted cell tropism of PRRSV, the virus is able to replicate in several non-permissive cell-lines upon transfection of its viral RNA, indicating that cell tropism is determined by the presence or absence of specific receptors on the cell surface or other proteins involved in virus entry (Kreutz, 1998; Meulenberg et al., 1998).

So far, two PRRSV receptors were identified on macrophages, namely heparan sulphate (Delputte et al., 2002) and sialoadhesin (Vanderheijden et al., 2003; Wissink et al., 2003). In addition, Wissink et al. (2003) found a 150 kDa protein doublet to be involved in PRRSV infection of macrophages, however the identity of the N-glycosylated proteins is still unknown. In the current model for PRRSV infection of macrophages, PRRSV first binds to heparan sulphate most likely leading towards virus concentration. However, this first binding is rather unstable and is followed by binding to sialoadhesin and subsequent internalization (Delputte et al., 2005). Upon internalization, the virus is transported towards endosomes were a drop in pH is required for proper virus replication (Kreutz & Ackermann, 1996; Nauwynck et al., 1999). Despite this elegant research, the model is still incomplete. Transient expression of sialoadhesin in non-permissive PK-15 cells results in binding and internalization of the virus, but fusion and uncoating of the virus particles was not observed (Vanderheijden et al., 2003), indicating that other proteins are needed for virus disassembly, essential for virus replication.

PRRSV infection of Marc-145 cells makes use of a heparin-like molecule on the surface of Marc-145 cells (Jusa et al., 1997), resembling the initial step of PRRSV infection of macrophages. However, since sialoadhesin is absent from Marc-145 cells, virus entry will differ between the two cell-types. In Marc-145 cells, the intermediate filament vimentin has been described to bind to the PRRSV nucleocapsid protein and it has been suggested to interact with other cytoskeletal filaments to mediate transport of the virus in the cytosol (Kim et al., 2006). Recently, CD151 was found to interact specifically with PRRSV 3' untranslated region (UTR) RNA (Shanmukhappa et al., 2007). CD151 was proposed to be possibly involved in fusion between the viral envelope and the endosome or to relocalize the ribonucleoprotein complexes to promote viral replication. Still, further research is needed to elucidate their precise molecular modes of action during PRRSV infection.

Recently, the scavenger receptor CD163 has been described to play a role in PRRSV infection of Marc-145 cells and to make some non-permissive cells somewhat susceptible to PRRSV upon expression (Calvert et al., 2007), where others remain unproductive upon infection, despite expression of CD163 (Calvert et al., 2007). Although the CD163 gene was originally isolated from macrophages, thus far no role for CD163 in PRRSV infection of its primary target cells has been shown. Also, the mechanism by which CD163 confers partial susceptibility of selected cell types to PRRSV infection was not elucidated.

We demonstrated that both sialoadhesin and CD163 are involved in PRRSV infection of macrophages. In addition, expression of recombinant forms of both CD163 and sialoadhesin in non-permissive cells renders all of them susceptible to PRRSV infection resulting in the production and release of infectious progeny virus. In contrast, when only CD163 is present, infection is clearly less efficient, and even absent in some cell types. In addition, viral adaptation that leads to antigenic differences in viral strains grown in cells only expressing CD163 when compared to the wild type viruses, has been reported.

Based on detailed analysis of the kinetics of PRRSV infection, both in primary macrophages and in cells expressing sialoadhesin and CD163, a role for CD163 in virus fusion and uncoating is proposed. Compared to the above mentioned systems, i.e. cells solely expressing CD163 or sialoadhesin, it has been found that the combination of CD163 and sialoadhesine expression in one cell provides permissive cells that are highly efficient to sustain viral replication, and which closely mimic the entry of the virus in the natural host, i.e. the known subpopulations of well-differentiated macrophages, in particular alveolar macrophages being the primary target cells of the virus. Such mimicry of the entry of the natural target cells will certainly reduce or avoid virus adaptation in cell culture and the associated genetic and antigenic changes that might result in viruses with altered epitopes. Such modified epitopes can have tremendous effects on the antigenicity of vaccine viruses produced on given cells, resulting in loss of induction of important neutralizing antibodies. Clearly, avoiding changes in epitopes associated with adaptation during cell culture will be beneficial for production of vaccine virus.

The results presented show that Sn and CD163 work synergistically, since co-expression of both molecules results in higher virus production compared to expression of either of the two receptors alone, and this in all cell types tested. In addition, the molecular basis of this synergistic effect was elucidated, being the receptors acting at different steps during virus entry. Sn is expressed on the surface of target cells and very efficiently captures the virus and internalizes it into the cell in endosomes. CD163 on the other does not interact with the virus on the cell surface and does not internalize the virus, but co-localizes with the virus in early endosomes, where it mediates virus uncoating, followed by release of the RNA genome in the cytoplasm. Once the genome is released in the cytoplasm, genome translation, transcription and virus replication can proceed.

The finding that CD163, which is also expressed on the cell surface, does not act on the cell surface during infection, but rather interacts with the virus in endosomes inside the cell, is quite surprising. Generally, cellular receptors act during virus attachment or internalization, or direct fusion at the cell surface. This model, in which the CD163 receptor is not active on the cell surface but acts on the virus in endosomes is surprising and explains the unanticipated and cooperative action of both Sn and CD163 during virus infection, resulting in very efficient virus infection and production of high titers of virus.

Thus, these results provide new means to generate a PRRSV permissive cell that allow for efficient viral replication, with less adaptation and accordingly solves the problems recognized in the art.

SUMMARY OF THE INVENTION

This invention is based on the characterization that both sialoadhesin and CD163 are not only involved in the permissivity of macrophages, the primary target cells, for a virus that is a member of the family Arteriviridae or Coronaviridae or Asfarviridae, in particular for Porcine Reproductive and Respiratory Syndrome Virus (PRRSV), but that these molecules also act at different steps of virus infection, thus allowing a cooperative effect during infection, resulting in enhanced virus production.

It has been found that non-permissive cells can be rendered permissive, or the permissivity of partially susceptible cells can be increased by directing said cells to express both sialoadhesin and CD163.

It is accordingly a first objective of the present invention to provide methods to identify the permissiveness of cells for a virus that is a member of the family Arteriviridae or Coronaviridae or Asfarviridae, in particular for Porcine Reproductive and Respiratory Syndrome Virus (PRRSV); said method comprising determining CD163 and sialoadhesin expression in said cells; wherein cells having a both CD163 and sialoadhesin expression, are identified as permissive cells for a virus that is a member of the family Arteriviridae or Coronaviridae or Asfarviridae.

In a second objective, the present invention provides a method to generate a cell(s) permissive for, or to increase the permissiveness of a cell(s) for a virus of the family Arteriviridae or Coronaviridae or Asfarviridae, in particular for PRRSV, said method comprising treating said cells to yield an expression of both CD163 and sialoadhesin.

In a further objective, the present invention provides a method for preparing a culture of a virus that is a member of the family Arteriviridae or Coronaviridae or Asfarviridae, said method comprising providing a cell line identified or obtained using any one of the aforementioned methods, infecting said cell line with virus and harvesting the virus from the cell culture.

Once the virus has been grown to high titres, it can be processed according to the intended use, for example in diagnosis or vaccine production, by means known in the art. For example, but not limited to, inactivating the harvested viruses with formalin, BPl, BEA or gamma-irradiation, for use in vaccines. In the alternative, the viral strain used in the infection, may be an attenuated strain for use in the production of live, attenuated vaccines.

Hence it is also an embodiment of the present invention to provide a vaccine comprising a viral strain/serotype obtained using the aforementioned method. As already mentioned hereinbefore, due to the synergetic effect of CD163 and sialoadhesin, there will be a reduction in viral adaptation and loss of altered epitopes. This taken together with the increased viral production has a tremendous effect on the antigenicity of vaccine viruses produced using the methods of the present invention. As is known to a person skilled in the art, the latter is also beneficial in isolating further viral strains from in vivo samples when diagnosing PRRSV infection in a subject.

It is clearly an objective of the present invention to provide cell lines identified or obtained using any one of the aforementioned methods. Cell lines identified using the methods of the present invention include primary cell cultures and continuous cell lines obtainable thereof, but for the natural host cells, i.e. the known subpopulations of well-differentiated macrophages, in particular the alveolar macrophages that are the primary target cells of a virus that is a member of the family Arteriviridae or Coronaviridae or Asfarviridae, in particular of a PRRSV infection. In one embodiment said cells consist of non-permissive PRRSV cells, such as for example PK-15, CHO, BHK-21 and Hek293t cells, expressing both Sn and CD163; with in a particular embodiment the CHO cells stably expressing sialoadhesin and CD163 deposited on May 14, 2008 at the Belgian Coordinated Collections of Microorganisms as CHO—Sn/CD163 IC5; CHO—Sn/CD163 ID9 and CHO—Sn/CD163 IF3 with the respective accession numbers LMBP 6677CB; LMBP 6678CB; and LMBP 66779 CB respectively.

The cell lines identified or obtained using any one of the aforementioned methods, can also be used in a method of diagnosing a viral infection of a virus that is a member of the family Arteriviridae or Coronaviridae or Asfarviridae, in particular of a PRRSV infection in a subject. It is accordingly a further object of the present invention to provide a method for diagnosing a viral infection of a virus that is a member of the family Arteriviridae or Coronaviridae or Asfarviridae, in particular of a PRRSV infection in a subject, said method comprising contacting a cell line identified or obtained using any one of the methods of the present invention with a sample taken from said subject and determine whether viral replication occurs.

Alternatively, the viral infection is determined by assessing the presence of virus-specific antibodies in the sample taken from said subject. In this embodiment the cell line identified or obtained using any one of the methods of the present invention is infected with a virus of the family Arteriviridae or Coronaviridae or Asfarviridae, in particular with PRRSV, and the reaction of the antibodies in a sample taken from said subject is done by means well known to the person skilled in the art.

In these diagnostic methods the sample taken from the subject, is typically a biological fluid; such as for example serum, colostrums, bronchoalveolar lavage fluids, saliva, urine or faeces; tissue or a tissue extract. The tissue or tissue extract to be analyzed includes those which are known, or suspected, to be permissive for the virus such as, for example PBMC (peripheral blood mononuclear cells), alveolar macrophages, lymphoid tissues such as lymph nodes, spleen, tonsils and thymus and non-lymphoid tissues such as lungs and liver.

In a final embodiment the cell lines identified or obtained using any one of the aforementioned methods, can be used in a method to identify anti-viral compounds, i.e. anti-viral compounds for a virus of the family Arteriviridae or Coronaviridae or Asfarviridae as defined herein, in particular for PRRSV. The invention accordingly provides in a further objective, a method to identify anti-viral compounds, said method comprising;—contacting a cell line infected with a virus of the Arteriviridae or Coronaviridae or Asfarviridae, with the compound to be tested; and determine the capability of said test compound to modulate the viral replication in said cell line.

The capability of a compound to modulate the viral replication can be determined by using amongst others, the presence of infectious viral particles in the media. The latter can be determined using any one of the available protein measurement techniques and is typically determined using late viral specific antibodies, in particular using (virus) specific antibodies as provided hereinafter.

In the immunoassays related thereto, the amount of viral protein produced can be quantified by any standard assay such as, for example, using a luminescence assay, a chemiluminesence assay, an enzyme-multiplied immunoassay technology (EMIT) assay, a fluorescence resonance excitation transfer immunoassay (FRET) assay, an enzyme channeling immunoassay (ECIA) assay, a substrate-labeled fluorescent immunoassay (SLFIA) assay, a fluorescence polarization assay, a fluorescence protection assay, an antigen-labeled fluorescence protection assay (ALFPIA), or scintillation proximity assay (SPA).

Alternatively, the effect of the compound on viral replication is determined by assessing the virus titres in the media, by quantifying numbers of infected cells by immunocytochemistry or by using a MTS cytotoxicity assay to determine the cytotoxic concentration of the viral particals in the media.

DESCRIPTION OF THE INVENTION

Figure 1:
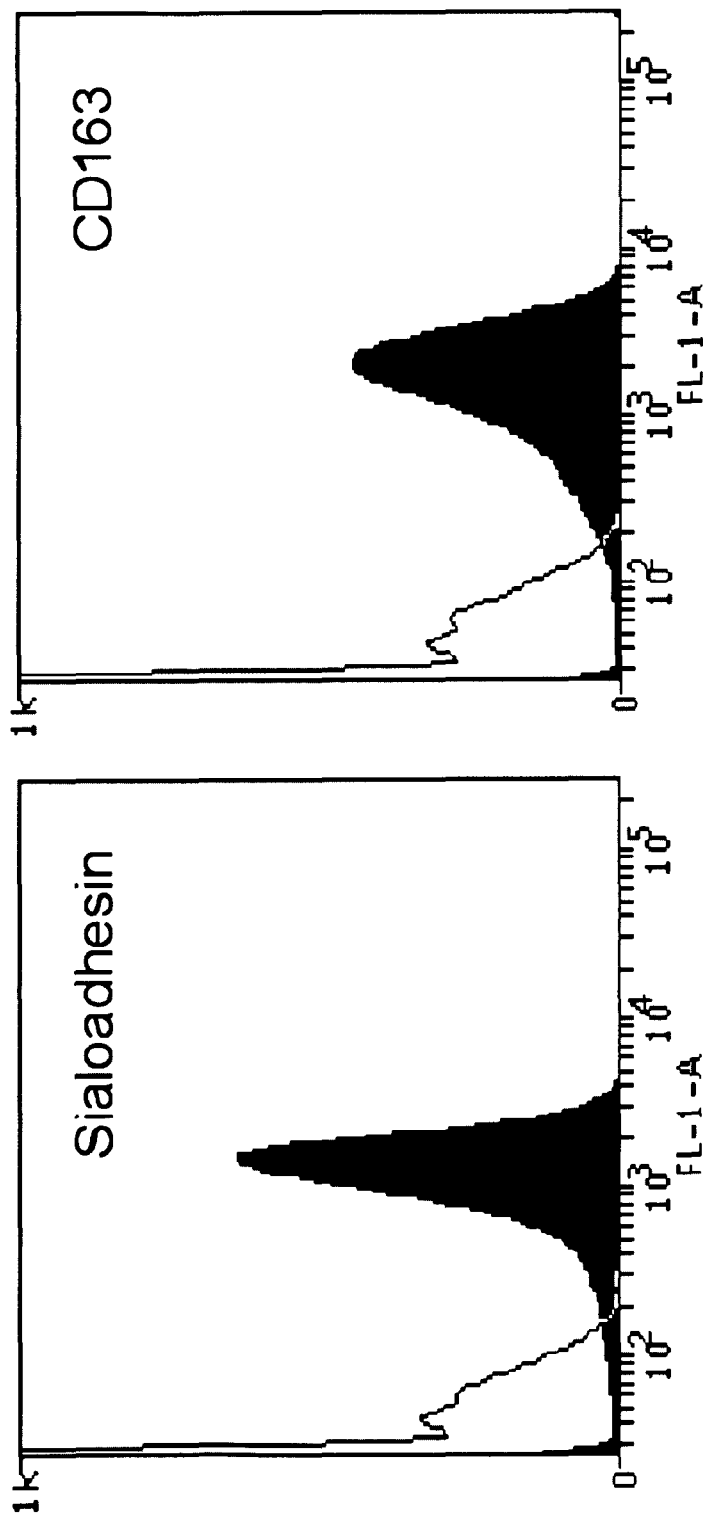
FIG. 1 Expression of sialoadhesin and CD163 on primary alveolar macrophages.
  Flow cytometric analysis of macrophages stained with mAb 41D3 for porcine sialoadhesin (black curve) or mAb 2A10 for porcine CD163 (black curve). In both experiments, the isotype-matched (IgG1) antibody 13D12 (white curve) was used as control.

As already mentioned hereinbefore, the present invention is based on the observation that both sialoadhesin and CD163 are involved in the permissivity of macrophages, the primary target cells, for a virus that is a member of the family Arteriviridae or Coronaviridae or Asfarviridae, in particular for Porcine Reproductive and Respiratory Syndrome Virus (PRRSV). In addition, and surprisingly, it was shown that CD163 does not act at the cell surface of susceptible cells during attachment and internalization, but rather acts during virus uncoating and genome release inside the cell in endosomes. This unexpected finding explains why CD163 acts synergistically with Sn during virus infection, since the latter interacts with the virus at the cell surface to allow virus attachment and internalization.

It is accordingly a first objective of the present invention to provide methods to identify the permissiveness of cells for a virus that is a member of the family Arteriviridae or Coronaviridae or Asfarviridae, in particular for Porcine Reproductive and Respiratory Syndrome Virus (PRRSV); said method comprising determining CD163 and sialoadhesin expression in said cells; wherein cells having a both CD163 and sialoadhesin expression, are identified as permissive cells for a virus that is a member of the family Arteriviridae or Coronaviridae or Asfarviridae.

Asfarviridae is a family of icosohedral enveloped viruses whose genome consists of a single molecule of linear double-stranded DNA of about 150000-190000 nucleotides long. The name of the family is derived from African Swine Fever And Related Viruses. African Swine Fever Virus (ASFV) is the type species of the Asfivirus genus and is the sole member of the family. Recently, porcine CD163 polypeptide has been surmised by implication to be the cellular receptor for African swine fever virus (ASFV) (Sanchez-Torres et al., 2003).

The Arteriviridae family is grouped with the Coronaviridae and Roniviridae to form the order Nidovirales. All members of the order have enveloped particles containing a single species of single-stranded RNA that encodes for a number of proteins by means of a series of nested (Latin Nido=nest) subgenomic RNAs. The family Arteriviridae contains those members with spherical virions 45-60 nm in diameter (those of the family Coronaviridae are more than 100 nm) and which infect mammals. Their genome consists of single-stranded RNA of size 12-16 kb and with a 3'-polyA tail. Two large, overlapping ORFs at the 5'-end of the genome encode the major non-structural proteins and are expressed as a fusion protein by ribosomal frameshift. Downstream are up to 9 other genes, mostly or entirely encoding structural proteins, and these are expressed from a 3'-coterminal nested set of subgenomic RNAs.

Viruses of the family of Arteriviridae includes equine arteritis virus (EAV), lactate dehydrogenase-elevating virus (LDV) and simian hemorrhagic fever virus (SHFV). The Arterivirus having the greatest economic importance is Porcine Reproductive and Respiratory Syndrome Virus (PRRSV).

Thus in one objective, the methods of the present invention are used to identify and/or modulate the permissivity of cells for a virus selected from the group consisting of African swine fever virus (ASFV), equine arteritis virus (EAV), lactate dehydrogenase-elevating virus (LDV), simian hemorrhagic fever virus (SHFV) or porcine reproductive and respiratory syndrome virus (PRRSV), as well as variants thereof including orthologs and paralogs; in particular human orthologs. In a particular embodiment the methods of the present invention are used to identify and/or modulate the permissivity of cells for PRRSV.

As used herein, the terms "permissiveness of a cell(s)", "permissivity of cell(s)" and "permissive cell(s)" refers to the ability in which a particular virus, i.e. a virus that is a member of the family Arteriviridae or Coronaviridae or Asfarviridae, can complete its replication cycle in a given cell. This in contrast to "non-permissive" cells that do not support complete replication of a virus.

"CD163" is a member of the scavenger receptor cysteine-rich (SRCR) family of transmembrane glycoproteins, and is thought to be expressed exclusively on monocytes and macrophages. One identified role of CD 163 is to inhibit oxidative tissue damage following hemolysis by consuming hemoglobin:haptoglobin complexes by endocytosis. The subsequent release of interleukin-10 and synthesis of hemeoxygenase-1 results in antiinflammatory and cytoprotective effects. The human CD163 gene spans 35 kb on chromosome 12, and consists of 17 exons and 16 introns.

A number of isoforms of the CD163 polypeptide, including membrane bound, cytoplasmic and secreted types, are known to be generated by alternative splicing (Ritter et al., 1999). cDNA sequences that encodes a porcine CD 163 polypeptide (Genbank accession number AJ311716), a murine CD 163 polypeptide (Genbank access number AF274883), as well as multiple human variants, exemplified by Genbank access numbers AAH51281 and CAA80543, have been reported.

As used herein the "CD163" polypeptide is meant to be a protein encoded by a mammalian CD 163 gene, including allelic variants as well as biologically active fragments thereof containing conservative or non-conservative changes as well as artificial proteins that are substantially identical, i.e. 70%, 75%, 80%, 85%, 87%, 89%, 90%, 92%, 93%, 94%, 95%, 96%, 97%, 98%, or 99% identical to any one of the aforementioned CD 163 polypeptides. In a particular embodiment the CD 163 polypeptide is 70%, 75%, 80%, 85%, 87%, 89%, 90%, 92%, 93%, 94%, 95%, (CO, 97%, 98%, or 99% identical to the porcine CD 163 (encoded by Genbank Accession N° AJ311716 or bankit927381 EU016226).

By analogy, the "CD163" polynucleotide is meant to include allelic variants as well as biologically active fragments thereof containing conservative or non-conservative changes as well as any nucleic acid molecule that is substantially identical, i.e. 70%, 75%, 80%, 85%, 87%, 89%, 90%, 92%, 93%, 94%, 95%, 96%, 97%, 98%, or 99% identical to any one of the aforementioned CD163 encoding polynucleotides. In a particular embodiment the sialoadhesin polynucleotide is 70%, 75%, 80%, 85%, 87%, 89%, 90%, 92%, 93%, 94%, 95%, 96%, 97%, 98%, or 99% identical to the nucleic acid molecule encoding for porcine CD163 (Genbank Accession N° AJ311716 or bankit927381 EU016226).

Biologically active fragments of CD163 are meant to include fragments that retain the activity of the full length protein, such as the isoform with SwissProt accession number Q2VL90-2, the soluble form of CD163 (sCD163), or fragments containing at least 1, 2, 3, 4, 5, 6, 7, 8 or 9 of the SRCR domain(s).

"Sialoadhesin" is a lectin-like adhesion shown to bind glycoconjugate ligands in a sialic acid-dependent manner and characterized in having conserved sialic acid binding sites. It is a transmembrane glycoprotein involved in cell-cell interactions and expressed only by a subpopulation of tissue macrophages.

cDNA sequences that encodes a porcine sialoadhesin polypeptide (Genbank accession number NM_214346), a murine sialoadhesin polypeptide (Genbank access number NM_011426), as well as a human variant (Genbank access number NM_023068), have been reported.

As used herein the "sialoadhesin" polypeptide is meant to be a protein encoded by a mammalian sialoadhesin gene, including allelic variants as well as biologically active fragments thereof containing conservative or non-conservative changes as well as artificial proteins that are substantially identical, i.e. 70%, 75%, 80%, 85%, 87%, 89%, 90%, 92%, 93%, 94%, 95%, 96%, 97%, 98%, or 99% identical to any one of the aforementioned sialoadhesin polypeptides. In a particular embodiment the sialoadhesin polypeptide is 70%, 75%, 80%, 85%, 87%, 89%, 90%, 92%, 93%, 94%, 95%, 96%, 97%, 98%, or 99% identical to the porcine sialoadhesin (encoded by Genbank Accession N° NM_214346).

By analogy, the "sialoadhesin" polynucleotide is meant to include allelic variants as well as biologically active fragments thereof containing conservative or non-conservative changes as well as any nucleic acid molecule that is substantially identical, i.e. 70%, 75%, 80%, 85%, 87%, 89%, 90%, 92%, 93%, 94%, 95%, 96%, 97%, 98%, or 99% identical to any one of the aforementioned sialoadhesin encoding polynucleotides. In a particular embodiment the sialoadhesin polynucleotide is 70%, 75%, 80%, 85%, 87%, 89%, 90%, 92%, 93%, 94%, 95%, 96%, 97%, 98%, or 99% identical to the nucleic acid molecule encoding for porcine sialoadhesin (Genbank Accession N° NM_214346).

Biologically active fragments of sialoadhesin are meant to include fragments that retain the activity of the full length protein, i.e. that retain the capability of binding a virus of the family of Arteriviridae includes equine arteritis virus (EAV), lactate dehydrogenase-elevating virus (LDV) and simian hemorrhagic fever virus (SHFV), in particular of binding PRRSV. Biologically active fragments include for example, the known soluble form of sialoadhesin, fragments containing at least 1, 2, 3 or 4 of the Ig-like domain(s); in particular the N-terminal domains; more in particular consisting of the N-terminal, variable, sialic acid-binding Ig-like domain.

As used herein, the terms "polynucleotide" and "nucleic acid" are used interchangeably to refer polynucleotides of any length, either deoxyribonucleotides or ribonucleotides or analogs (e.g., inosine, 7-deazaguanosine, etc.) thereof. "Oligonucleotides" refer to polynucleotides of less than 100 nucleotides in length, preferably less than 50 nucleotides in length, and most preferably about 10-30 nucleotides in length. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can include modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

"Polypeptide" refers to any peptide or protein comprising amino acids joined to each other by peptide bonds or modified peptide bonds. "Polypeptide" refers to both short chains, commonly referred to as peptides, oligopeptides or oligomers, and to longer chains, generally referred to as proteins. Polypeptides may contain amino acids other than the 20 gene-encoded amino acids.

"Polypeptides" include amino acid sequences modified either by natural processes, such as post-translational processing, or by chemical modification techniques which are well known in the art. Such modifications are well described in basic texts and in more detailed monographs, as well as in a voluminous research literature.

Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications (see, for instance, Proteins-Structure and Molecular Properties, 2nd Ed., T. E. Creighton, W. H. Freeman and Company, New York, 1993; Wold, F., Post-translational Protein Modifications: Perspectives and Prospects, pgs. 1-12 in Postranslational Covalent Modification of Proteins, B. C. Johnson, Ed., Academic Press, New York, 1983; Seifter et al., "Analysis for protein modifications and nonprotein cofactors", Meth Enzymol (1990) 182: 626-646 and Rattan et al., "Protein Synthesis: Post-translational Modifications and Aging", Ann NY Acad Sci (1992) 663: 4842).

Sequence Identity

The percentage identity of nucleic acid and polypeptide sequences can be calculated using commercially available algorithms which compare a reference sequence with a query sequence. The following programs (provided by the National Center for Biotechnology Information) may be used to determine homologies/identities: BLAST, gapped BLAST, BLASTN and PSI-BLAST, which may be used with default parameters.

The algorithm GAP (Genetics Computer Group, Madison, Wis.) uses the Needleman and Wunsch algorithm to align two complete sequences that maximizes the number of matches and minimizes the number of gaps. Generally, the default parameters are used, with a gap creation penalty=12 and gap extension penalty=4.

Another method for determining the best overall match between a nucleic acid sequence or a portion thereof, and a query sequence is the use of the FASTDB computer program based on the algorithm of Brutlag et al (Comp. App. Biosci., 6; 237-245 (1990)). The program provides a global sequence alignment. The result of said global sequence alignment is in percent identity. Suitable parameters used in a FASTDB search of a DNA sequence to calculate percent identity are: Matrix=Unitary, k-tuple=4, Mismatch penalty=1, Joining Penalty=30, Randomization Group Length=0, Cutoff Score=1, Gap Penalty=5, Gap Size Penalty=0.05, and Window Size=500 or query sequence length in nucleotide bases, whichever is shorter. Suitable parameters to calculate percent identity and similarity of an amino acid alignment are: Matrix=PAM 150, k-tuple=2, Mismatch Penalty=1, Joining Penalty=20, Randomization Group Length=0, Cutoff Score=1, Gap Penalty=5, Gap Size Penalty=0.05, and Window Size=500 or query sequence length in nucleotide bases, whichever is shorter.

CD163 and Sialoadhesin Expression

The "expression" generally refers to the process by which polynucleotides are transcribed into mRNA and/or the process by which the mRNA is subsequently translated into peptides, polypeptides or proteins. Hence the "expression" of a gene product, in the present invention of CD163 and sialoadhesin, can be determined either at the nucleic acid level or the protein level.

Detection can be by any appropriate method, including, e.g., detecting the quantity of mRNA transcribed from the gene or the quantity of nucleic acids derived from the mRNA transcripts. Examples of nucleic acids derived from an mRNA include a cDNA produced from the reverse transcription of the mRNA, an RNA transcribed from the cDNA, a DNA amplified from the cDNA, an RNA transcribed from the amplified cDNA, and the like. In order to detect the level of mRNA expression, the amount of the derived nucleic acid should be proportional to the amount of the mRNA transcript from which it is derived. The mRNA expression level of a gene can be detected by any method, including hybridization (e.g., nucleic acid arrays, Northern blot analysis, etc.) and/or amplification procedures according to methods widely known in the art. For example, the RNA in or from a sample can be detected directly or after amplification. Any suitable method of amplification may be used. In one embodiment, cDNA is reversed transcribed from RNA, and then optionally amplified, for example, by PCR. After amplification, the resulting DNA fragments can for example, be detected by agarose gel electrophoresis followed by visualization with ethidium bromide staining and ultraviolet illumination. A specific amplification of differentially expressed genes of interest can be verified by demonstrating that the amplified DNA fragment has the predicted size, exhibits the predicated restriction digestion pattern and/or hybridizes to the correct cloned DNA sequence.

In hybridization methods a probe, i.e. nucleic acid molecules having at least 10 nucleotides and exhibiting sequence complementarity or homology to the nucleic acid molecule to be determined, are used. It is known in the art that a "perfectly matched" probe is not needed for a specific hybridization. A probe useful for detecting mRNA is at least about 80%, 85%, 90%, 95%, 97% or 99% identical to the homologous region in the nucleic acid molecule to be determined. In one aspect, a probe is about 50 to about 75, nucleotides or, alternatively, about 50 to about 100 nucleotides in length. These probes can be designed from the sequence of full length genes. In certain embodiments, it will be advantageous to employ nucleic acid sequences as described herein in combination with an appropriate label for detecting hybridization and/or complementary sequences. A wide variety of appropriate labels, markers and/or reporters are known in the art, including fluorescent, radioactive, enzymatic or other ligands, such as avidin/biotin, which are capable of giving a detectable signal. One can employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a signal that is visible to the human eye or spectrophotometrically, to identify specific hybridization with complementary nucleic acid-containing samples.

Detection of the level of gene expression can also include detecting the quantity of the polypeptide or protein encoded by the gene. A variety of techniques are available in the art for protein analysis. They include but are not limited to radioimmunoassay (RIA), ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays and PAGE-SDS. One method to determine protein level involves (a) providing a biological sample containing polypeptides; and (b) measuring the amount of any immunospecific binding that occurs between an antibody reactive to the expression product of a gene of interest and a component in the sample, in which the amount of immunospecific binding indicates the level of the expressed proteins. Antibodies that specifically recognize and bind to the protein products of these genes are required for these immunoassays. These may be purchased from commercial vendors or generated and screened using methods well known in the art. See e.g., Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel et al. eds., (1987)); the series METHODS IN ENZYMOLOGY (Academic Press, Inc.): PCR 2: A PRACTICAL APPROACH (M J. MacPherson, B. D. Hames and G. R. Taylor eds. (1995)), Harlow and Lane, eds. (1988) ANTIBODIES, A LABORATORY MANUAL and ANIMAL CELL CULTURE (R. I. Freshney, ed. (1987)).

In a second objective, the present invention provides a method to generate a cell(s) permissive for, or to increase the permissiveness of a cell(s) for a virus of the family Asfarviridae or Arteriviridae, in particular for PRRSV, said method comprising treating said cells to yield an expression of both CD163 and sialoadhesin.

CD 163 and sialoadhesin expression may be facilitated or increased by methods that involve the introduction of exogenous nucleic acid into the cell. Such a cell may comprise a polynucleotide or vector in a manner that permits expression of an encoded CD 163 or sialoadhesin polypeptide.

Polynucleotides that encode CD 163 or sialoadhesin may be introduced into the host cell as part of a circular plasmid, or as linear DNA comprising an isolated protein-coding region, or in a viral vector. Methods for introducing exogenous nucleic acid into the host cell well known and routinely practiced in the art include transformation, transfection, electroporation, nuclear injection, or fusion with carriers such as liposomes, micelles, ghost cells, and protoplasts. Host cell systems of the invention include plant, invertebrate and vertebrate cells systems. Hosts may include, but are not limited to, the following: insect cells, porcine kidney (PK) cells, feline kidney (FK) cells, swine testicular (ST) cells, African green monkey kidney cells (MA-104, MARC-145, VERO, and COS cells), Chinese hamster ovary (CHO) cells, baby hamster kidney cells, human 293 cells, and murine 3T3 fibroblasts. Insect host cell culture systems may also be used for the expression of the polypeptides according to the invention. In another embodiment, the polypeptides are expressed using a *drosophila* expression system. Alternatively the polypeptides are expressed using plant-based production platforms such as for example described in Twyman R. M. et al., Molecular farming in plants: host systems and expression technology *Trends Biotechnol.* 21, 570-578.

The choice of a suitable expression vector for expression of the polypeptides according to the invention will of course depend upon the specific host cell to be used, and is within the skill of the ordinary artisan. Examples of suitable expression vectors include pSport and pcDNA3 (Invitrogen), pCMV-Script (Stratagene), and pSVL (Pharmacia Biotech). Expression vectors for use in mammalian host cells may include transcriptional and translational control sequences derived from viral genomes. Commonly used promoter sequences and modifier sequences which may be used in the present invention include, but are not limited to, those derived from human cytomegalovirus (CMV), Rous sarcoma virus (RSV), Adenovirus 2, Polyoma virus, and Simian virus 40 (SV40). Methods for the construction of mammalian expression vectors are disclosed, for example, in Okayama and Berg (Mol. Cell. Biol. 3:280 (1983)); Cosman et al. (Mol. Immunol. 23:935 (1986)); Cosman et al. (Nature 312:768 (1984)); EP-A-0367566; and WO 91/18982.

Because CD163 sequences are known to exist in cells from various species, the endogenous gene may be modified to permit, or increase, expression of the CD 163 polypeptide. Cells can be modified (e.g., by homologous recombination) to provide increased expression by replacing, in whole or in part, the naturally occurring CD163 promoter with all or part of a heterologous promoter, so that the cells express CD 163 polypeptide at higher levels. The heterologous promoter is inserted in such a manner that it is operatively linked to endogenous CD163 encoding sequences. [See, for example, PCT International Publication No. WO 94/12650, PCT International Publication No. WO 92/20808, and PCT International Publication No. WO 91/09955.] It is also contemplated that, in addition to heterologous promoter DNA, amplifiable marker DNA (e.g., ada, dhfr, and the multifunctional cad gene, which encodes for carbamyl phosphate synthase, aspartate transcarbamylase, and dihydroorotase) and/or intron DNA may be inserted along with the heterologous promoter DNA. If linked to the CD 163 coding sequence, amplification of the marker DNA by standard selection methods results in co-amplification of the CD163 coding sequences in the cells.

CD163 expression may also be induced by chemical treatment. Phorbol esters, especially phorbol myristyl acetate (PMA), activate one or more isozymes of the ubiquitous membrane receptor, protein kinase C (PKC) and are particularly preferred means of increasing CD163 expression. Other methods of intracellular calcium mobilization are also contemplated.

Sialoadhesin expression may also be induced by chemical treatment. It has been reported that IFN-α does increase and is even capable to induce sialoadhesin expression in the monocyte-macrophage lineage of cells. Thus IFN-α treatment is an alternative means of increasing/inducing sialoadhesin expression in a cell.

Cell Lines

The cell lines identified or obtained using the methods of the present invention are clearly a further object of the present invention.

In a first embodiment these cell lines consist of primary cell cultures of cells identified as being permissive for a virus of the family Asfarviridae or Arteriviridae, in particular for PRRSV, provided said cells are not the natural host cells, i.e. the known subpopulations of well-differentiated macrophages, in particular the alveolar macrophages that are the primary target cells of a virus that is a member of the family Arteriviridae or Coronaviridae or Asfarviridae, in particular of a PRRSV infection.

Cells that are cultured directly from an animal or person are known as "primary cells". With the exception of some derived from tumours, most primary cell cultures have limited lifespan. After a certain number of population doublings cells undergo the process of senescence and stop dividing, while generally retaining viability. Methods for growing suspension and adhesion cultures of primary cells are known to the person skilled in the art, such as for example described in "General Techniques of Cell Culture", Maureen A. Harrison and Ian F. Rae, Cambridge University Press 2007.

As used in the methods of the present invention, the "primary cells" are derived from; cells that support the replication of said viruses, in particular of PRRSV. In one embodiment, said cells consist of the known subpopulations of differentiated cells of the monocyte/macrophage lineage, in particular the alveolar macrophages that are the primary target cells of a virus that is a member of the family Arteriviridae or Coronaviridae or Asfarviridae, in particular of a PRRSV infection. In particular embodiments of the present invention, the "primary cells" are derived from the alveolar macrophages that are the primary target cells This in contrast to "continuous cells" also known as "an established" or "immortalized" cell line that has acquired the ability to proliferate indefinitely either through random mutation or deliberate modification, such as artificial expression of the telomerase gene. There are numerous well established cell lines representative of particular cell types.

In the context of the present invention, the continuous cells are either derived by immortalization from the primary cell cultures mentioned herein before or obtained from a well established continuous cell line treated, in particular by transfection with a nucleic acid sequence encoding CD163 and/or sialoadhesin, to yield a stable expression of both CD163 and sialoadhesin. In an alternative embodiment the CD163 expression may also be induced by chemical treatment in continuous cell lines stably expressing Sn. Phorbol esters, especially phorbol myristyl acetate (PMA), activate one or more isozymes of the ubiquitous membrane receptor, protein kinase C (PKC) and are particularly preferred means of increasing CD163 expression. Other methods of intracellular calcium mobilization are also contemplated. In analogy, continuous cells stably expressing CD163 may also be induced to express Sn by chemical treatment, using for example IFN-α.

Examples of continuous cell lines derived from the monocyte/macrophage lineage and useful in the context of the present invention are THP-1, MM-1, J774, SU-DHL, RAW264, 3D4, and others.

Several established methods exist for immortalizing mammalian cells in culture. Viral genes, including Epstein-Barr virus (EBV), Simian virus 40 (SV40) T antigen, adenovirus E1A and E1B, and human papillomavirus (HPV) E6 and E7 can induce immortalization by a process known as viral transformation. Although the process is reliable and relatively simple, these cells may become genetically unstable (aneuploid) and lose the properties of primary cells. For the most part, these viral genes achieve immortalization by inactivating the tumor suppressor genes that put cells into a replicative senescent state. The preferred method to immortalize cells is through expression of the telomerase reverse transcriptase protein (TERT), particularly those cells most affected by telomere length (e.g., human). This protein is inactive in most somatic cells, but when hTERT is exogenously expressed the cells are able to maintain telomere lengths sufficient to avoid replicative senescence. Analysis of several telomerase-immortalized cell lines has verified that the cells maintain a stable genotype and retain critical phenotypic markers.

The well established continuous cells used herein are typically selected from the group consisting of cells with leukocyte characteristics or non-leukocyte cells such as for example swine testicle cells, swine kidney cells (e.g. PK15 (CCL-33), SK-RST(CRL-2842)), epithelial cell cultures, skin keratinocytes (e.g. HEK001 (CRL-2404), CCD1102 (CRL-2310)), Vero cells (CCL-81), human fetal lung fibroblasts (e.g. HFL1 (CCL-153)), human embryonic lung cells (e.g. HEL299 (CCL-137)), Chinese Hamster Ovary cells (CHO) or human embryonic kidney cells (HEK).

Hence in a further embodiment the cell lines consist of continuous cells expressing both CD163 and sialoadhesin.

Virus Culture and Vaccines

In a further objective, the present invention provides a method for preparing a culture of a virus that is a member of the family Arteriviridae or Coronaviridae or Asfarviridae, said method comprising providing a cell line identified or obtained using any one of the aforementioned methods, infecting said cell line with virus and harvesting the virus from the cell culture.

Once the virus has been grown to high titres, it can be processed according to the intended use, for example in diagnosis or vaccine production, by means known in the art.

For example, in case of vaccine production, the harvested viruses may be inactivated for example with formalin, BPI, BEA or gamma-irradiation, for use in vaccines. In the alternative, the viral strain used in the infection, may be an attenuated strain for use in the production of live, attenuated vaccines.

Hence it is also an embodiment of the present invention to provide a vaccine comprising a viral strain/serotype obtained using the aforementioned method.

Killed (inactivated) or live vaccines can be produced. To make a live vaccine, a viral isolate, or an attenuated or mutated variant thereof, is grown in cell culture. The virus is harvested according to methods well known in the art. The virus may then be concentrated, frozen, and stored at −70° C., or freeze-dried and stored at 4° C. Prior to vaccination the virus is mixed at an appropriate dosage, (which is from about 10 to $10^8$ tissue culture infectious doses per ml), with a pharmaceutically acceptable carrier such as a saline solution, and optionally an adjuvant.

The vaccine produced might also comprise an inactivated or killed vaccine comprising a PRRSV strain obtained by the methods of the invention. The inactivated vaccine is made by methods well known in the art. For example, once the virus is propagated to high titers, it would be readily apparent by those skilled in the art that the virus antigenic mass could be obtained by methods well known in the art. For example, the virus antigenic mass may be obtained by dilution, concentration, or extraction. All of these methods have been employed to obtain appropriate viral antigenic mass to produce vaccines. The virus is then inactivated by treatment with formalin, betapropriolactone (BPL), binary ethyleneimine (BEI), or other methods known to those skilled in the art. The inactivated virus is then mixed with a pharmaceutically acceptable carrier such as a saline solution, and optionally an adjuvant. Examples of adjuvants include, but not limited to, aluminum hydroxide, oil-in-water and water-in-oil emulsions, AMPHIGEN, saponins such as QuilA, and polypeptide adjuvants including interleukins, interferons, and other cytokines.

Inactivation by formalin is performed by mixing the viral suspension with 37% formaldehyde to a final formaldehyde concentration of 0.05%. The virus-formaldehyde mixture is mixed by constant stirring for approximately 24 hours at room temperature. The inactivated virus mixture is then tested for residual live virus by assaying for growth on a suitable cell line.

Inactivation by BEI is performed by mixing the viral suspension of the present invention with 0.1 M BEI (2-bromo-ethylamine in 0.175 N NaOH) to a final BEI concentration of 1 mM. The virus-BEI mixture is mixed by constant stirring for approximately 48 hours at room temperature, followed by the addition of 1.0 M sodium thiosulfate to a final concentration of 0.1 mM. Mixing is continued for an additional two hours. The inactivated virus mixture is tested for residual live virus by assaying for growth on a suitable cell line.

The present invention now has as its object to provide the use of a virus, of an inactivated virus or of a vaccine of the present invention for preparing a medicament which is employed for the prophylactic and/or therapeutic treatment of PRRSV infection in animals, in particular in swine and piglets.

The vaccine used according to the invention advantageously is provided in a suitable formulation. Preferred are such formulations with a pharmaceutically acceptable carrier. This comprises, e.g., auxiliary substances, buffers, salts, preservatives.

Diagnosis

In the diagnostic methods, the permissive cells of the present invention are contacted with a sample taken from an infected subject; the cells cultured to allow replication of the virus; the virus harvested from said cell culture and identified using art known procedures, such as for example using specific antibodies for a virus that is a member of the family Arteriviridae or Coronaviridae or Asfarviridae, in particular for PRRSV.

The (virus) specific antibody is in particular a monoclonal antibody or a derivative thereof, the latter preferably selected from the group of antibody fragments, conjugates or homologues, but also complexes and absorbates known to the skilled artisan. In a particular embodiment the (virus) specific antibodies are selected from the group consisting of PRRSV nucleocapsid-specific antibodies such as P3/27 and SDOW17 and WBE1, 4, 5 and 6.

In the alternative, the present invention provides the use of the viruses harvested from the above mentioned cell cultures in methods to determine a viral infection or a previous viral infection in a subject, by assessing the presence of virus-specific antibodies in the sample taken from said subject, i.e. detecting the binding of said virus-specific antibodies to the viruses harvested from the cell culture or the binding of the virus-specific antibodies to the viral protein-expressing infected cells.

A variety of techniques are available in the art to determine binding of the virus-specific antibodies to the virus. They include but are not limited to radioimmunoassay (RIA), ELISA (enzyme linked immunoradiometric assays), "sandwich" immunoassays, "competition" immunoassays, immunoradiometric assays, in situ immunoassays (using e.g., colloidal gold, enzyme or radioisotope labels), western blot analysis, immunoprecipitation assays, immunofluorescent assays and PAGE-SDS.

In a particular embodiment, the presence of virus-specific antibodies will be determined using a typical competition or sandwich assay. For example, in a sandwich assay the binding of the virus-specific antibodies is done using a secondary labeled antibody, which is reactive for the primary virus-specific antibody and preferably has the ability to react with multiple sites on the primary antibody. In a competition assay a standard amount of a labeled virus-specific antibody will compete with the antibodies present in the sample for binding to the virus.

Known labels are of the radioactive or fluorometric type, which are detected by instrumentation, and colorimetric labels, typically enzyme labels which cause the conversion of a corresponding substrate to colored form.

Enzymes have often been used as labels in immunoassay. In conventional enzyme immunoassay (EIA), an enzyme is covalently conjugated with one component of a specifically binding antigen-antibody pair, and the resulting enzyme conjugate is reacted with a substrate to produce a signal which is detected and measured. The signal may be a color change, detected with the naked eye or by a spectrophotometric technique, or may be conversion of the substrate to a product detected by fluorescence.

It is accordingly an object of the present invention to provide a method to determine a viral infection or a previous viral infection in a subject, said method comprising;
- harvesting a virus that is a member of the family Arteriviridae or Coronaviridae or Asfarviridae, in particular for PRRSV, from a cell culture obtainable using any one of the methods of the present invention; contacting said virus with a sample taken from said subject; and
- determine the presence of virus-specific antibodies in the sample taken from said subject.

In any one of the diagnostic methods, mentioned hereinbefore, the sample is typically a biological fluid; such as for example serum, colostrums, bronchoalveolar lavage fluids, saliva, urine or faeces; tissue or a tissue extract. The tissue or tissue extract to be analyzed includes those which are known, or suspected, to be permissive for the virus such as, for example PBMC (peripheral blood mononuclear cells), alveolar macrophages, lymphoid tissues such as lymph nodes, spleen, tonsils and thymus and non-lymphoid tissues such as lungs and liver.

This invention will be better understood by reference to the Experimental Details that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXAMPLES

The following examples illustrate the invention. Other embodiments will occur to the person skilled in the art in light of these examples.

Methods

Cell Culture and Transfection

Primary alveolar macrophages were obtained from 4- to 6-week old conventional Belgian Landrace pigs from a PRRSV-negative herd as described by Wensvoort et al. (Wensvoort et al., 1991), and cultivated in RPMI 1640 supplemented with 10% fetal bovine serum (FBS), 1% nonessential amino acids and 1 mM sodium pyruvate. Marc-145 cells were cultivated in Minimum Essential Medium with Earle's salts (MEM) supplemented with 5% FBS. PK-15 cells were grown in MEM supplemented with 10% FBS. BHK-21 cells were cultivated in MEM supplemented with 10% FBS, 1% nonessential amino acids and 1 mM sodium pyruvate. CHO-K1 cells were cultivated in F-12 medium supplemented with 10% FBS and 1 mM sodium pyruvate. All cells were grown in their specific medium supplemented with 2 mM L-glutamine and a mixture of antibiotics in a humified 5% $CO_2$ atmosphere at 37° C. PK-15, BHK-21 and CHO-K1 cells were transfected respectively with lipofectamine (Invitrogen), lipofectamine 2000 (Invitrogen) and FuGENE 6 (Roche) according to the manufacturers' instructions.

Viruses

A $13^{th}$ passage on macrophages of the European prototype PRRSV strain, Lelystad virus (LV) (kindly provided by G. Wensvoort), was used (Wensvoort et al., 1991). The European PRRSV strain was first passaged on macrophages and subsequently cultivated on Marc-145 cells for 4 passages, while for the American prototype PRRSV strain, VR-2332, a $4^{th}$ passage on Marc-145 cells was used which was never passaged on macrophages (Collins et al., 1992). From the Belgian isolate 94v360 a $5^{th}$ passage on Marc-145 cells was used (Duan et al., 1997a).

Antibodies

CD163 was detected via mouse monoclonal anti-porcine CD163 antibody (mAb) 2A10 (Ab-Direct) (Bullido et al., 1997; Sanchez et al., 1999) or goat polyclonal anti-human CD163 antibody (pAb) (R&D Systems). For porcine sialoadhesin recognition, mAb 41D3 has been used (Duan et al., 1998b; Vanderheijden et al., 2003). Isotype-matched irrelevant mAb 13D12 directed against gD of pseudorabies virus (Nauwynck & Pensaert, 1995) and purified goat antibodies were used as negative controls. PRRSV was visualized via the nucleocapsid-recognizing mAb P3/27 (Wieczorek-Krohmer et al., 1996) or a polyclonal swine serum obtained from PRRSV infected pigs.

Constructs

CD163 variants differing in their cytoplasmic tail have been described (Nielsen et al., 2006). Since these variations do not appear to determine PRRSV receptor function (Calvert et al., 2007), only one variant, the short one, has been cloned. Therefore, total cellular RNA was isolated from porcine macrophages via the RNeasy Mini Kit (Qiagen) and subsequently converted into cDNA via oligo dT primers (Invitrogen) and SuperScript II reverse transcriptase (Invitrogen) followed by an RNase H (Gibco) treatment. The obtained single stranded cDNA served on its turn as template for PCR amplification of the CD163 sequence via the Platinum Pfx polymerase (Invitrogen) and following primers: forward primer 5'CAC CAT GGA CAA ACT CAG AAT GGT GCT ACA TGA AAA CTC T3' (SEQ ID NO:15) and reverse primer 5'TCA TTG TAC TTC AGA GTG GTC TCC TGA GGG ATT 3' (SEQ ID NO:16) (Invitrogen). The PCR fragment was then finally cloned in the pcDNA3.1D/V5-His-TOPO vector (Invitrogen).

Sialoadhesin was cloned into the same vector as was described by Vanderheijden et al. (Vanderheijden et al., 2003). All sequences were verified via restriction digestion and sequencing.

Stable Cell Lines

To construct a cell line co-expressing Sn and CD163, CHO-K1 cells were transfected with a plasmid containing the Sn cDNA and a geneticine resistance gene. After selection for geneticine resistance, cells were transfected with a plasmid containing the CD163 cDNA and a zeocin resistance gene, which allowed selection of cells expressing both Sn and CD163. Finally, 16 clones that co-expressed Sn and CD163 (CHOSn-CD163) were isolated. 10 clones in which 100% of the cells stably expressed Sn and CD163 were isolated, while the other 6 clones lost either Sn or CD163 receptor expression. After a first screening for susceptibility to PRRSV infection, three $CHO^{Sn-CD163}$ clones, i.e. IC5, ID9 & IF3 were selected for further research and deposited at the Belgian Coordinated Collections of Microorganisms as CHO—Sn/CD163 IC5; CHO—Sn/CD163 ID9 and CHO—Sn/CD163 IF3 with the respective accession numbers LMBP 6677CB; LMBP 6678CB; and LMBP 66779 CB respectively.

Viral Inactivation

Inactivation with ultraviolet (UV) radiation was performed with a UV cross-linker (UVP, Inc). Purified virus ($10^7$ TCID50/ml) was radiated with UV light of different doses (0-100-1000-2000-3000 or 4000 mJ/cm$^2$) (Darnell et al. 2004). Inactivation with binary ethyleneimine (BEI) was done by incubating purified virus ($10^7$ TCID50/ml) with 1 mM BEI (Aldrich) for several (0-6-12-24-48 or 72 hours) at 37° C. The reaction was stopped with 0.1 mM sodium thiosulfate (Sigma) (Mondal et al. 2005).

Flow Cytometry

Twenty-four hours after seeding, macrophages were lifted from the cell culture plate by incubation with ice-cold PBS for 30 min at 4° C. immediately prior to immunostaining and flow-cytometric analysis. Cells were first fixed with 3% paraformaldehyde followed by washing and incubation with primary mAb 41D3, 2A10 or isotype-matched control antibodies at 4° C. Afterwards, cells were washed 3 times and subsequently incubated with FITC-labeled goat-anti-mouse Ab (Molecular Probes). Finally, cells were washed 3 times, resuspended in phosphate buffered saline (PBS) and analyzed with a Becton-Dickinson (San Jose, Calif.) FACScalibur. Twenty thousand cells were analyzed for each sample and three parameters were stored for further analysis: forward light scatter, sideward light scatter and green fluorescence.

Virus Titration

To determine the titre of extracellular virus, supernatant was collected and centrifuged to remove cell debris. To determine the titre of intracellular virus, cells were washed, collected and lysed by 3 cycles of freeze-thawing. For titration on Marc-145 cells, cells were planted 3 days before inoculation. Then, they were inoculated with a 10 fold dilution series of the samples and incubated for 7 days at 37° C. followed by evaluation of the cytopathic effect (CPE). For titration on macrophages, cells were planted 1 day before inoculation followed by inoculation with a 10 fold dilution series of the samples, incubation for 3 days at 37° C. and finally evaluation. CPE was studied and furthermore infected cells were visualized via an immunoperoxidase monolayer assay (IPMA) (Wensvoort et al., 1991).

Immunofluorescence Staining and Microscopy

Transfected and/or infected cells were fixed with ice-cold methanol, unless pictures or colocalization studies were demanded. In those cases 3% paraformaldehyde was used and if needed, those cells were permeabilized with 0.1% Triton X-100. Fixation and permeabilization reagentia were removed via 3 times washing with PBS. Fixed cells were incubated with primary antibodies for at least 1 hr at 37° C., washed 3 times with PBS and further incubated with secondary antibodies for at least 1 hr at 37° C. Finally, cells were washed 3 times, embedded in glycerine-DABCO, mounted and analysed via fluorescence microscopy.

Colocalization

To quantitate colocalization between sialoadhesin and CD163 on the surface of macrophages, confocal images were taken and analysed via the programme CoLocalizer Pro. Prior to merging the two images, weak fluorescent background was substracted. Based on the overlay, different colocalization parameters were calculated according to the manual.

Treatment of Macrophages with Sialoadhesin and CD163 Specific Antibodies

Macrophages were seeded in 96-wells 24 hrs before the experiment was performed. A three-fold dilution series was prepared for different antibodies (2A10, CD163-pAb, 41D3, 13D12, purified goat antibodies) and the HbHp complex (Hb $A_o$ H0267, Hp type 2-2 H9762 from Sigma-Aldrich), which was made by 15 min incubation of both components at room temperature. Macrophages were then incubated for one hour at 37° C. with the concentration gradient of antibodies/proteins followed by inoculation with PRRSV in the presence of antibodies/proteins for one hour at 37° C. After the treatment, cells were washed, further incubated for 9 hr at 37° C. and fixed with methanol. Infected cells were visualized via an immunoperoxidase staining with mAb P3/27 or the polyclonal swine serum as primary antibodies and respectively goat-anti-mouse HRP or rabbit-anti-swine HRP (Dako) as secondary antibodies. In control reactions, no difference in the percentage of infected cells was observed for the 2 different PRRSV-recognizing antibodies. After counting the percentage of infected cells, relative percentages of infection were calculated with cells without any antibody/protein treatment as reference value represented by the RPMI data.

Infection Experiments on Non-Target Cells and on Macrophages

For different infection experiments, a similar protocol was used as will be described here. Twenty-four hours post transfection of PRRSV non-target cells or 24 hrs post seeding of the macrophages, cells were washed once with RPMI followed by inoculation with PRRSV viral supernatant which was cleared from cell debris via centrifugation. Inoculated cells were incubated for 1 hr at 37° C. in the presence of the virus. After virus removal, macrophages were directly covered with medium unlike non-target cells, which were washed 5 times with RPMI before incubation in medium. The final wash solution was collected and titrated to determine the amount of background virus still present after removal of the inoculum. At different time points after inoculation, cells were fixed with ice-cold methanol or paraformaldehyde and intra- and extracellular virus was collected as described in virus titration.

Infection Experiments on $CHO^{Sn-CD163}$ Cells

Figure 2:
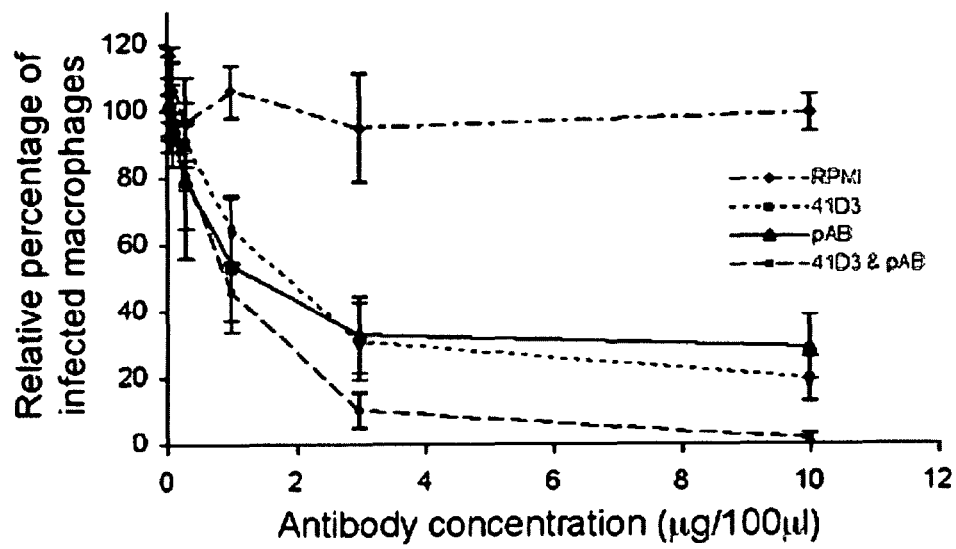
FIG. 2 Effect of sialoadhesin and CD163 specific antibodies on PRRSV infection of macrophages. A Macrophages were treated with different concentrations of sialoadhesin and CD163 recognizing antibodies at 37° C. and inoculated with Marc-grown Lelystad virus. The relative percentage of infected macrophages was calculated, with untreated cells (RPMI) as reference. Each value represents the means±standard deviation of 3 experiments. B Macrophages were treated with 3.3 μg/100 μl of sialoadhesin and CD163 specific antibodies and inoculated with different PRRSV strains. The relative percentage of infected macrophages was calculated, with untreated cells (RPMI) as reference. Each value represents the means±standard deviation of 3 experiments.
Figure 2:
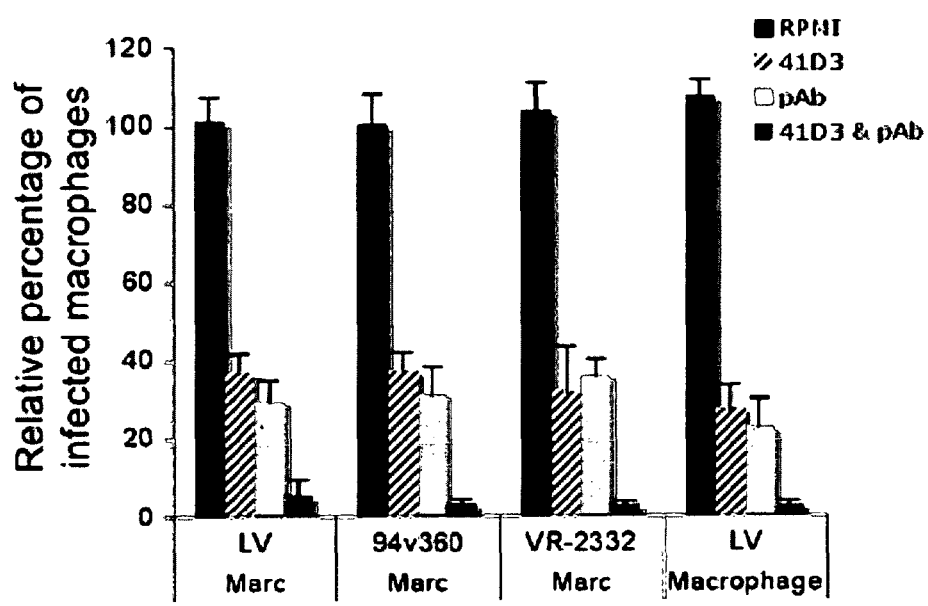

For different infection experiments, a similar protocol was used as will be described here. Three different $CHO^{Sn-CD163}$ cell clones (IC5, ID9 and IF3) seeded at different densities (100 000, 200 000 or 300 000 cells/ml) are infected at different days post seeding (1, 2 or 3 days post seeding) with LV marc grown (moi 1) or with LV macrophage grown (moi 10). After 48 hours post inoculation the cells are fixed with methanol and stained with primary antibody P3/27 and secondary antibody goat-anti-mouse HRP. Afterwards AEC substrate is added. With a microscope infected cells of 3 fields with a 40× lens (500 cells per field) are counted. To enhance virus interaction with the sialoadhesin receptor which depends on interaction of virus linked sialic acids with the N-terminal, sialic acid binding domain of Sn, and subsequent infection, the cells were treated with neuraminidae (50 mU/ml of Vibirio cholerae neuraminidase) to remove cis-acting cellular sialic acids prior to infection with the PRRSV macrophage grown viruses.

Results

1. Expression of PRRSV Receptors Sialoadhesin and CD163 on Macrophages, the in vivo Target Cells of PRRSV Both PRRSV receptors sialoadhesin and CD163 are described to be restricted to monocytes-macrophages (Duan et al., 1998b; Sanchez et al., 1999). To further investigate their role in PRRSV infection, we first wanted to confirm their presence and analyse their expression pattern in a population of macrophages. Therefore, macrophages were cultivated for 24 hours, lifted from the cell culture plate, immunostained and analysed via flow cytometry or they were cultivated for 24 hours, fixed, immunostained and analysed via confocal microscopy. Similar to previous reports, the flow cytometry data (FIG. 1A) shows that nearly 100% of the macrophages are positive for both PRRSV receptors. Thus, macrophages represent a homogenous population with respect to the expression of sialoadhesin and CD163. Immunofluorescence staining followed by confocal analysis (FIG. 1B) reveals an almost exclusive expression of sialoadhesin on the cell membrane. This is in contrast to CD163, which is clearly present on the cell membrane and also intracellularly.

2. Effect of Sialoadhesin and CD163 Specific Antibodies on PRRSV Infection of Macrophages To examine the role of CD163 in PRRSV infection of primary macrophages, the effect of a CD163-specific mAb and a pAb on PRRSV infection of macrophages was evaluated. Therefore, macrophages were pre-incubated with different concentrations of antibodies followed by inoculation of the macrophages with PRRSV in the presence of the antibodies for 1 hr, washing, further incubation for 9 hrs at 37° C., methanol-fixation and finally staining with PRRSV-specific antibodies. Relative percentages of infected macrophages are represented in FIG. 2A showing that mAb 41D3, directed against porcine sialoadhesin, strongly reduces PRRSV infection in a dose dependent manner, as has been described before (Duan et al., 1998a). Interestingly, also the CD163-specific polyclonal antibody clearly reduces PRRSV infection up to 75% in a dose dependent fashion, suggesting a role for CD163 in PRRSV infection of macrophages. However, the CD163-specific monoclonal antibody had no effect on PRRSV infection (data not shown). Also the best-characterized ligand of CD163, the hemoglobin-haptoglobin complex, did not influence PRRSV infection (data not shown). Ultimately, when 41D3 and the CD163-specific polyclonal antibody were combined, PRRSV infection was completely blocked. None of the negative controls, being irrelevant isotype-matched control antibodies, had an effect on PRRSV infection. These results clearly demonstrate that CD163 and sialoadhesin are involved in PRRSV infection of macrophages.

PRRSV displays remarkable genetic, antigenic, and clinical variability resulting in distinct groups of isolates within the same viral family (Goldberg et al., 2003), urging the need to investigate whether sialoadhesin and CD163 are involved in infection of different PRRSV strains (FIG. 2B-C). Therefore, different isolates were tested for their infectivity on macrophages in the presence of PRRSV-receptor-recognizing antibodies as described above. The European prototype PRRSV strain Lelystad virus (LV), the American prototype strain VR-2332 and the Belgian isolate 94v360 all show a clear reduction in the presence of 41D3 and the CD163-specific polyclonal antibody and an even greater reduction when both antibodies are combined. All 3 isolates used were adapted to grow on Marc-145 cells. Interestingly, the LV strain grown on macrophages without any adaptation to a cell-line shows the same trend, suggesting that the genetic diversity or the producer cells of PRRSV do not influence the need of different PRRSV strains for sialoadhesin and CD163 to infect macrophages.

Figure 3:
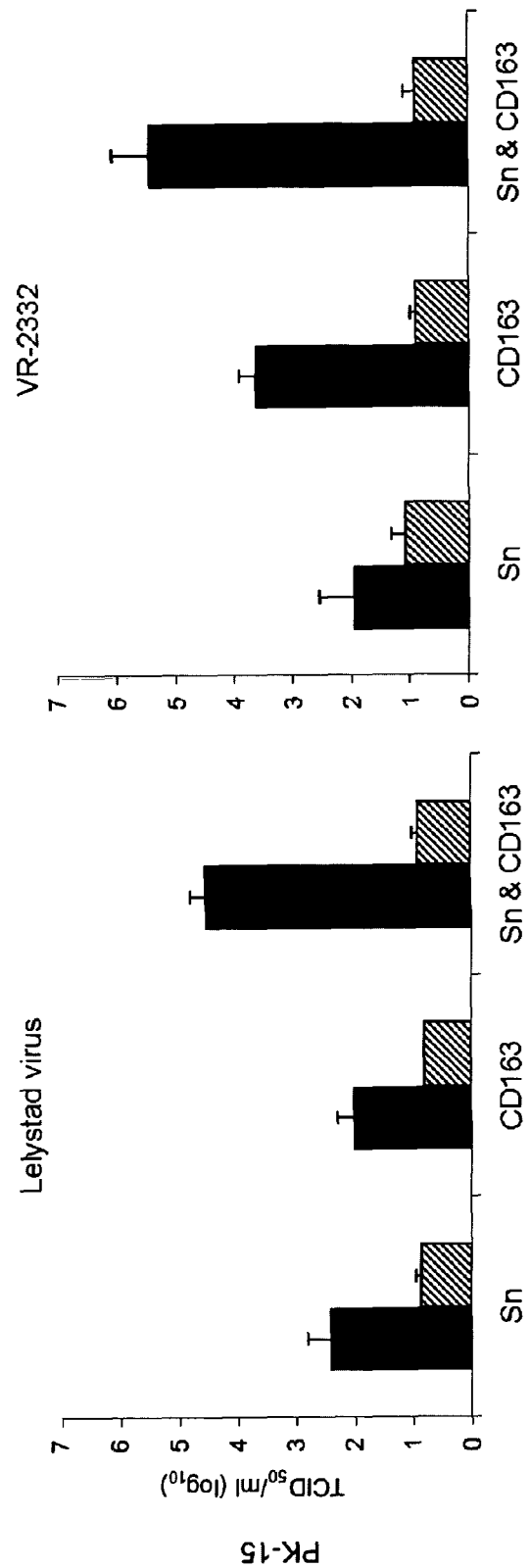
FIG. 3 PRRSV infection of non-permissive cells expressing sialoadhesin (Sn), CD163 or the combination of both. Transfected PK-15, CHO-K1 and BHK-21 cells were inoculated with either Lelystad virus or VR-2332. Twenty-four hours post inoculation, supernatant was collected and infectious extracellular virus (black bars) was determined via titration, with 0.8 tissue culture infectious doses $TCID_{50}$/ml ($log_{10}$) being the detection limit. Background virus still remaining after removal of the inoculum (grey bars) was also determined. Each value represents the means±standard deviation of 3 experiments.

3. PRRSV Non-Target Cells Expressing Both Sialoadhesin and CD163 Support Productive PRRSV Infection and are More Efficient Compared to CD163 Alone Since the experiment with antibodies showed that both sialoadhesin and CD163 are involved in PRRSV infection of macrophages, we investigated their potential role in productive PRRSV infection in different non-susceptible cell-lines, either expressed separately or combined. PK-15, CHO-K1 and BHK-21 cells were transfected with sialoadhesin, CD163 or a combination of both and 24 hrs post transfection, cells were inoculated with the European prototype Lelystad virus or the American prototype VR-2332 virus. At 24 hours post inoculation, supernatant was collected and cells were fixed. The supernatant was titrated on Marc-145 cells to determine the amount of infectious virus produced in the transiently transfected cells (FIG. 3). The fixed cells were analysed via immunofluorescence microscopy for the presence of PRRSV.

In addition to PK-15, CHO-K1 and BHK-21 cells, HEK293t cells were tested for their susceptibility to PRRSV infection. Similar to the 3 other cell lines, HEK293t cells expressing sialoadhesin did not support productive PRRSV infection. HEK293t cells expressing CD163 alone supported productive PRRSV infection and 10-100 times more infected cells were observed in cells expressing both sialoadhesin and CD163 (data not shown).

Bottom line, cells only expressing sialoadhesin never showed infection, as was already noted by Vanderhijden et al. (2003). Infected cells were only observed when CD163 was present, alone or in combination with sialoadhesin (data not shown), but where CD163 alone is able to sustain PRRSV infection, 10-100 times more infected cells were observed in cells expressing both sialoadhesin and CD163.

In agreement with the results obtained via immunofluorescence microscopy, no extracellular virus was detected for cells only expressing sialoadhesin. Except for PK-15 cells, were some extracellular virus is present, however without showing infected cells. When only CD163 is expressed, all three cell-lines produce new infectious virus, but the virus titers are rather low probably because of low infection efficiency. When both sialoadhesin and CD163 are present, all three cell-lines produce new infectious virus with virus titers remarkably higher compared to cells with only CD163, especially for PK-15 and CHO-K1 cells. Comparison between the European and the American prototype PRRSV strain shows higher virus titers for the VR-2332 strain in PK-15 and CHO-K1 cells but not in BHK-21 cells. Furthermore, for one repetition of the experiment the titration was performed not only on Marc-145 cells but also on macrophages revealing the same virus titers. Thus, PRRSV non-target cells expressing CD163 or CD163 combined with sialoadhesin produce new virus that is infectious on both Marc-145 cells and on macrophages. Further support, to the fact that non-permissive PRRSV cells can be rendered permissive with high virus titers when expression both CD163 and Sialoadhesin, was given in assessing the infectivity of the European prototype PRRSV strain Lelystad, the American prototype PRRSV strain VR-2332, and the Belgian PRRSV isolate 94V360 on the PK-15, CHO-K1, BHK-21 and HEK293t cells. For all 4 cell lines, similar results were observed as described for the 2 prototype strains. 94V360 was not able to infect cells only expressing sialoadhesin. Cells expressing CD163 were able to sustain PRRSV infection, however 10-100 times more infected cells were observed in cells expressing both sialoadhesin and CD163.

4. Kinetics of PRRSV Infection in PK-15 Cells Expressing Both Sialoadhesin and CD163

Figure 4:
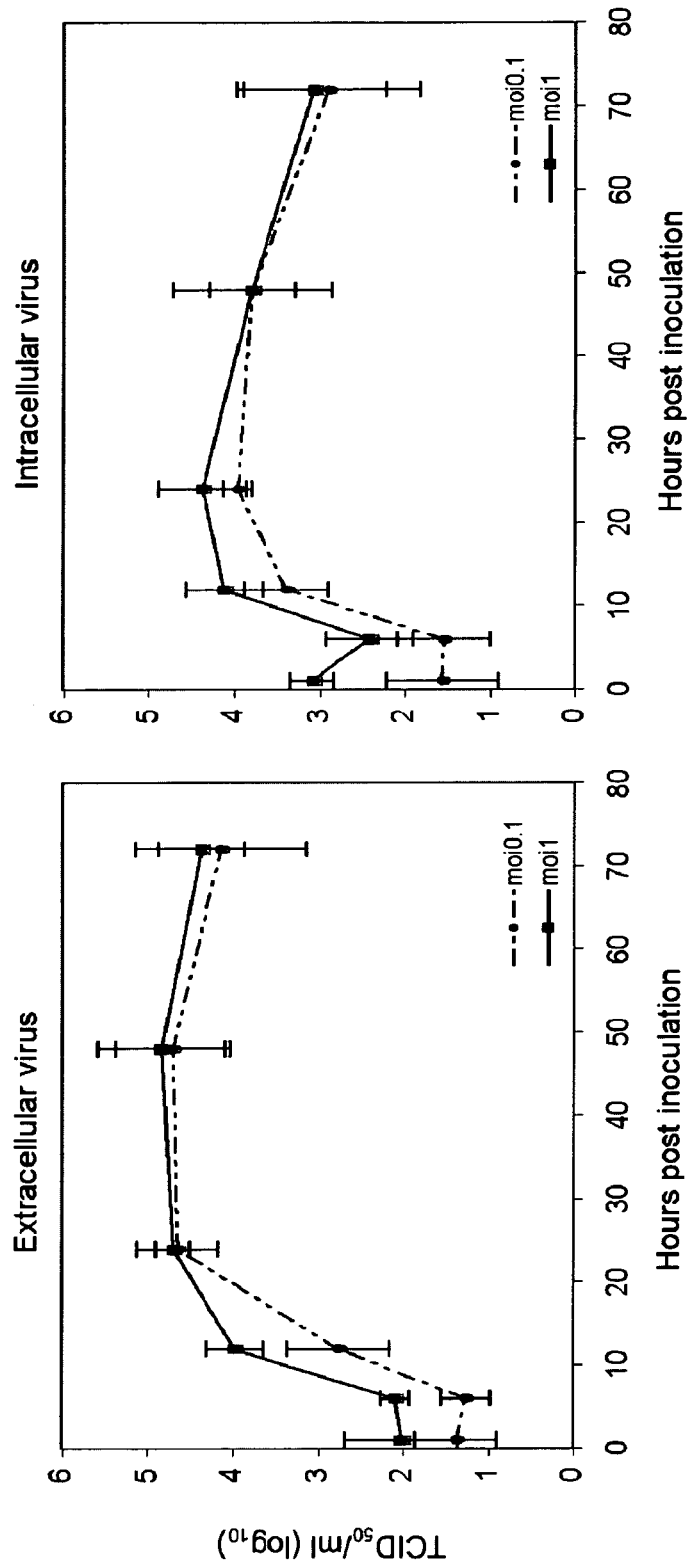
FIG. 4 Kinetics of PRRSV infection in PK-15 cells expressing sialoadhesin and CD163. PK-15 cells expressing sialoadhesin in combination with CD163 were inoculated with PRRSV at a moi of 0.1 (dashed line) or a moi of 1 (full line). At different time points after inoculation, extra—and intracellular virus was collected and titrated with 0.8 $TCID_{50}$/ml ($log_{10}$) being the detection limit. Each value represents the means±standard deviation of 3 experiments.

Because the combination of sialoadhesin and CD163 efficiently supports PRRSV infection in non-permissive cells, we wanted to study the kinetics of PRRSV infection in those non-target cells. Therefore swine kidney PK-15 cells were transfected with a combination of sialoadhesin and CD163 and 24 hrs post transfection, cells were inoculated with Lelystad virus at a moi of 0.1 or 1. At different time points after infection, intra- and extracellular virus was collected to be titrated on Marc-145 cells, as shown in FIG. 4. Starting from 12 hpi, an increase in the extracellular virus titer can be seen, which reaches its maximum around 48 hpi. Afterwards the titer drops which can possibly be explained by the limited number of sialoadhesin and CD163 expressing cells and/or the virus that becomes inactivated by the temperature. The amount of internalized virus particles is clearly dependent upon the titer in the inoculum. In the first 6 hrs, the amount of internalized virus stays the same or shows a little drop. Afterwards it increases to reach a maximum around 24 hpi. Which on its turn is followed by a decrease of the intracellular virus.

Figure 5:
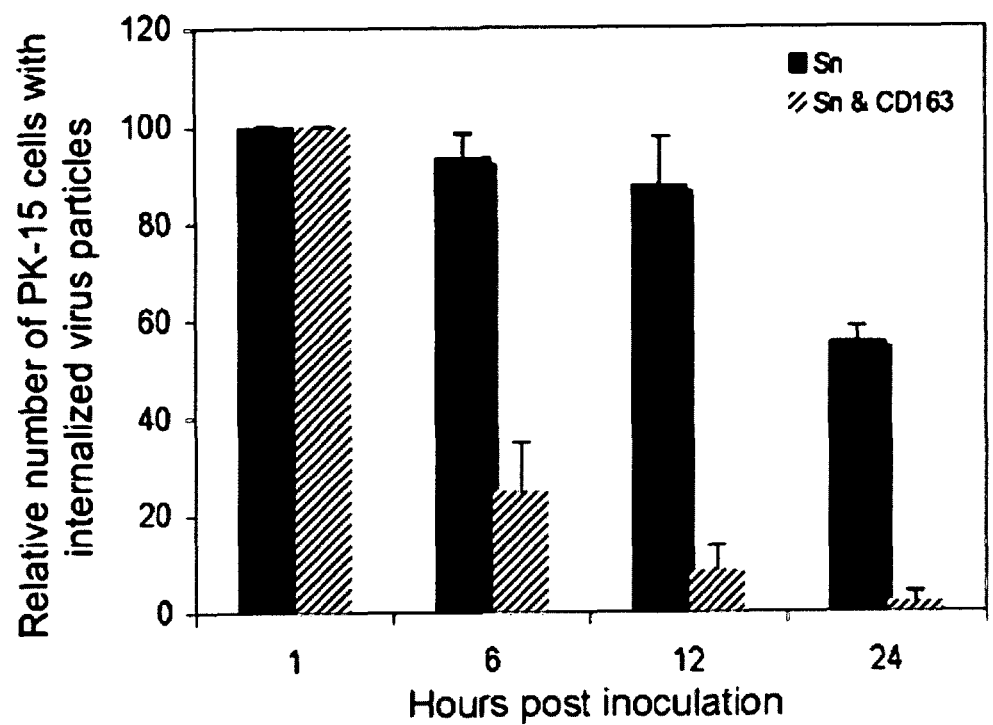
FIG. 5 Confocal microscopical analysis of PRRSV during infection of transfected PK-15 cells expressing PRRSV receptors sialoadhesin and/or CD163. The relative number of PK-15 cells with internalized virus particles was calculated with 1 hr post inoculation as reference point. Data are shown for PK-15 cells expressing sialoadhesin (black bars) and the combination of sialoadhesin and CD163 (grey bars), but not for CD163-expressing PK-15 since no internalized virus particles were observed.

5. Specific Function for Sialoadhesin and CD163 During PRRSV Infection of PK-15 Cells Since PRRSV infection of macrophages and non-target cells is clearly dependent upon sialoadhesin and CD163, their specific molecular contributions to PRRSV infection need to be investigated. Results previously obtained in the lab indicate that sialoadhesin is important for the internalization of the virus (Vanderheijden et al., 2003). We want to confirm these results and study the role of CD163 during PRRSV infection. Therefore PK-15 cells were transfected with sialoadhesin, CD163 or a combination of both, which was followed by inoculation with Lelystad virus. At different time points after infection cells were fixed and PRRSV was visualized via immunofluorescence staining with the mAb P3/27 recognizing the PRRSV nucleocapsid protein represented in FIG. 5. Sialoadhesin expressing cells clearly internalize PRRSV virus particles, however virus disassembly does not occur at any time point and the cells do not become productively infected. Only at 24 hpi there is a small decrease in the number of cells with internalized virus particles. In CD163 expressing cells, internalized virus particles could not be observed. Surprisingly, those cells become infected and produce new infectious virus particles. PK-15 cells expressing both sialoadhesin and CD163 internalize virus particles similar to sialoadhesin expressing PK-15 cells. However, due to the presence of CD163 a clear reduction in the number of cells showing internalized virus particles is observed at 6 hpi resulting in infection at 12 hpi and even more at 24 hpi. Thus, infection of cells expressing both sialoadhesin and CD163 is much more efficient than cells only expressing CD163, as has been shown before (FIG. 3). Those results confirm the role of sialoadhesin as internalization receptor and unexpectedly show a role for CD163 in fusion.

6. Treatment of Macrophages with Sialoadhesin- and CD163-Specific Antibodies at 4° C.

In addition to sialoadhesin, CD163 is shown to be involved during PRRSV entry in macrophages. Sialoadhesin is known as PRRSV attachment and internalization receptor. Our data suggest a role for CD163 during PRRSV uncoating, however, further research is needed to unravel its exact functioning. Therefore we wanted to investigate whether CD163 is involved during PRRSV attachment.

Macrophages were seeded in 96-wells 24 hrs before the experiment was performed. A three-fold dilution series was prepared for different antibodies (pAb CD163, 41D3, 13D12, purified control goat antibodies). For treatment at 4° C., macrophages were preincubated for 30 min at 4° C. prior to incubation for 1 h at 4° C. with the ligands followed by inoculation with PRRSV in the presence of a new dilution series of ligands for 1 h at 4° C. After the inoculation, cells were washed, incubated for 10 hrs at 37° C. and fixed with methanol. Infected cells were visualized via an immunoperoxidase staining with mAb P3/27 or the polyclonal swine serum as primary antibodies and respectively HRP-labelled goat-anti-mouse or rabbit-anti-swine (Dako) as secondary antibodies. No difference in the percentage of infected cells was observed for the 2 different PRRSV-recognizing antibodies. Cells without ligand treatment are represented as control. For these untreated cells the average percentage of infected cells was calculated from 6 replicates. This average percentage was used as reference value in the calculation of the relative percentages of infection.

Figure 6:
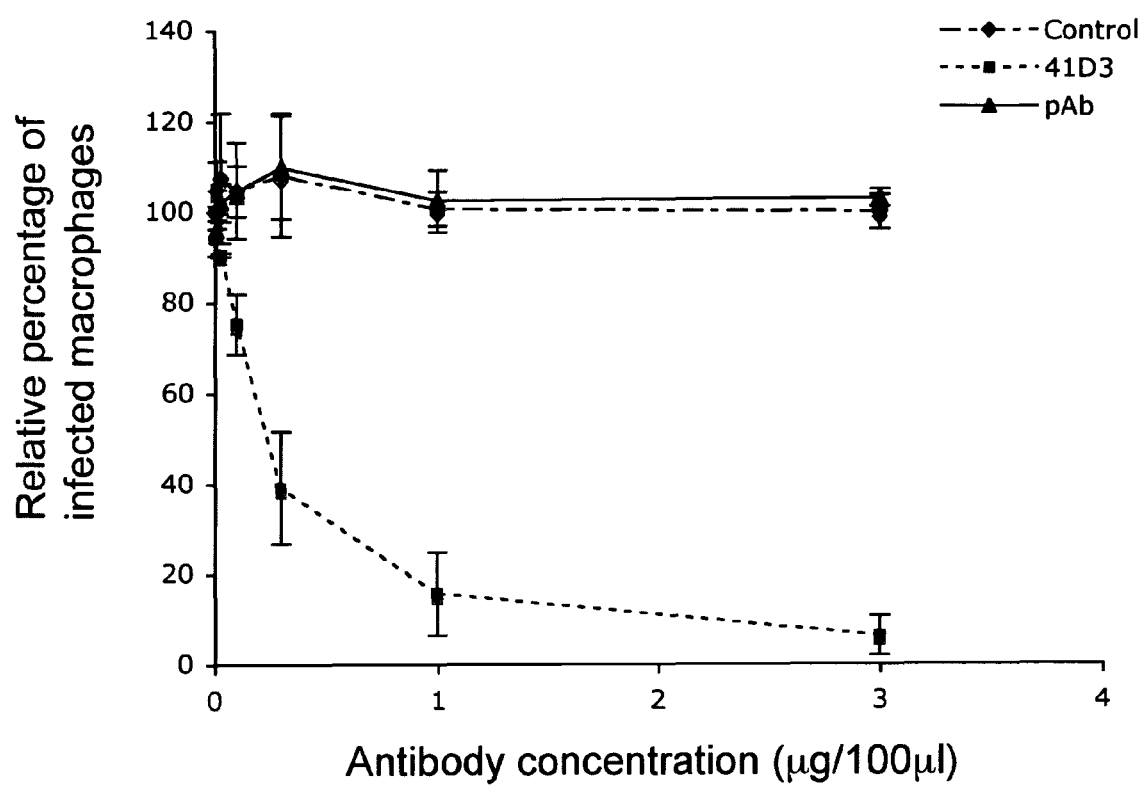
FIG. 6. Effect of sialoadhesin- and CD163-specific antibodies on PRRSV attachment to macrophages. Macrophages were treated with different concentrations of sialoadhesin- and CD163-specific antibodies at 4° C. and inoculated with Lelystad virus at 4° C. Unbound virus was then washed away and infection was allowed by shifting the cells to 37° C. for 10 h. The relative percentage of infected macrophages was calculated, with untreated cells as reference. Each value represents the means±standard deviation of 3 experiments.

Monoclonal antibody 41D3 reduced PRRSV infection, contrasting with the pAb directed against CD163, which did not reduce PRRSV infection when administered at 4° C. (FIG. 6). These data confirm the role of sialoadhesin as PRRSV attachment receptor and suggest that CD163 is not involved in PRRSV attachment to macrophages.

7. PRRSV Entry in Macrophages: Colocalization Between CD163 and PRRSV

CD163 is shown to be involved in PRRSV entry of macrophages, however not during attachment. Furthermore, CD163 enables PRRSV to disassemble and productively infect non-target cells, suggesting that CD163 acts during PRRSV entry. To test this hypothesis, we investigated the entry of PRRSV in macrophages via confocal analysis of immunofluorescence experiments showing PRRSV and CD163 at different time points after inoculation.

Twenty-four hours after seeding, macrophages were washed and incubated with PRRSV for 5, 10 or maximum 15 min at 37° C. 15 min post inoculation, the virus was replaced by medium and cells were further incubated at 37° C. At different time point post inoculation, cells were washed, fixed with paraformaldehyde, permeabilized with TX-100 and stained. Cells were first incubated with a mAb directed against GP5 (isotype IgG2a), followed by incubation with the secondary antibody goat-anti-mouse Texas Red. Cells were then again incubated with the GP5 recognizing antibody. Finally, CD163 was visualized via mAb 2A10, which was directly labeled with Alexa 488 via the mouse IgG1 specific zenon labelings kit (Invitrogen). Stainings were analysed via confocal microscopy.

PRRSV attaches to macrophages from 5 min post inoculation and first internalized virions were observed starting from 10 min post inoculation (data not shown). PRRSV bound to the surface of the macrophages did not colocalize with CD163. However, internalized virus particles ended up in CD163 positive endosomes. Starting from 45 min after inoculation, endosomes disappeared and PRRSV and CD163 started to separate. The surprising observation that PRRSV and CD163 colocalize in endosomes, this in contrast to Sn which colocalizes with PRRSV on the cell surface, further shows that CD163 is not involved in PRRSV attachment to macrophages, but rather has a role in virus fusion and uncoating inside the cell in endosomes.

8. Binding, Internalization, Fusion and Infection of PRRSV in CHO Cells Stably Expressing Sn and CD163.

Figure 7:
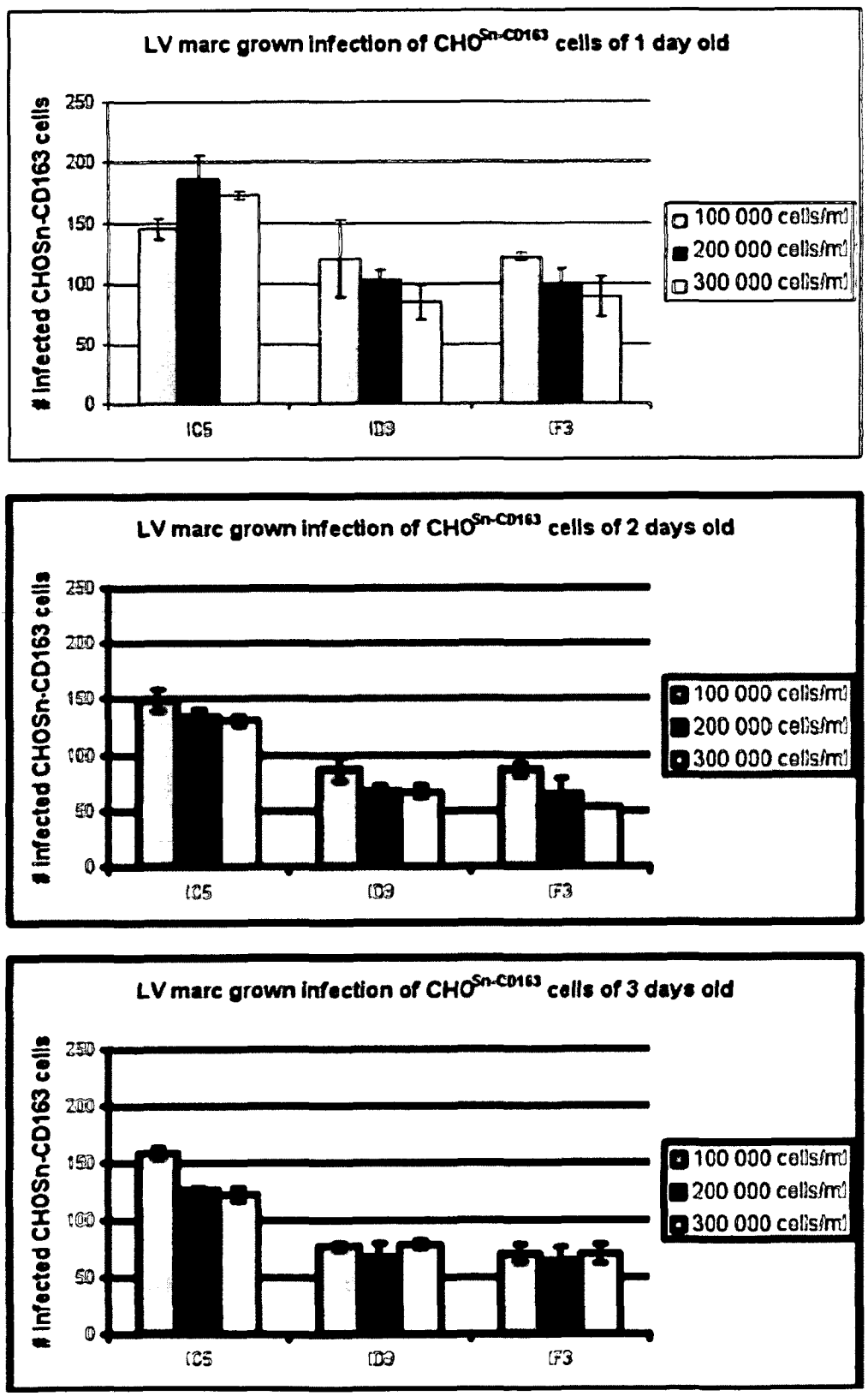
FIG. 7. Sensitivity of $CHO^{Sn-CD163}$ cells to PRRSV infection A. Three different densities of cells (100 000, 200 000 and 300 000 cells/ml were infected at 1, 2 or 3 days post seeding with LV marc-grown cells. After 48 hours cells were stained with P3/27 primary antibodies and 3 microscope fields (500 cells per field) were counted, and represented as the absolute amounts of infected cells for said microscopic fields. B. The same as A, but the cells were now pretreated with neuraminidase and subsequently infected with LV macrophage grown virus.
Figure 7:
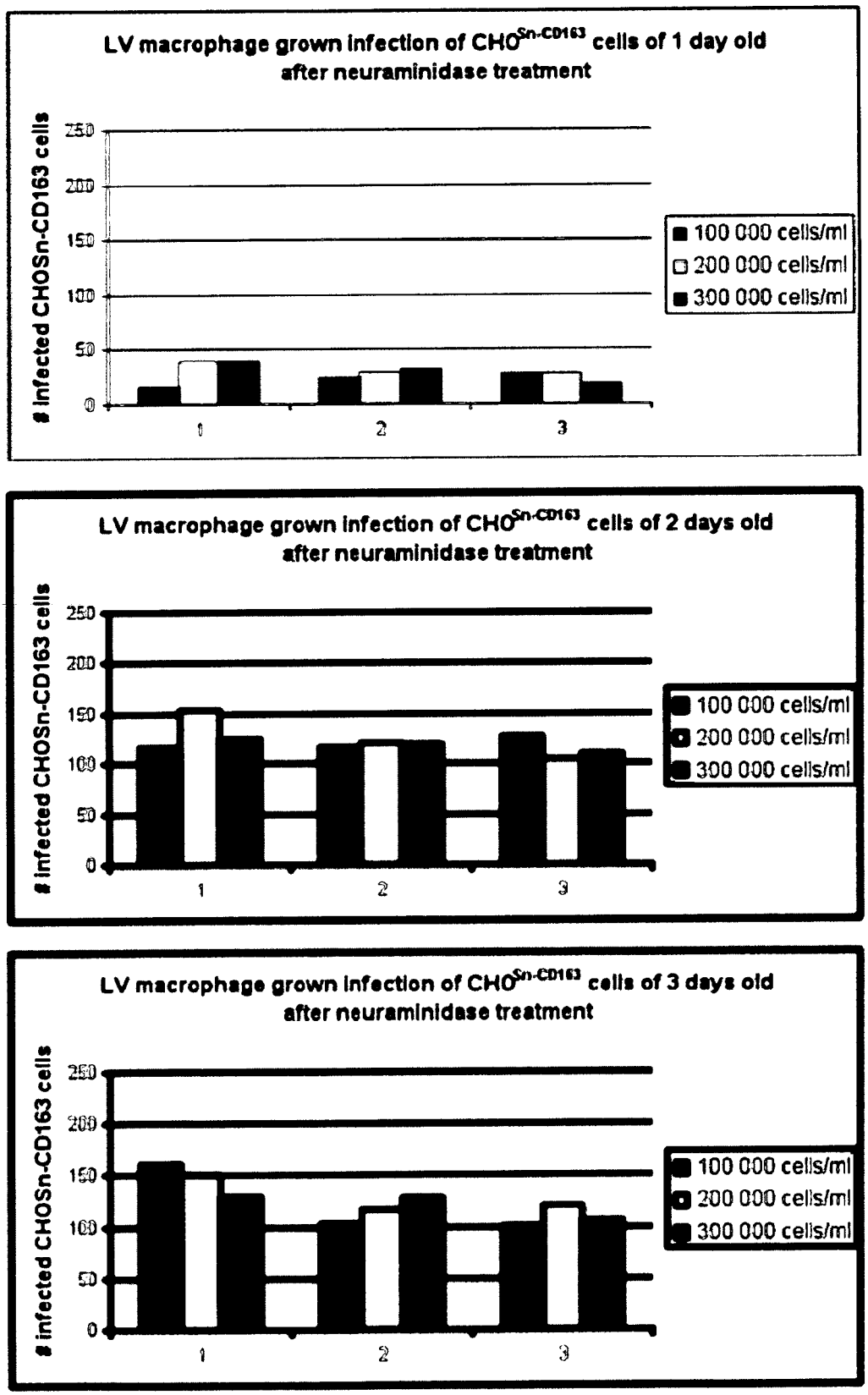

From Day 2 onwards there is little difference in the degree of infectivity of the stable $CHO^{Sn-CD163}$ cells irrespective of the fact whether the PRRSV was grown on Marc-145 cells (FIG. 7A) or macrophages (FIG. 7B). Pretreatment of the cells with neuraminidase enhanced the infection of the cells with macrophage grown PRRS virus. True permissivity of the stable $CHO^{Sn-CD163}$ cells was confirmed by immunostaining in said cells.

Three different $CHO^{Sn-CD163}$ cell clones (IC5, ID9 and IF3) were seeded at 200 000 cells/ml in a 24-well plate with insert. After 2 days the cells were inoculated with LV grown on marc cells or with inactivated LV grown on marc cells. The cells were fixed with methanol after 1 hour at 4° C. (binding, at 4° C. virus is not able to internalize), 1 hour at 37° C. (internalization), 5 hours at 37° C. (fusion, this means that virus particles are dismantled, as a consequence virus staining disappears), 12 hours at 37° C. (infection) and 24 hours at 37° C. (infection). The virus was stained with a primary antibody P3/27 and a secondary antibody goat-anti-mouse FITC. The virus particles were counted with a confocale microscope.

TABLE 1

Binding, internalization, fusion and infection of LV (control) and inactivated LV in three different CHOSn-CD163 cell lines (IC5, ID9 and IF3)

|  | control | | | BEI | | | UV | | |
| --- | --- | --- | --- | --- | --- | --- | --- | --- | --- |
|  | IC5 | ID9 | IF3 | IC5 | ID9 | IF3 | IC5 | ID9 | IF3 |
| Binding (particles) | 14 | 12 | 7 | 18 | 9 | 10 | 5 | 6 | 5 |
| Internalization (particles) | 41 | 31 | 31 | 38 | 34 | 25 | 35 | 23 | 24 |
| Fusion (particles) | 3 | 2 | 2 | 1 | 1 | 2 | 0 | 0 | 0 |
| Infection 12 hpi (%) | 0 | 0 | 0 | 0 | 0 | 0 | 0 | 0 | 0 |
| Infection 24 hpi (%) | 5 | 2 | 2 | 0 | 0 | 0 | 0 | 0 | 0 |

As shown in the aforementioned table, LV marc grown virus can perform a complete virus cycle in the three $CHO^{Sn-CD163}$ cell lines. First the virus particles bind to the cells, then virus particles inter the cells after which the particles are dismantled to release the genome. Finally infection occurs. Clearly, this shows that the infection route of PRRSV in these cells mimics the infection observed in the in vivo target cells, the macrophages. LV inactivated with BEI and UV show binding, internalization and fusion identical to the non-inactivated LV, but there is no infection, so these methods are good candidates for vaccine development. These results clearly demonstrate the use of the stable $CHO^{Sn-CD163}$ cell lines, in studying and optimizing viral inactivation processes as part of vaccine production, and accordingly provide an interesting alternative for the less accessible natural host cells.

9. Intracellular and Extracellular Virus Production on Cells Infected 2 Days Post Seeding.

Further evidence for the permissivity of the stable $CHO^{Sn-CD163}$ cells was shown when analysing the intracellular and extracellular virus production in said cells by titrating the produced virus not only on the $CHO^{Sn-CD163}$ cells, but also on the natural host (alveolar macrophages) and the Marc-145 cells known to sustain PRRSV infection. $CHO^{Sn-CD163}$ clone IC5 was infected 2 days post seeding with LV grown on marc cells, VR grown on marc cells, 94V360 grown on macrophages, similar to the infection procedures described hereinbefore. Pretreatment of the cells with neuraminidase was also included for infection with PRRSV 94V360 grown on macrophages. Titration of extracellular (extra) and intracellular (intra) was done at 3 days (Table 2) and 5 days (Table 3) post inoculation respectively and expressed as $log_{10}$ units of the $TCID_{50}$/ml.

TABLE 2 titration on different cells types (Marc-145, macrophages and $CHO^{Sn-CD163}$ clone IC5) of intra - and extra-cellular virus production 3 days post inoculation.

| | LV marc | VR marc | 94V360 macrophage | 94V360 macrophage + neuraminidase |
|---|---|---|---|---|
| Extra on marc cells | 4.3 | 4.8 | / | 3.8 |
| Extra on macrophages | 4.3 | 5.3 | 4.8 | 5.3 |
| Extra on $CHO^{Sn-CD163}$ | 3.3 | 4.8 | 2.8 | 4.3 |
| Intra on marc cells | 4.8 | 5.8 | 2.1 | 3.3 |
| Intra on macrophages | 4.3 | 5.3 | 3.8 | 4.8 |
| Intra on $CHO^{Sn-CD163}$ | 3.8 | 5.3 | / | 3.8 |

TABLE 3 titration on different cells types (Marc-145, macrophages and $CHO^{Sn-CD163}$ clone IC5) of intra - and extra-cellular virus production 5 days post inoculation.

| | LV marc | VR marc | 94V360 macrophage | 94V360 macrophage + neuraminidase |
|---|---|---|---|---|
| Extra on marc cells | 4.3 | 5.3 | / | 3.8 |
| Extra on macrophages | 5.55 | 5.3 | 4.8 | 5.3 |
| Extra on $CHO^{Sn-CD163}$ | 2.1 | 4.8 | 3.3 | 4.8 |
| Intra on marc cells | 3.1 | 4.0 | 2.1 | 2.8 |
| Intra on macrophages | 3.8 | 4.3 | 4.3 | 3.6 |
| Intra on $CHO^{Sn-CD163}$ | 2.8 | 4.3 | 3.3 | 3.3 |

Together, these results clearly show that virus is produced on $CHO^{Sn-CD163}$ cells and that this virus can infect not only $CHO^{Sn-CD163}$ cells, but also Marc-145 cells and primary macrophages, showing that no virus adaptation had occurred during infection of $CHO^{Sn-CD163}$ cells. It is in part interesting that for all the viruses produced in $CHO^{Sn-CD163}$ cells, highest levels were always detected by titration on macrophages, again showing that no adaptation during in vitro culture had occurred that would modify virus epitopes involved in infection of macrophages and induction of neutralizing antibodies.

In conclusion these results show that the $CHO^{Sn-CD163}$ cells can be used for virus production for use in vaccines or diagnosis.

REFERENCES

Bullido, R., Gomez del Moral, M., Alonso, F., Ezquerra, A., Zapata, A., Sanchez, C., Ortuno, E., Alvarez, B. & Dominguez, J. (1997). Monoclonal antibodies specific for porcine monocytes/macrophages: macrophage heterogeneity in the pig evidenced by the expression of surface antigens. Tissue antigens 49, 403-413.

Calvert, J. G., Slade, D. E., Shields, S. L., Jolie, R., Mannan, R. M., Ankenbauer, R. G. & Welch, S. K. (2007). CD163 Expression Confers Susceptibility to Porcine Reproductive and Respiratory Syndrome Viruses. J Virol.

Collins, J. E., Benfield, D. A., Christianson, W. T., Harris, L., Hennings, J. C., Shaw, D. P., Goyal, S. M., McCullough, S., Morrison, R. B., Joo, H. S. & et al. (1992). Isolation of swine infertility and respiratory syndrome virus (isolate ATCC VR-2332) in North America and experimental reproduction of the disease in gnotobiotic pigs. J Vet Diagn Invest 4, 117-126.

Delputte, P. L., Costers, S. & Nauwynck, H. J. (2005). Analysis of porcine reproductive and respiratory syndrome virus attachment and internalization: distinctive roles for heparan sulphate and sialoadhesin. The Journal of general virology 86, 1441-1445.

Delputte, P. L., Van Breedam, W., Barbé, F., Van Reeth, K. & Nauwynck, H. J. (2007). Interferon alpha treatment enhances porcine arterivirus infection of monocytes via upregulation of the porcine arterivirus receptor sialoadhesin. J Interf Cytok Res accepted.

Delputte, P. L., Vanderheijden, N., Nauwynck, H. J. & Pensaert, M. B. (2002). Involvement of the matrix protein in attachment of porcine reproductive and respiratory syndrome virus to a heparinlike receptor on porcine alveolar macrophages. J Virol 76, 4312-4320.

Duan, X., Nauwynck, H. J., Favoreel, H. W. & Pensaert, M. B. (1998b). Identification of a putative receptor for porcine reproductive and respiratory syndrome virus on porcine alveolar macrophages. J Virol 72, 4520-4523.

Duan, X., Nauwynck, H. J. & Pensaert, M. B. (1997a). Effects of origin and state of differentiation and activation of monocytes/macrophages on their susceptibility to porcine reproductive and respiratory syndrome virus (PRRSV). Archives of virology 142, 2483-2497.

Jusa, E. R., Inaba, Y., Kouno, M. & Hirose, O. (1997). Effect of heparin on infection of cells by porcine reproductive and respiratory syndrome virus. Am J Vet Res 58, 488-491.

Kim, H. S., Kwang, J., Yoon, I. J., Joo, H. S. & Frey, M. L. (1993). Enhanced replication of porcine reproductive and respiratory syndrome (PRRS) virus in a homogeneous subpopulation of MA-104 cell line. Archives of virology 133, 477-483.

Kim, J. K., Fahad, A. M., Shanmukhappa, K. & Kapil, S. (2006). Defining the cellular target(s) of porcine reproductive and respiratory syndrome virus blocking monoclonal antibody 7G10. J Virol 80, 689-696.

Kreutz, L. C. (1998). Cellular membrane factors are the major determinants of porcine reproductive and respiratory syndrome virus tropism. Virus Res 53, 121-128.

Kreutz, L. C. & Ackermann, M. R. (1996). Porcine reproductive and respiratory syndrome virus enters cells through a low pH-dependent endocytic pathway. Virus Res 42, 137-147.

Mengeling, W. L., Lager, K. M. & Vorwald, A. C. (1995). Diagnosis of porcine reproductive and respiratory syndrome. J Vet Diagn Invest 7, 3-16.

Meulenberg, J. J., Bos-de Ruijter, J. N., van de Graaf, R., Wensvoort, G. & Moormann, R. J. (1998). Infectious transcripts from cloned genome-length cDNA of porcine reproductive and respiratory syndrome virus. J Virol 72, 380-387.

Nauwynck, H. J., Duan, X., Favored, H. W., Van Oostveldt, P. & Pensaert, M. B. (1999). Entry of porcine reproductive and respiratory syndrome virus into porcine alveolar macrophages via receptor-mediated endocytosis. The Journal of general virology 80 (Pt 2), 297-305.

Nauwynck, H. J. & Pensaert, M. B. (1995). Effect of specific antibodies on the cell-associated spread of pseudorabies virus in monolayers of different cell types. Archives of virology 140, 1137-1146.

Neumann, E. J., Kliebenstein, J. B., Johnson, C. D., Mabry, J. W., Bush, E. J., Seitzinger, A. H., Green, A. L. & Zimmerman, J. J. (2005). Assessment of the economic impact of porcine reproductive and respiratory syndrome on swine production in the United States. J Am Vet Med Assoc 227, 385-392.

Nielsen, M. J., Madsen, M., Moller, H. J. & Moestrup, S. K. (2006). The macrophage scavenger receptor CD163: endocytic properties of cytoplasmic tail variants. Journal of leukocyte biology 79, 837-845.

Plagemann, P. G. & Moennig, V. (1992). Lactate dehydrogenase-elevating virus, equine arteritis virus, and simian hemorrhagic fever virus: a new group of positive-strand RNA viruses. Adv Virus Res 41, 99-192.

Sanchez, C., Domenech, N., Vazquez, J., Alonso, F., Ezquerra, A. & Dominguez, J. (1999). The porcine 2A10 antigen is homologous to human CD163 and related to macrophage differentiation. J Immunol 162, 5230-5237.

Shanmukhappa, K., Kim, J. K. & Kapil, S. (2007). Role of CD151, A tetraspanin, in porcine reproductive and respiratory syndrome virus infection. Virol J 4, 62.

Sur, J. H., Doster, A. R., Christian, J. S., Galeota, J. A., Wills, R. W., Zimmerman, J. J. & Osorio, F. A. (1997). Porcine reproductive and respiratory syndrome virus replicates in testicular germ cells, alters spermatogenesis, and induces germ cell death by apoptosis. J Virol 71, 9170-9179.

Vanderheijden, N., Delputte, P. L., Favoreel, H. W., Vanderkerckhove, J., Van Damme, J., van Woensel, P. A. & Nauwynck, H. J. (2003). Involvement of sialoadhesin in entry of porcine reproductive and respiratory syndrome virus into porcine alveolar macrophages. J Virol 77, 8207-8215.

Wensvoort, G., Terpstra, C., Pol, J. M., ter Laak, E. A., Bloemraad, M., de Kluyver, E. P., Kragten, C., van Buiten, L., den Besten, A., Wagenaar, F. & et al. (1991). Mystery swine disease in The Netherlands: the isolation of Lelystad virus. The Veterinary quarterly 13, 121-130.

Wieczorek-Krohmer, M., Weiland, F., Conzelmann, K., Kohl, D., Visser, N., van Woensel, P., Thiel, H. J. & Weiland, E. (1996). Porcine reproductive and respiratory syndrome virus (PRRSV): monoclonal antibodies detect common epitopes on two viral proteins of European and U.S. isolates. Vet Microbiol 51, 257-266.

Wissink, E. H., van Wijk, H. A., Pol, J. M., Godeke, G. J., van Rijn, P. A., Rottier, P. J. & Meulenberg, J. J. (2003). Identification of porcine alveolar macrophage glycoproteins involved in infection of porcine respiratory and reproductive syndrome virus. Archives of virology 148, 177-187.

---

The invention claimed is:

1. A method for preparing Porcine Reproductive and Respiratory Syndrome Virus (PRRSV), the method comprising:
    determining CD163 expression in a cell line;
    determining sialoadhesin expression in the cell line;
    identifying a cell line having both CD163 and sialoadhesin expression as a permissive cell line for PRRSV;
    infecting the identified cell line with PRRSV; and
    harvesting PRRSV from the cell line.

2. A method for preparing Porcine Reproductive and Respiratory Syndrome Virus (PRRSV), the method comprising:
    treating a cell to yield an expression of both CD163 and sialoadhesin;
    determining CD163 expression in the cell;
    determining sialoadhesin expression in the cell;
    identifying a cell having both CD163 and sialoadhesin expression as a permissive cell for PRRSV;
    infecting the identified cell with PRRSV; and
    harvesting PRRSV from the cell line.

3. The method according to claim 2, wherein the expression of CD163 and sialoadhesin is determined at the nucleic acid level.

4. The method according to claim 3, wherein the expression of CD163 and sialoadhesin is determined at the mRNA level.

5. The method according to claim 3, further comprising isolating nucleic acid or protein from the cell.

6. The method according to claim 4, further comprising isolating mRNA from the cell.

7. The method according to claim 3, further comprising contacting the cell or an extract thereof with an antibody for CD163 or sialoadhesin.

8. The method according to claim 1, wherein the expression of CD163 and sialoadhesin is determined at the protein level.

9. The method of claim 8, wherein the protein level is determined using an immunological method.

10. The method according to claim 2, wherein the CD163 protein is at least 70% identical to porcine CD163 encoded by the gene characterized by SEQ ID NO:1, including biologically active fragments thereof containing at least one Scavenger Receptor Cysteine Rich (SRCR) domain.

11. The method according to claim 2, wherein the sialoadhesin protein is at least 70% identical to porcine sialoadhesin encoded by the gene characterized by SEQ ID NO:9, including biologically active fragments thereof containing at least the N-terminal domain.

12. The method according to claim 2, further comprising the step of inactivating the virus harvested from the cell culture.

13. The method according to claim 2, wherein treating a cell comprises the introduction of exogenous nucleic acid into the cell.

14. The method according to claim 13, wherein the exogenous nucleic acid encodes CD163 and/or sialoadhesin.

\* \* \* \* \*

UNITED STATES PATENT AND TRADEMARK OFFICE
CERTIFICATE OF CORRECTION

PATENT NO.       : 8,420,373 B2
APPLICATION NO.  : 12/452675
DATED            : April 16, 2013
INVENTOR(S)      : Delputte et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 310 days.

Signed and Sealed this
First Day of September, 2015

Michelle K. Lee
*Director of the United States Patent and Trademark Office*